(12) United States Patent
Jeon et al.

(10) Patent No.: US 9,960,365 B2
(45) Date of Patent: May 1, 2018

(54) CONDENSED CYCLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Soonok Jeon, Seoul (KR); Jhunmo Son, Yongin-si (KR); Sangmo Kim, Hwaseong-si (KR); Hyunjung Kim, Hwaseong-si (KR); Yeonsook Jung, Yongin-si (KR); Yongsik Jung, Yongin-si (KR); Dalho Huh, Yongin-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 313 days.

(21) Appl. No.: 14/688,434

(22) Filed: Apr. 16, 2015

(65) Prior Publication Data

US 2016/0093811 A1 Mar. 31, 2016

(30) Foreign Application Priority Data

Sep. 26, 2014 (KR) .................. 10-2014-0129513

(51) Int. Cl.
| | | |
|---|---|---|
| *C07D 403/14* | (2006.01) | |
| *H01L 51/00* | (2006.01) | |
| *C09K 11/06* | (2006.01) | |
| *C09K 11/02* | (2006.01) | |
| *H01L 51/50* | (2006.01) | |

(52) U.S. Cl.
CPC ........ *H01L 51/0072* (2013.01); *C07D 403/14* (2013.01); *C09K 11/025* (2013.01); *C09K 11/06* (2013.01); *H01L 51/0067* (2013.01); *C09K 2211/1074* (2013.01); *H01L 51/0085* (2013.01); *H01L 51/5016* (2013.01)

(58) Field of Classification Search
CPC ............ H01L 51/0067; H01L 51/0072; C07D 403/14; C09K 11/025; C09K 11/06
See application file for complete search history.

(56) References Cited

U.S. PATENT DOCUMENTS

| | | | |
|---|---|---|---|
| 8,071,414 B2 | 12/2011 | Yu et al. | |
| 8,586,967 B2 | 11/2013 | Xue et al. | |
| 8,629,122 B2 | 1/2014 | Takahashi et al. | |
| 2005/0217722 A1 | 10/2005 | Komatsu et al. | |
| 2012/0091020 A1 | 4/2012 | Glinert et al. | |
| 2013/0105768 A1 | 5/2013 | Leem et al. | |
| 2014/0272398 A1* | 9/2014 | Hakii ................ B32B 15/04 | |
| | | | 428/336 |

FOREIGN PATENT DOCUMENTS

| | | |
|---|---|---|
| CN | 103468246 | 12/2013 |
| KR | 1020140004549 | 1/2014 |
| KR | 1020140008235 | 1/2014 |
| KR | 1020140044336 | 4/2014 |
| KR | 101480125 | 12/2014 |

* cited by examiner

*Primary Examiner* — Edward J Cain
(74) *Attorney, Agent, or Firm* — Cantor Colburn LLP

(57) ABSTRACT

A condensed cyclic compound represented by Formula 1:

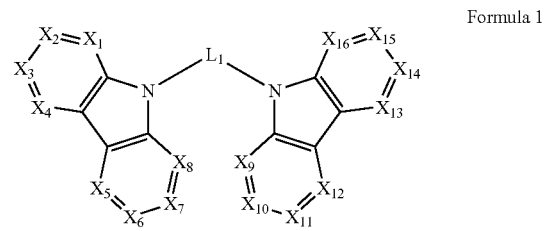

wherein in Formula 1, groups $L_1$ and $X_1$ to $X_{16}$ are the same as described in the specification.

20 Claims, 5 Drawing Sheets

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2014-0129513, filed on Sep. 26, 2014, in the Korean Intellectual Property Office, and all the benefits accruing therefrom under 35 U.S.C. §119, the content of which is incorporated herein in its entirety by reference.

BACKGROUND

1. Field

One or more embodiments relate to a condensed cyclic compound and an organic light-emitting device including the same.

2. Description of the Related Art

Organic light emitting devices (OLEDs) are self-emission devices that have wide viewing angles, high contrast ratios, and short response times. In addition, OLEDs exhibit excellent brightness, driving voltage, and response speed characteristics, and produce full-color images.

In an example, an organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, are recombined in the emission layer to produce excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

One or more embodiments relate to a condensed cyclic compound and an organic light-emitting device including the same.

Additional aspects will be set forth in part in the description which follows and, in part, will be apparent from the description, or may be learned by practice of the presented exemplary embodiments.

An aspect of embodiments provides a condensed cyclic compound represented by Formula 1:

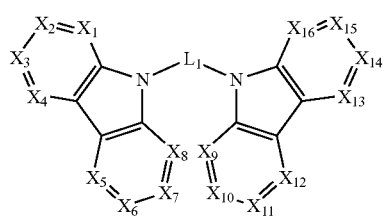

Formula 1 wherein in Formula 1,
$L_1$ is selected from a phenylene group, a pyridinylene group, a pyrimidinylene group, and a triazinylene group;
$X_1$ is N or $CR_1$;
$X_2$ is N or $CR_2$;
$X_3$ is N or $CR_3$;
$X_4$ is N or $CR_4$;
$X_5$ is N or $CR_5$;
$X_6$ is N or $CR_6$;
$X_7$ is N or $CR_7$;
$X_8$ is N or $CR_8$;
$X_9$ is N or $CR_9$;
$X_{10}$ is N or $CR_{10}$;
$X_{11}$ is N or $CR_{11}$;
$X_{12}$ is N or $CR_{12}$;
$X_{13}$ is N or $CR_{13}$;
$X_{14}$ is N or $CR_{14}$;
$X_{15}$ is N or $CR_{15}$;
$X_{16}$ is N or $CR_{16}$;
$R_1$ to $R_{16}$ is each independently selected from $R_{ET}$, a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_1$-$C_{60}$ alkoxy group, a substituted or unsubstituted $C_3$-$C_{10}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;
at least one selected from $X_1$ to $X_{16}$ is $CR_{ET}$;
$R_{ET}$ is represented by any one of Formulae 2-1 to 2-8:

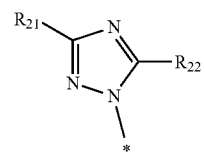

2-1

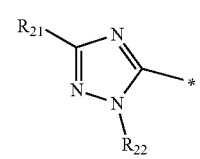

2-2

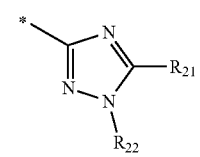

2-3

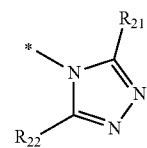

2-4

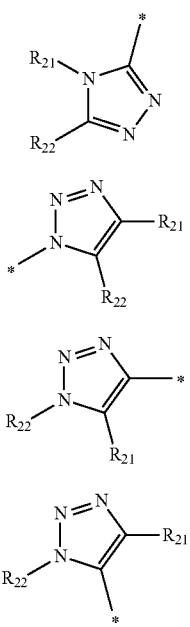

wherein in Formulae 2-1 to 2-8, $R_{21}$ and $R_{22}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_1$-$C_{60}$ alkoxy group, a substituted or unsubstituted $C_3$-$C_{10}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

* indicates a binding site to a neighboring atom, and at least one of substituents of the substituted $C_1$-$C_{60}$ alkyl group, substituted $C_1$-$C_{60}$ alkoxy group, substituted $C_3$-$C_{10}$ cycloalkyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_1$-$C_{60}$ alkenyl group, a $C_1$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$); and —Si($Q_{31}$)($Q_{32}$)($Q_{33}$), wherein $Q_{11}$ to $Q_{13}$, $Q_{21}$ to $Q_{23}$ and $Q_{31}$ to $Q_{33}$ may be each independently selected from a $C_1$-$C_{60}$ alkyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

Another aspect of embodiments provides an organic light-emitting device including:

a first electrode;

a second electrode; and an organic layer disposed between the first electrode and the second electrode, wherein the organic layer includes an emission layer and at least one of the condensed cyclic compound described above.

The condensed cyclic compound may be included in the emission layer, the emission layer may further include a dopant, and the condensed cyclic compound included in the emission layer may act as a host.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
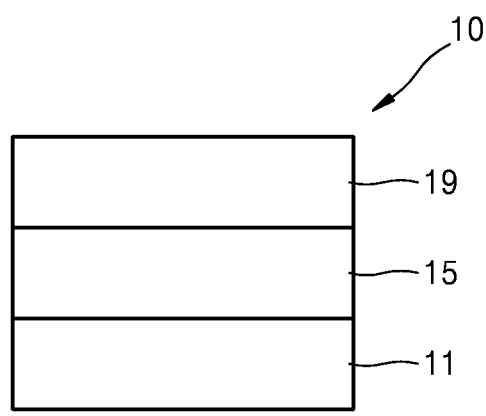
FIG. 1 is a schematic cross-sectional view of an organic light-emitting device according to an embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

A condensed cyclic compound according to an embodiment may be represented by Formula 1:

Formula 1

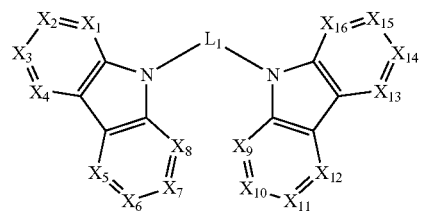

$L_1$ in Formula 1 may be selected from a phenylene group, a pyridinylene group, a pyrimidinylene group, and a triazinylene group.

In some embodiments, $L_1$ in Formula 1 may be selected from Formulae 3-1 to 3-14 below, but are not limited thereto:

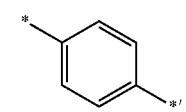

3-1

-continued 3-2 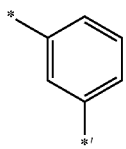

3-3 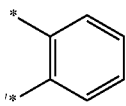

3-4 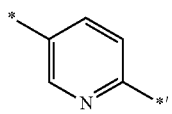

3-5 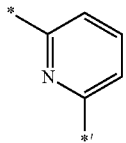

3-6 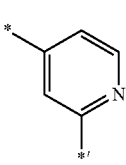

3-7 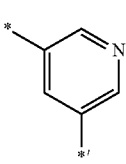

3-8 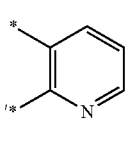

3-9 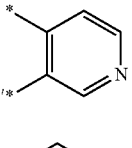

3-10 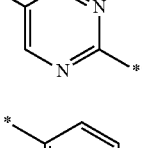

3-11 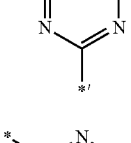

3-12 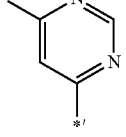

-continued 3-13 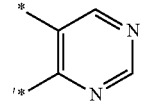

3-14 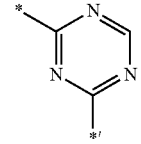

wherein in Formulae 3-1 to 3-14,

* and *' indicate each independently a binding site to a neighboring atom.

In some embodiments, $L_1$ in Formula 1 may be selected from Formulae 3-2, 3-3, 3-5 to 3-9, and 3-11 to 3-14, but embodiments are not limited thereto.

In some embodiments, $L_1$ in Formula 1 may be selected from Formulae 3-2, 3-5, 3-6, 3-7, 3-11, 3-12, and 3-14, but embodiments are not limited thereto.

In Formula 1, $X_1$ may be a nitrogen atom (N) or $CR_1$; $X_2$ is N or $CR_2$; $X_3$ is N or $CR_3$; $X_4$ is N or $CR_4$; $X_5$ is N or $CR_5$; $X_6$ is N or $CR_6$; $X_7$ is N or $CR_7$; $X_5$ is N or $CR_8$; $X_9$ is N or $CR_9$; $X_{10}$ is N or $CR_{10}$; $X_{11}$ is N or $CR_{11}$; $X_{12}$ is N or $CR_{12}$; $X_{13}$ is N or $CR_{13}$; $X_{14}$ is N or $CR_{14}$; $X_{15}$ is N or $CR_{15}$; and $X_{16}$ is N or $CR_{16}$.

In some embodiments, in Formula 1, $X_1$ may be $CR_1$; $X_2$ may be $CR_2$; $X_3$ may be $CR_3$; $X_4$ may be $CR_4$; $X_5$ may be $CR_5$; $X_6$ may be $CR_6$; $X_7$ may be $CR_7$; $X_8$ may be $CR_8$; $X_9$ may be $CR_9$; $X_{10}$ may be $CR_{10}$; $X_{11}$ may be $CR_{11}$; $X_{12}$ may be $CR_{12}$; $X_{13}$ may be $CR_{13}$; $X_{14}$ may be $CR_{14}$; $X_{15}$ may be $CR_{15}$; and $X_{16}$ may be $CR_{16}$, but embodiments are not limited thereto.

In some embodiments, in Formula 1, $X_1$ may be N; $X_2$ may be $CR_2$; $X_3$ may be $CR_3$; $X_4$ may be $CR_4$; $X_5$ may be $CR_5$; $X_6$ may be $CR_6$; $X_7$ may be $CR_7$; $X_8$ may be $CR_8$; $X_9$ may be $CR_9$; $X_{10}$ may be $CR_{10}$; $X_{11}$ may be $CR_{11}$; $X_{12}$ may be $CR_{12}$; $X_{13}$ may be $CR_{13}$; $X_{14}$ may be $CR_{14}$; $X_{15}$ may be $CR_{15}$; and $X_{16}$ may be $CR_{16}$, but embodiments are not limited thereto.

In some embodiments, in Formula 1, $X_1$ may be $CR_1$; $X_2$ may be N; $X_3$ may be $CR_3$; $X_4$ may be $CR_4$; $X_5$ may be $CR_5$; $X_6$ may be $CR_6$; $X_7$ may be $CR_7$; $X_8$ may be $CR_8$; $X_9$ may be $CR_9$; $X_{10}$ may be $CR_{10}$; $X_{11}$ may be $CR_{11}$; $X_{12}$ may be $CR_{12}$; $X_{13}$ may be $CR_{13}$; $X_{14}$ may be $CR_{14}$; $X_{15}$ may be $CR_{15}$; and $X_{16}$ may be $CR_{16}$, but embodiments are not limited thereto.

In some embodiments, in Formula 1, $X_1$ may be N; $X_2$ may be $CR_2$; $X_3$ may be $CR_3$; $X_4$ may be $CR_4$; $X_5$ may be $CR_5$; $X_6$ may be $CR_6$; $X_7$ may be $CR_7$; $X_8$ may be N; $X_9$ may be $CR_9$; $X_{10}$ may be $CR_{10}$; $X_{11}$ may be $CR_{11}$; $X_{12}$ may be $CR_{12}$; $X_{13}$ may be $CR_{13}$; $X_{14}$ may be $CR_{14}$; $X_{15}$ may be $CR_{15}$; and $X_{16}$ may be $CR_{16}$, but embodiments are not limited thereto.

In some embodiments, in Formula 1, $X_1$ may be $CR_1$; $X_2$ may be N; $X_3$ may be $CR_3$; $X_4$ may be $CR_4$; $X_5$ may be $CR_5$; $X_6$ may be $CR_6$; $X_7$ may be N; $X_8$ may be $CR_8$; $X_9$ may be $CR_9$; $X_{10}$ may be $CR_{10}$; $X_{11}$ may be $CR_{11}$; $X_{12}$ may be $CR_{12}$; $X_{13}$ may be $CR_{13}$; $X_{14}$ may be $CR_{14}$; $X_{15}$ may be $CR_{15}$; and $X_{16}$ may be $CR_{16}$, but embodiments are not limited thereto.

$R_1$ to $R_{16}$ in Formula 1 may be each independently selected from $R_{ET}$, a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_1$-$C_{60}$ alkoxy group, a substituted or unsubstituted $C_3$-$C_{10}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

at least one of substituents of the substituted $C_1$-$C_{60}$ alkyl group, substituted $C_1$-$C_{60}$ alkoxy group, substituted $C_3$-$C_{10}$ cycloalkyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_1$-$C_{60}$ alkenyl group, a $C_1$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$); and —Si($Q_{31}$)($Q_{32}$)($Q_{33}$), wherein $Q_{11}$ to $Q_{13}$, $Q_{21}$ to $Q_{23}$ and $Q_{31}$ to $Q_{33}$ may be each independently selected from a $C_1$-$C_{60}$ alkyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and $R_{ET}$ will be described later in detail.

For example, $R_1$ to $R_{16}$ in Formula 1 may be each independently selected from $R_{ET}$, a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, an n-pentyl group, an n-hexyl group, a methoxy group, an ethoxy group, an n-propoxy group, an iso-propoxy group, an n-butoxy group, a tert-butoxy group, a cyclopentyl group, a cyclohexyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a methyl group, an ethyl group, an n-propyl group, an iso-propyl group, an n-butyl group, an iso-butyl group, a sec-butyl group, a tert-butyl group, an n-pentyl group, an n-hexyl group, a methoxy group, an ethoxy group, an n-propoxy group, an iso-propoxy group, an n-butoxy group, a tert-butoxy group, a cyclopentyl group, a cyclohexyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, but embodiments are not limited thereto.

In some embodiments, $R_1$ to $R_{16}$ in Formula 1 may be each independently selected from $R_{ET}$, a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group, and a dibenzothiophenyl group; and a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group and a dibenzothiophenyl group, each substituted with at least one selected from a deuterium, —F, —Cl, —Br, —I, a hydroxyl group, a cyano group, a nitro group, a $C_1$-$C_{20}$ alkyl group, a phenyl group, a naphthyl group, a pyridinyl group, a pyrimidinyl group, and a triazinyl group, but embodiments are not limited thereto.

In some embodiments, $R_1$ to $R_{16}$ in Formula 1 may be each independently selected from $R_{ET}$, a hydrogen, a deuterium, —F, —Cl, —Br, —I, a cyano group, a nitro group, a methyl group, an ethyl group, an n-propyl group, an iso-propyl group, an n-butyl group, an iso-butyl group, a sec-butyl group, a tert-butyl group, a phenyl group, and a naphthyl group, but embodiments are not limited thereto.

At least one selected from $X_1$ to $X_{16}$ in Formula 1 may be $CR_{ET}$.

For example, one or two selected from $X_1$ to $X_{16}$ in Formula 1 may be selected from $CR_{ET}$, but embodiments are not limited thereto.

In some embodiments, at least one selected from $X_1$ to $X_{16}$ in Formula 1 may be $CR_{ET}$, but embodiments are not limited thereto.

In some embodiments, at least one selected from $X_{11}$ and $X_{14}$ in Formula 1 may be $CR_{ET}$, but embodiments are not limited thereto.

In some embodiments, $X_{14}$ in Formula 1 may be $CR_{ET}$, but embodiments are not limited thereto.

In some embodiments, at least one selected from $X_{10}$ and $X_{15}$ in Formula 1 may be $CR_{ET}$, but embodiments are not limited thereto.

In some embodiments, $X_{15}$ in Formula 1 may be $CR_{ET}$, but embodiments are not limited thereto.

$R_{ET}$ in Formula 1 may be a group represented by any one of Formulae 2-1 to 2-8:

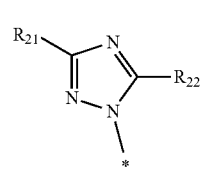

2-1

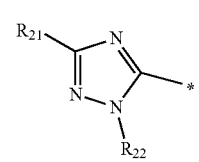

2-2

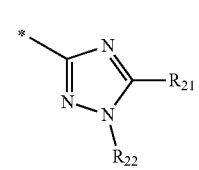

2-3

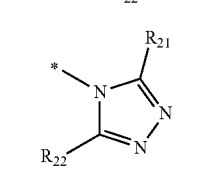

2-4

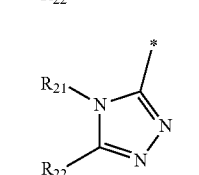

2-5

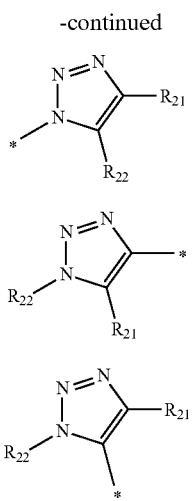

2-6

2-7

2-8

In Formulae 2-1 to 2-8, $R_{21}$ and $R_{22}$ will be described in detail later, and * indicates a binding site to a neighboring atom.

For example, $R_{ET}$ in Formula 1 may be a group represented by any one selected from Formulae 2-1, 2-3, 2-4, and 2-6, but embodiments are not limited thereto.

$R_{21}$ and $R_{22}$ in Formulae 2-1 to 2-8 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_1$-$C_{60}$ alkoxy group, a substituted or unsubstituted $C_3$-$C_{10}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

at least one of substituents of the substituted $C_1$-$C_{60}$ alkyl group, substituted $C_1$-$C_{60}$ alkoxy group, substituted $C_3$-$C_{10}$ cycloalkyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_1$-$C_{60}$ alkenyl group, a $C_1$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$); and —Si($Q_{31}$)($Q_{32}$)($Q_{33}$), wherein $Q_{11}$ to $Q_{13}$, $Q_{21}$ to $Q_{23}$ and $Q_{31}$ to $Q_{33}$ may be each independently selected from a $C_1$-$C_{60}$ alkyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

$R_{21}$ and $R_{22}$ in Formulae 2-1 to 2-8 may be each independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a furinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a methyl group, an ethyl group, an n-propyl group, an iso-propyl group, an n-butyl group, an iso-butyl group, a sec-butyl group, a tert-butyl group, an n-pentyl group, an n-hexyl group, a methoxy group, an ethoxy group, an n-propoxy group, an iso-propoxy group, an n-butoxy group, a tert-butoxy group, a cyclopentyl group, a cyclohexyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, but embodiments are not limited thereto.

In some embodiments, $R_{21}$ and $R_{22}$ in Formulae 2-1 to 2-8 may be each independently selected from a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, an n-pentyl group, an n-hexyl group, a methoxy group, an ethoxy group, an n-propoxy group, an iso-propoxy group, an n-butoxy group, a tert-butoxy group, a cyclopentyl group, a cyclohexyl group, a phenyl group, a naphthyl group, a fluorenyl group, a pyridinyl group, a pyrimidinyl group, a pyridazinyl group, and a triazinyl group; and a phenyl group, a naphthyl group, a fluorenyl group, a pyridinyl group, a pyrimidinyl group, a pyridazinyl group, and a triazinyl group, each substituted with at least one selected from a deuterium, —F, —Cl, —Br, —I, a hydroxyl group, a cyano group, a nitro group, a $C_1$-$C_{20}$ alkyl group, a phenyl group, a naphthyl group, a pyridinyl group, a pyrimidinyl group, and a triazinyl group, but embodiments are not limited thereto.

In some embodiments, $R_{21}$ and $R_{22}$ in Formulae 2-1 to 2-8 may be each independently selected from a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, an n-pentyl group, an n-hexyl group, a phenyl group, a naphthyl group, a pyridinyl group, a pyrimidinyl group, a pyridazinyl group, and a triazinyl group; and a phenyl group substituted with at least one selected from —F and a cyano group, but embodiments are not limited thereto.

In some embodiments, $R_{21}$ and $R_{22}$ in Formulae 2-1 to 2-8 may be each independently selected from a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, an n-pentyl group, an n-hexyl group, and a group represented by Formulae 4-1 to 4-11 below, but embodiments are not limited thereto:

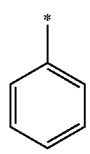

4-1

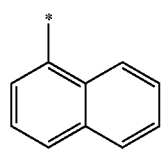

4-2

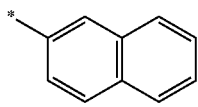

4-3

4-4 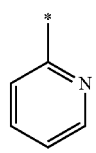
4-5 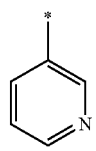
4-6 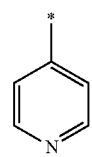
4-7 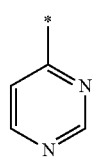
4-8 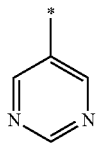
4-9 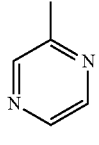
4-10 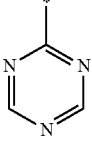
4-11 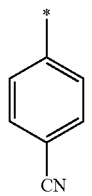
wherein in Formulae 4-1 to 4-11,
* indicates a binding site to a neighboring atom.
In some embodiments, $R_{ET}$ in Formula 1 may be a group represented by any one selected from Formulae 5-1 to 5-24, but embodiments are not limited thereto:
5-1 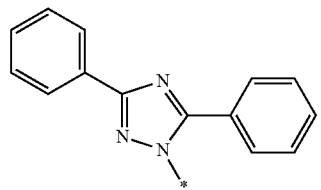
5-2 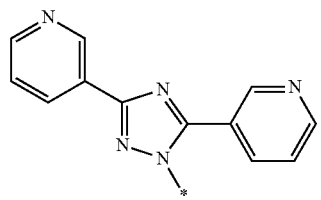
5-3 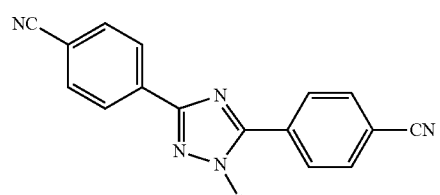
5-4 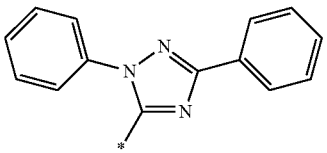
5-5 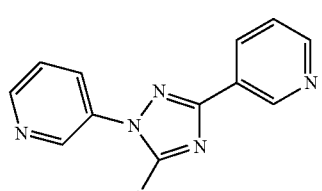
5-6 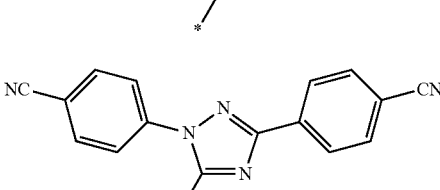
5-7 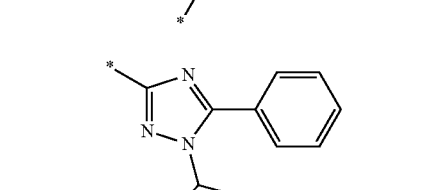
5-8 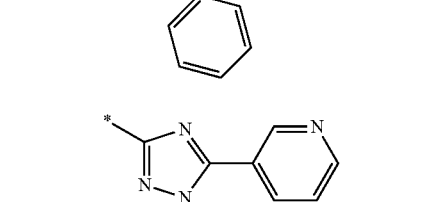

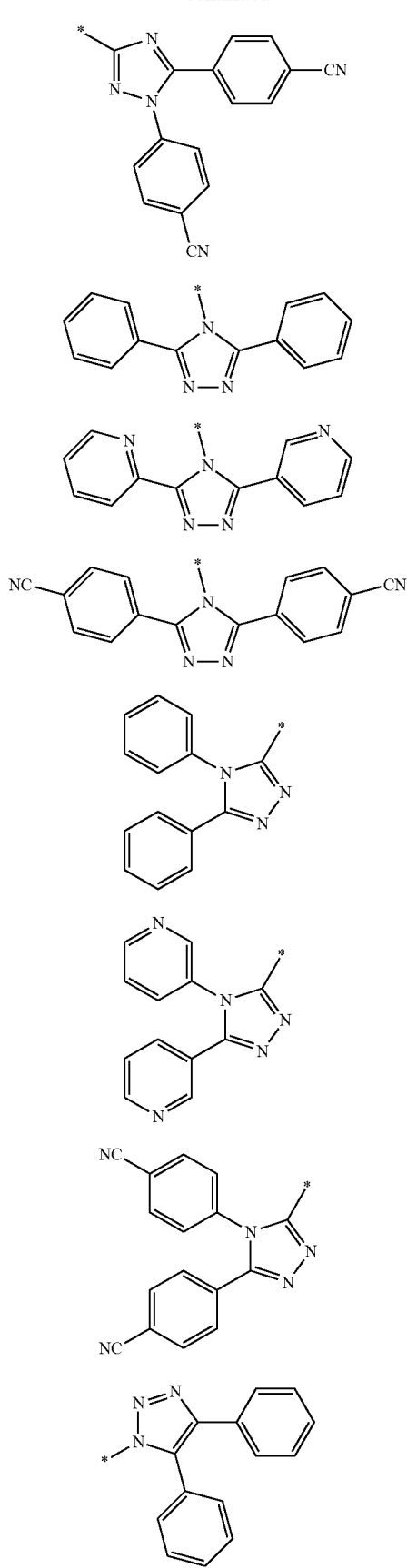
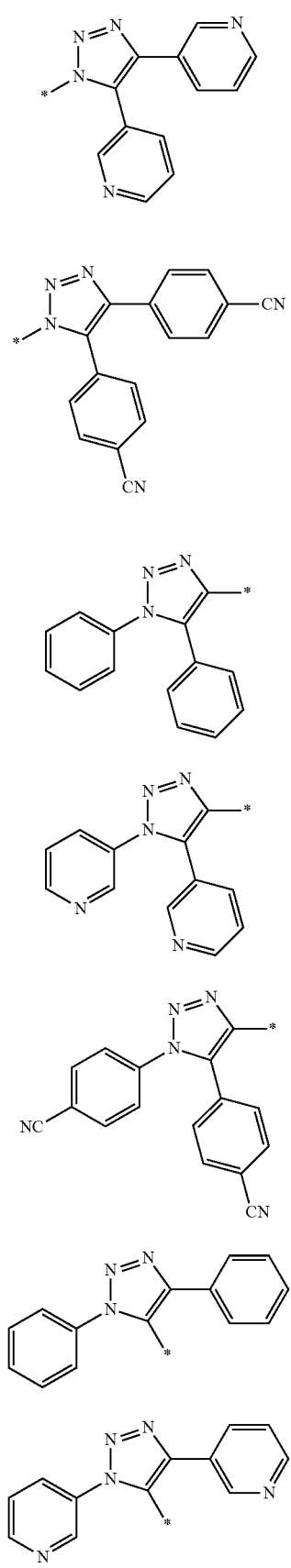

-continued

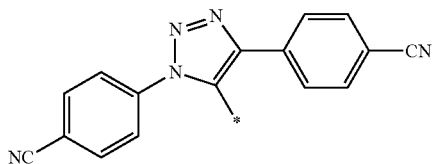
5-24 wherein in Formulae 5-1 to 5-24,

\* indicates a binding site to a neighboring atom.

In some embodiments, the condensed cyclic compound may be represented by any one of Formulae 1A to 1E:

Formula 1A
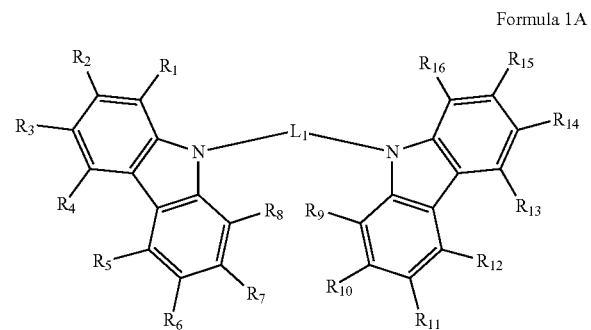

Formula 1B
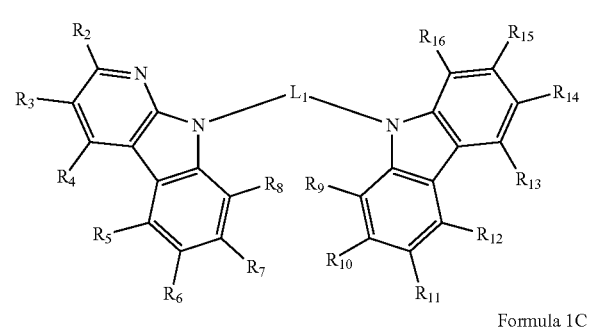

Formula 1C
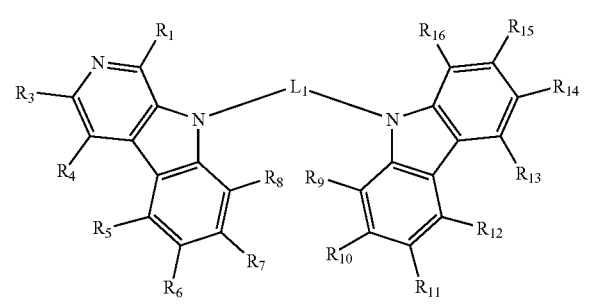

Formula 1D
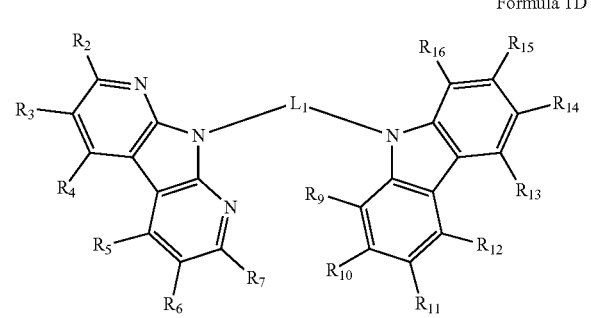

Formula 1E
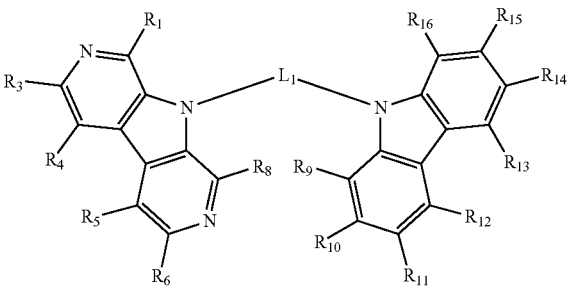

wherein, in Formulae 1A to 1E, $L_1$ is selected from a phenylene group, a pyridinylene group, a pyrimidinylene group, and a triazinylene group;

$R_1$ to $R_{16}$ may be each independently selected from $R_{ET}$, a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group, and a dibenzothiophenyl group; and a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group and a dibenzothiophenyl group, each substituted with at least one selected from a deuterium, —F, —Cl, —Br, —I, a hydroxyl group, a cyano group, a nitro group, a $C_1$-$C_{20}$ alkyl group, a phenyl group, a naphthyl group, a pyridinyl group, a pyrimidinyl group, and a triazinyl group.

At least one selected from $R_1$ to $R_{16}$ is $R_{ET}$; and $R_{ET}$ is a group represented by any one selected from Formulae 2-1 to 2-8 below:

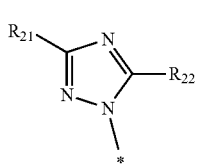
2-1

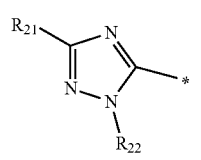
2-2

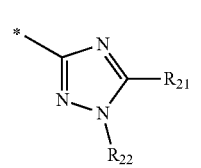
2-3

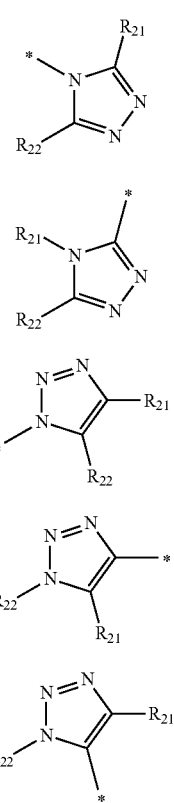

wherein in Formulae 2-1 to 2-8, $R_{21}$ and $R_{22}$ may be each independently selected from a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, an n-pentyl group, an n-hexyl group, a methoxy group, an ethoxy group, an n-propoxy group, an iso-propoxy group, an n-butoxy group, a tert-butoxy group, a cyclopentyl group, a cyclohexyl group, a phenyl group, a naphthyl group, a fluorenyl group, a pyridinyl group, a pyrimidinyl group, a pyridazinyl group, and a triazinyl group; and a phenyl group, a naphthyl group, a fluorenyl group, a pyridinyl group, a pyrimidinyl group, a pyridazinyl group, and a triazinyl group, each substituted with at least one selected from a deuterium, —F, —Cl, —Br, —I, a hydroxyl group, a cyano group, a nitro group, a $C_1$-$C_{20}$ alkyl group, a phenyl group, a naphthyl group, a pyridinyl group, a pyrimidinyl group, and a triazinyl group.

* indicates a binding site to a neighboring atom.

In some embodiments, $R_1$ to $R_{13}$, $R_{15}$, and $R_{16}$ in Formulae 1A to 1E may be each independently selected from a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group, and a dibenzothiophenyl group; and a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group and a dibenzothiophenyl group, each substituted with at least one selected from a deuterium, —F, —Cl, —Br, —I, a hydroxyl group, a cyano group, a nitro group, a $C_1$-$C_{20}$ alkyl group, a phenyl group, a naphthyl group, a pyridinyl group, a pyrimidinyl group, and a triazinyl group;

$R_{14}$ may be $R_{ET}$, but is not limited thereto.

In some embodiments, $R_1$ to $R_9$, $R_{11}$ to $R_{13}$, $R_{15}$, and $R_{16}$ in Formulae 1A to 1E may be each independently selected from a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group, and a dibenzothiophenyl group; and a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group and a dibenzothiophenyl group, each substituted with at least one selected from a deuterium, —F, —Cl, —Br, —I, a hydroxyl group, a cyano group, a nitro group, a $C_1$-$C_{20}$ alkyl group, a phenyl group, a naphthyl group, a pyridinyl group, a pyrimidinyl group, and a triazinyl group;

$R_{10}$ may be a hydrogen;

$R_{14}$ may be $R_{ET}$, but is not limited thereto.

In some embodiments, $R_1$ to $R_9$, $R_{11}$ to $R_{13}$, $R_{15}$, and $R_{16}$ in Formulae 1A to 1E may be each independently selected from a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group, and a dibenzothiophenyl group; and a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group and a dibenzothiophenyl group, each substituted with at least one selected from a deuterium, —F, —Cl, —Br, —I, a hydroxyl group, a cyano group, a nitro group, a $C_1$-$C_{20}$ group, a phenyl group, a naphthyl group, a pyridinyl group, a pyrimidinyl group, and a triazinyl group;
$R_{10}$ may be a hydrogen;
$R_{14}$ may be represented by a group represented by any one of Formulae 5-1 to 5-24 below, but embodiments are not limited thereto:
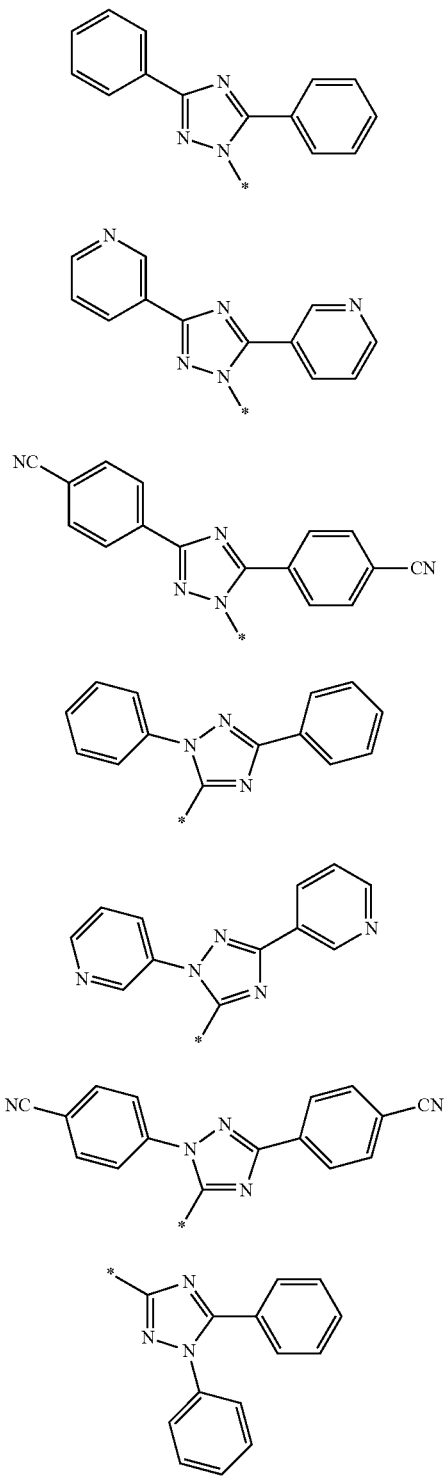
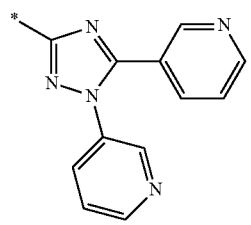
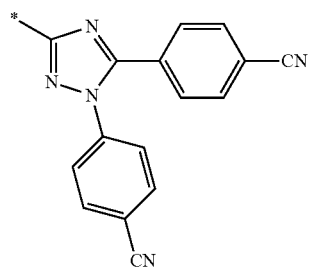
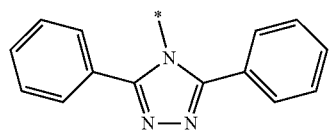
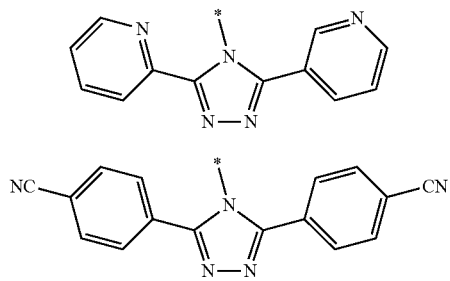
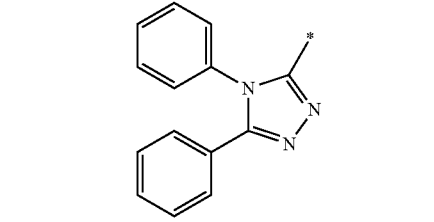
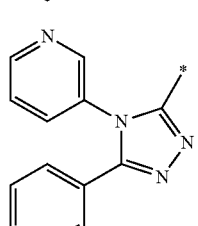
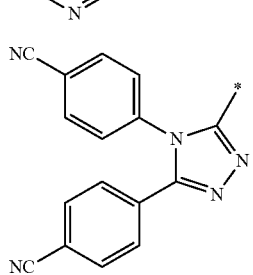

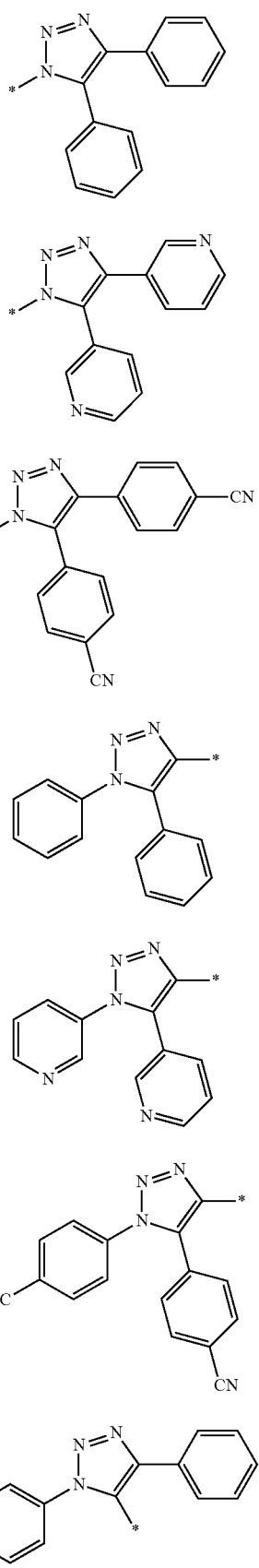
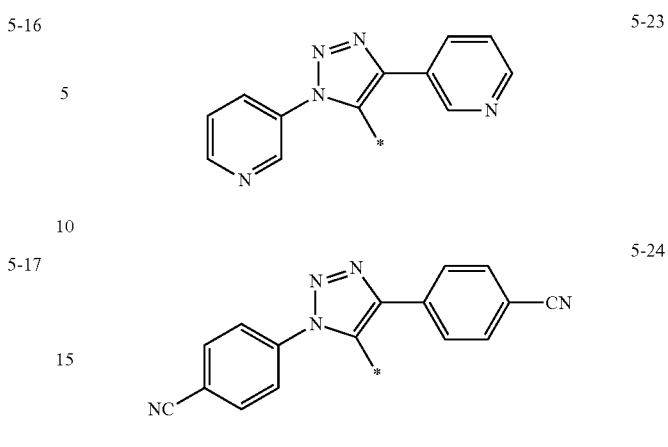
wherein in Formulae 5-1 to 5-24,
* indicates a binding site to a neighboring atom.
In some embodiments, the condensed cyclic compound may be represented by any one selected from Formula 1-1 to 1-9:
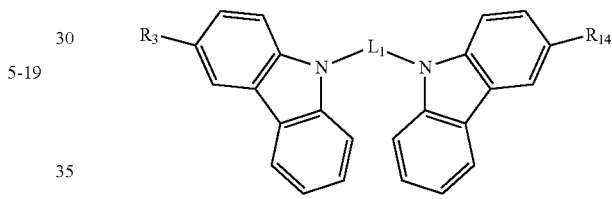
Formula 1-1
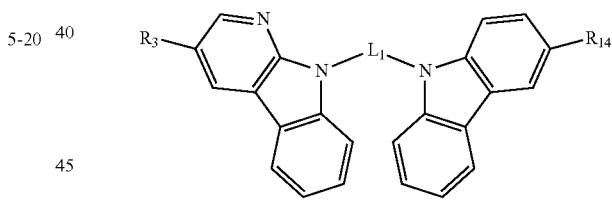
Formula 1-2
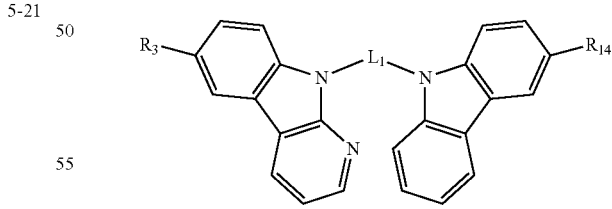
Formula 1-3
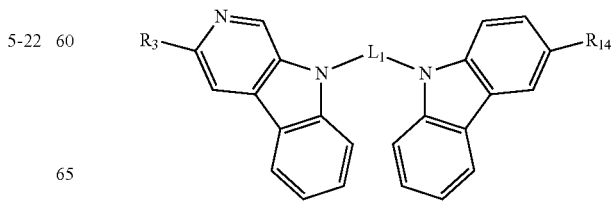
Formula 1-4

-continued

Formula 1-5
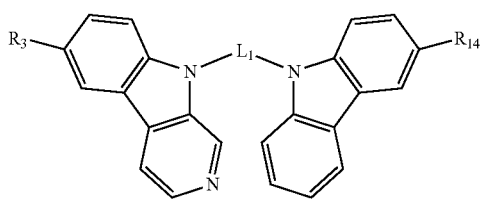

Formula 1-6
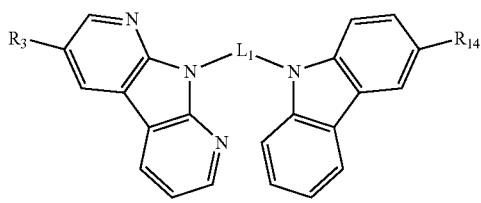

Formula 1-7
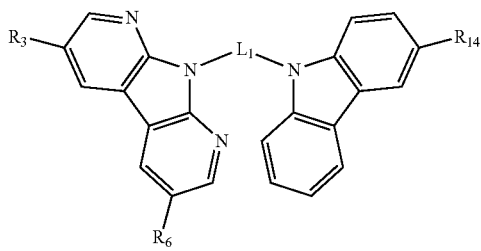

Formula 1-8
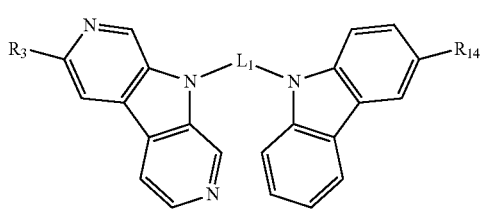

Formula 1-9
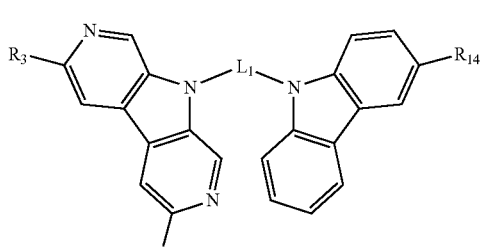

wherein in Formulae 1-1 to 1-9, $L_1$ is selected from a phenylene group, a pyridinylene group, a pyrimidinylene group, and a triazinylene group;

$R_3$, $R_6$, and $R_{14}$ may be each independently selected from $R_{ET}$, a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group, and a dibenzothiophenyl group; and a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group and a dibenzothiophenyl group, each substituted with at least one selected from a deuterium, —F, —Cl, —Br, —I, a hydroxyl group, a cyano group, a nitro group, a $C_1$-$C_{20}$ alkyl group, a phenyl group, a naphthyl group, a pyridinyl group, a pyrimidinyl group, and a triazinyl group;

at least one selected from $R_3$, $R_6$, and $R_{14}$ may be $R_{ET}$;

$R_{ET}$ is represented by any one of Formulae 2-1 to 2-8:

2-1
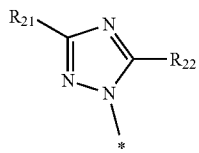

2-2
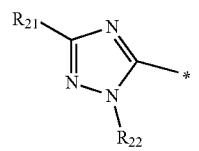

2-3
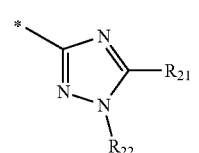

2-4
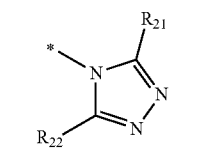

2-5
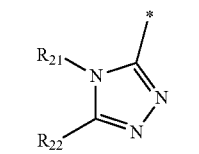

2-6
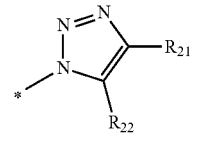

2-7
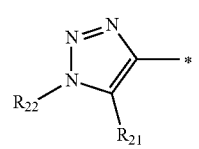

-continued

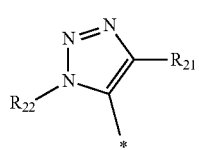
2-8 wherein in Formulae 2-1 to 2-8, $R_{21}$ and $R_{22}$ may be each independently selected from a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, an n-pentyl group, an n-hexyl group, a methoxy group, an ethoxy group, an n-propoxy group, an iso-propoxy group, an n-butoxy group, a tert-butoxy group, a cyclopentyl group, a cyclohexyl group, a phenyl group, a naphthyl group, a fluorenyl group, a pyridinyl group, a pyrimidinyl group, a pyridazinyl group, and a triazinyl group; and a phenyl group, a naphthyl group, a fluorenyl group, a pyridinyl group, a pyrimidinyl group, a pyridazinyl group, and a triazinyl group, each substituted with at least one selected from a deuterium, —F, —Cl, —Br, —I, a hydroxyl group, a cyano group, a nitro group, a $C_1$-$C_{20}$ alkyl group, a phenyl group, a naphthyl group, a pyridinyl group, a pyrimidinyl group, and a triazinyl group.

* indicates a binding site to a neighboring atom.

For example, $R_{ET}$ in Formula 1-1 to 1-9 may be selected from Formulae 5-1 to 5-24 below, but embodiments are not limited thereto:

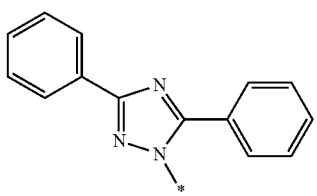
5-1

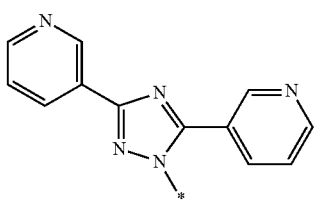
5-2

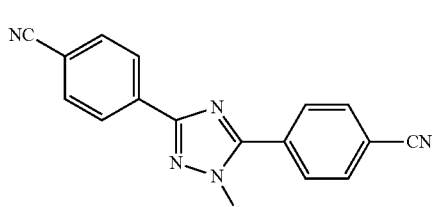
5-3

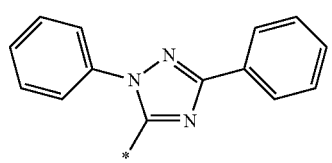
5-4

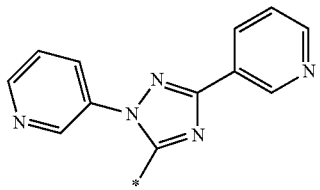
5-5

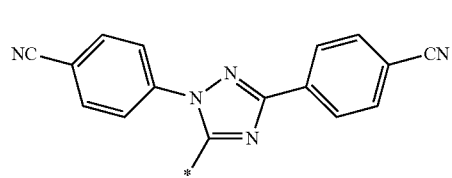
5-6

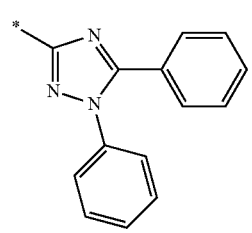
5-7

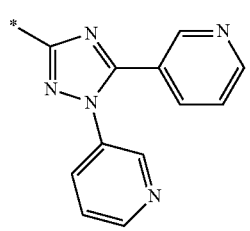
5-8

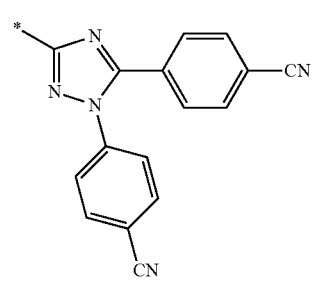
5-9

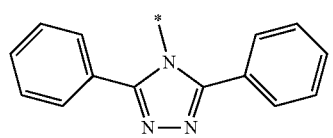
5-10

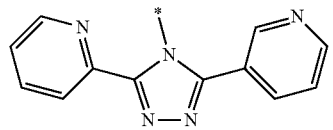
5-11

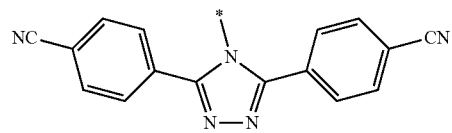
5-12

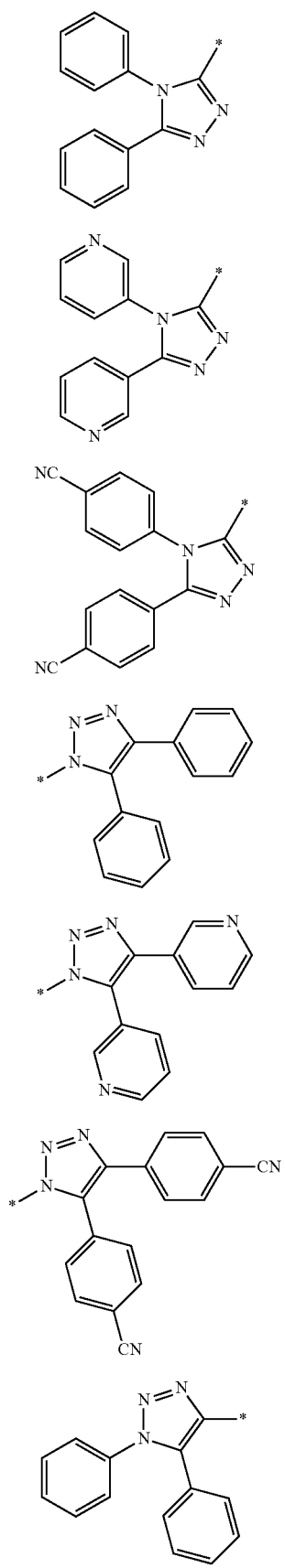
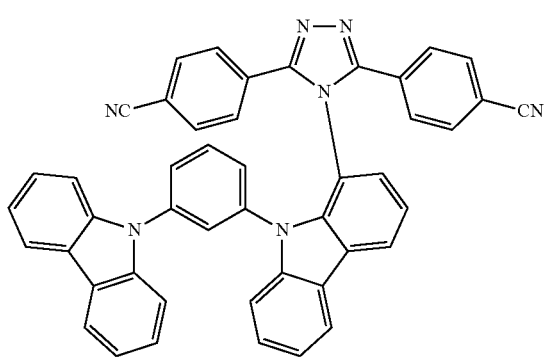
wherein in Formulae 5-1 to 5-24,
* indicates a binding site to a neighboring atom.
In some embodiments, the condensed cyclic compound may be selected from Compounds 1 to 107 below, but are not limited thereto:

2
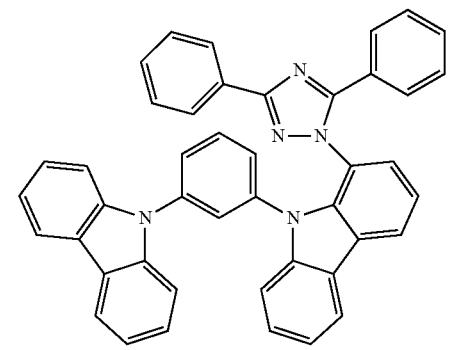
3
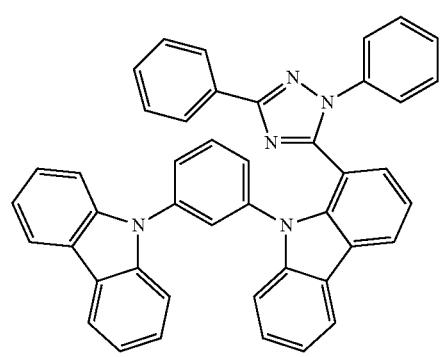
4
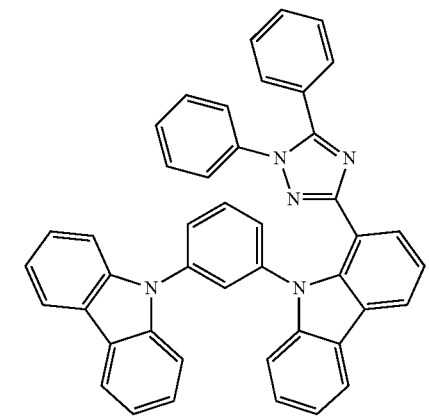
5
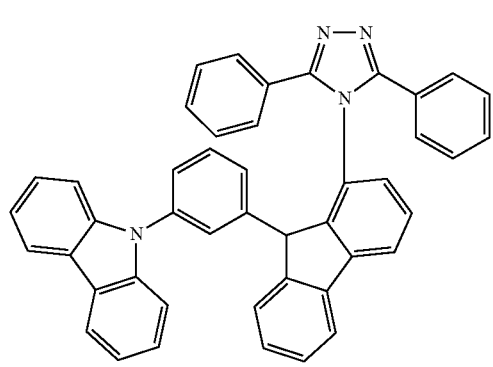
6
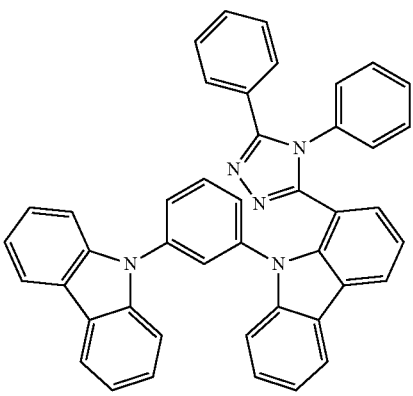
7
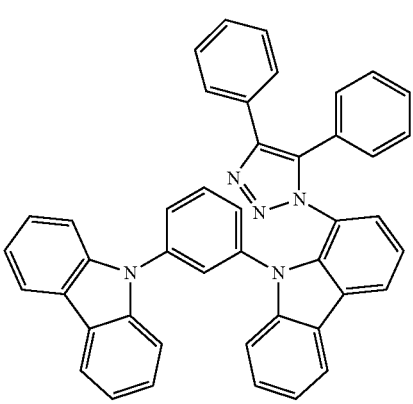
8
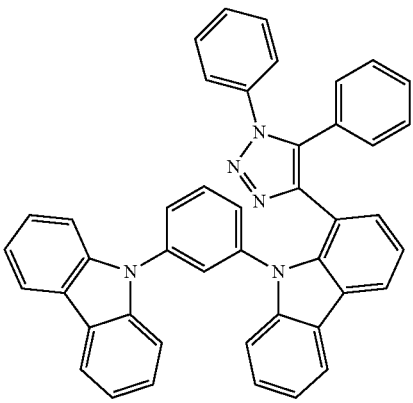
9
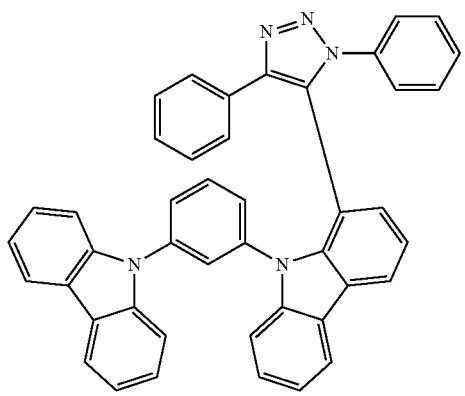

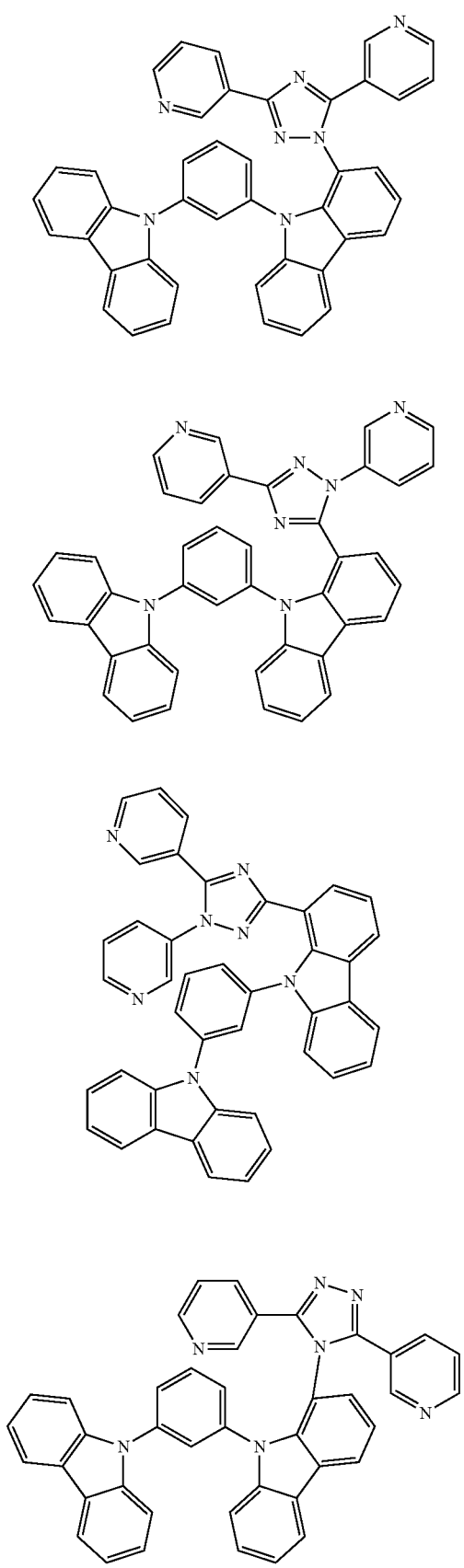
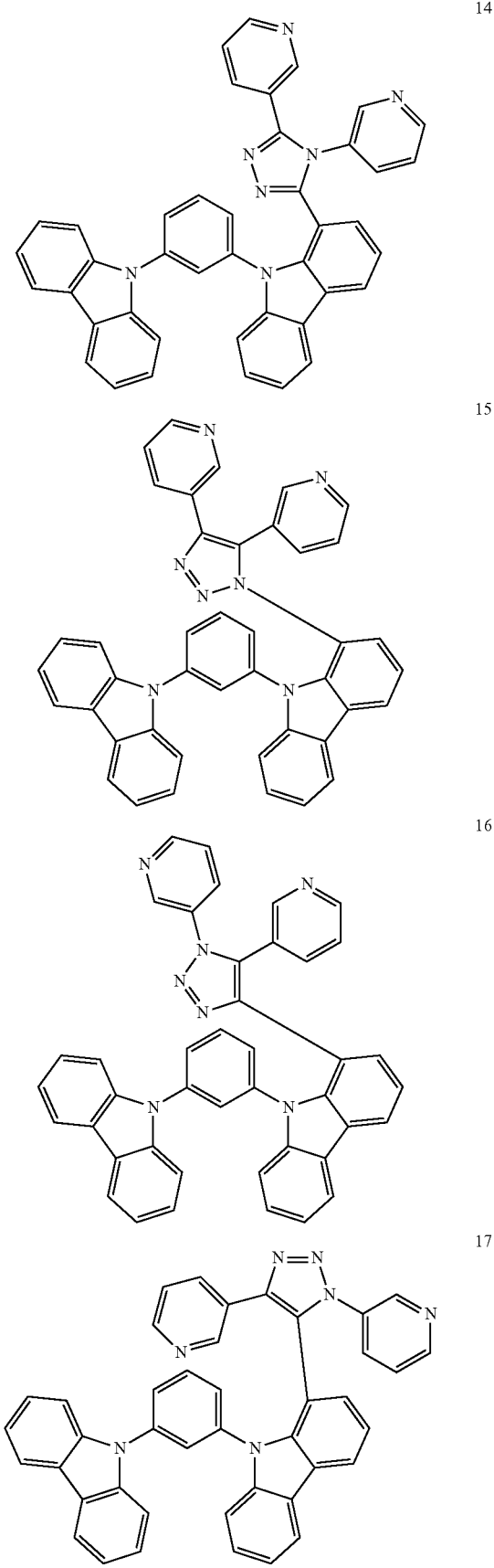

-continued
18
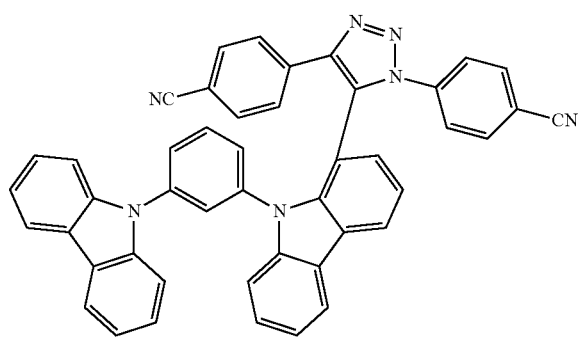
19
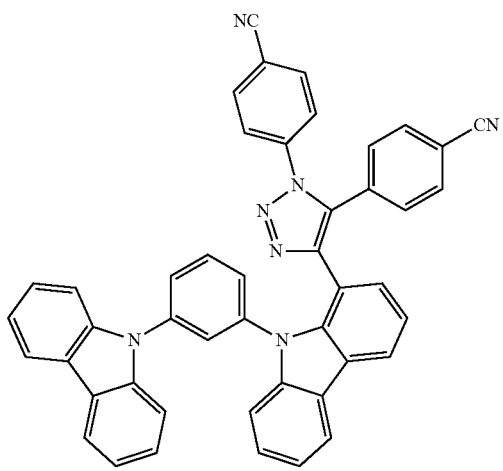
20
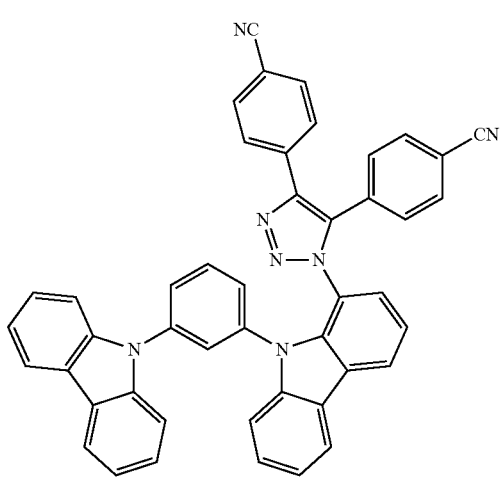
-continued
21
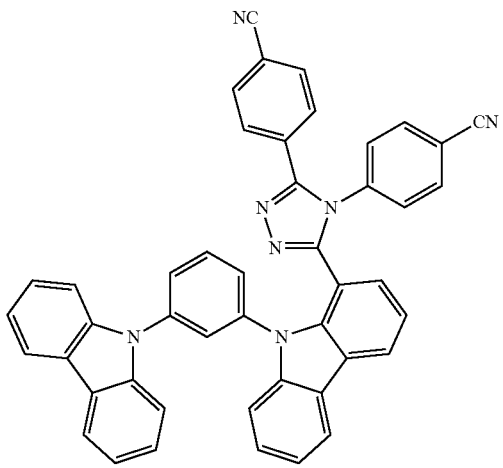
22
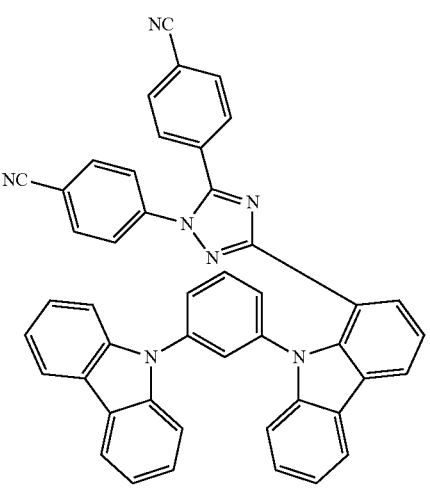
23
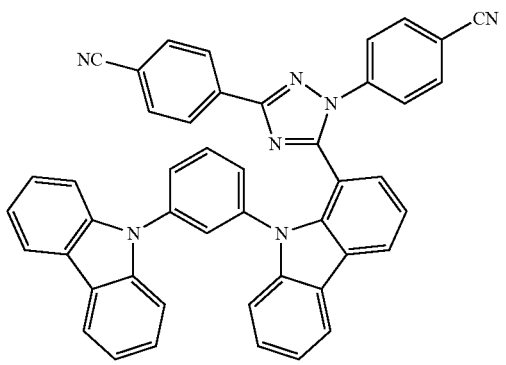

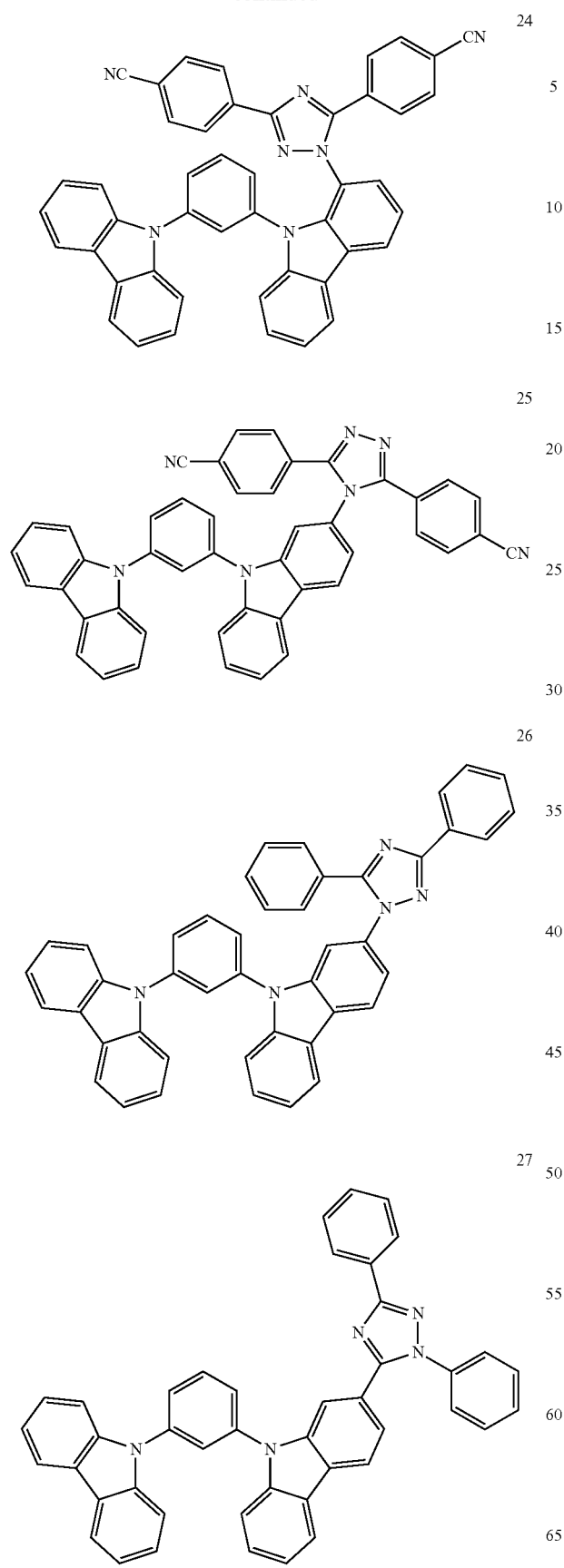
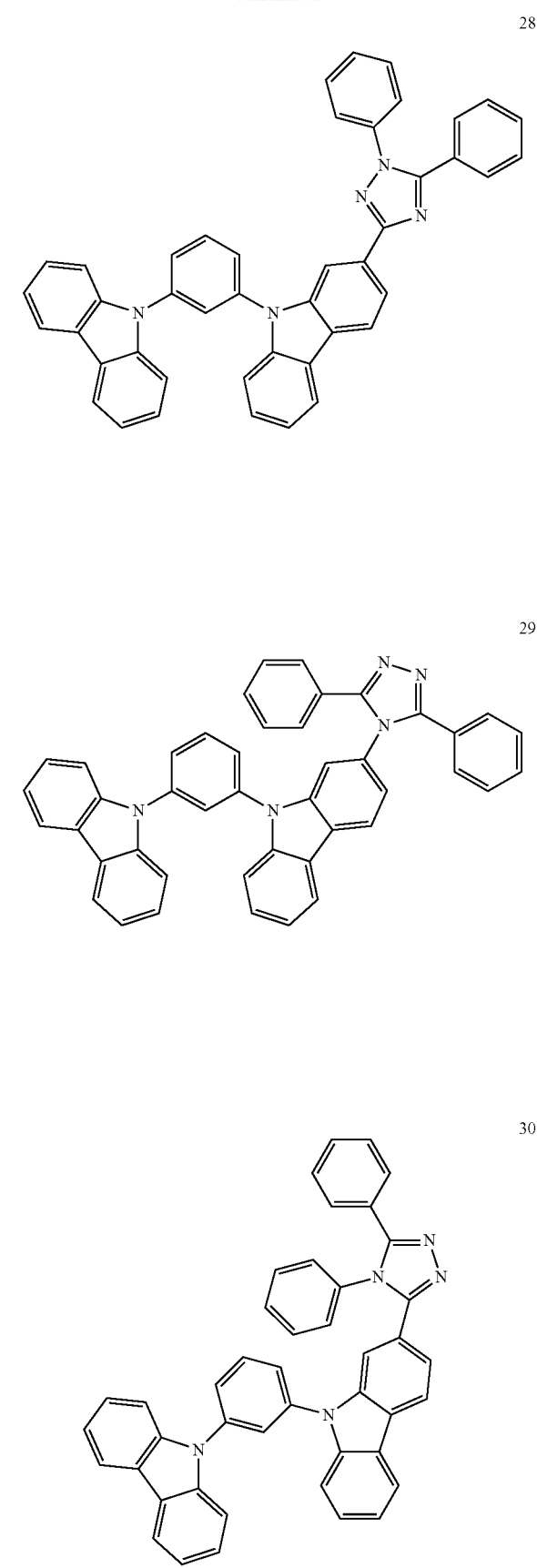

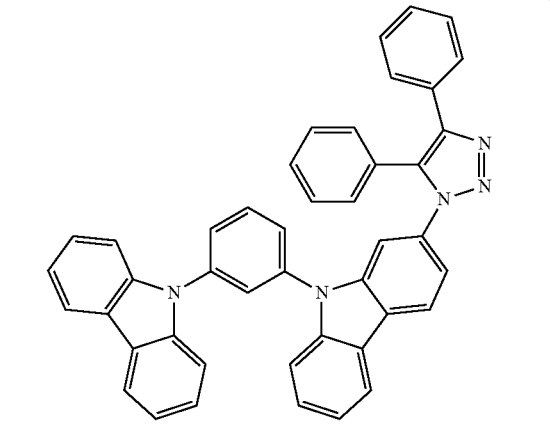
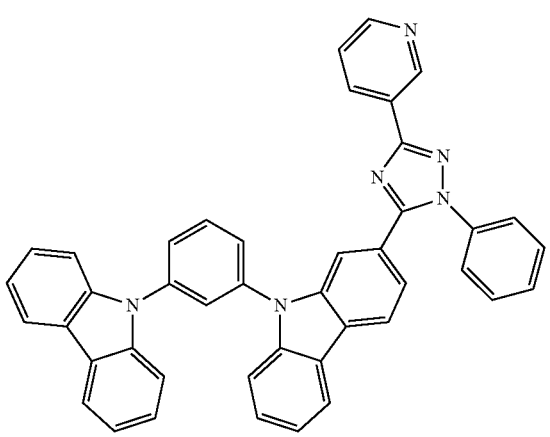
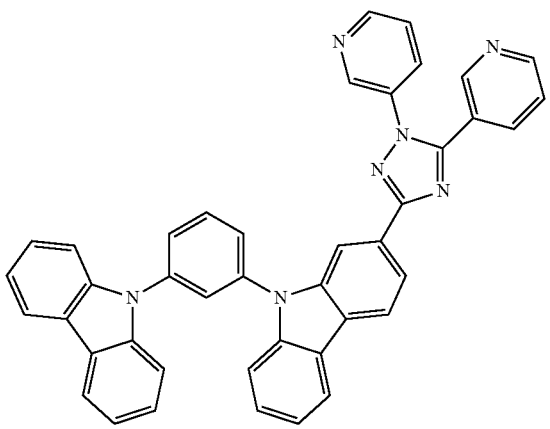
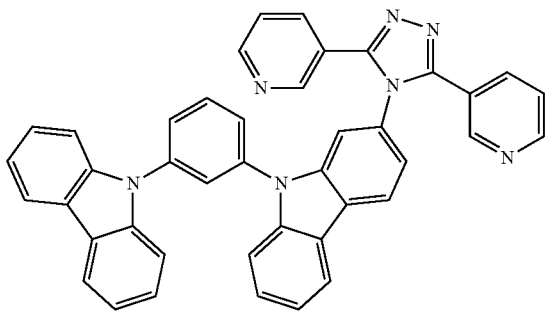
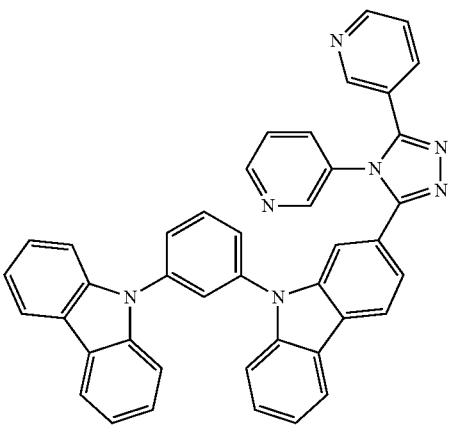

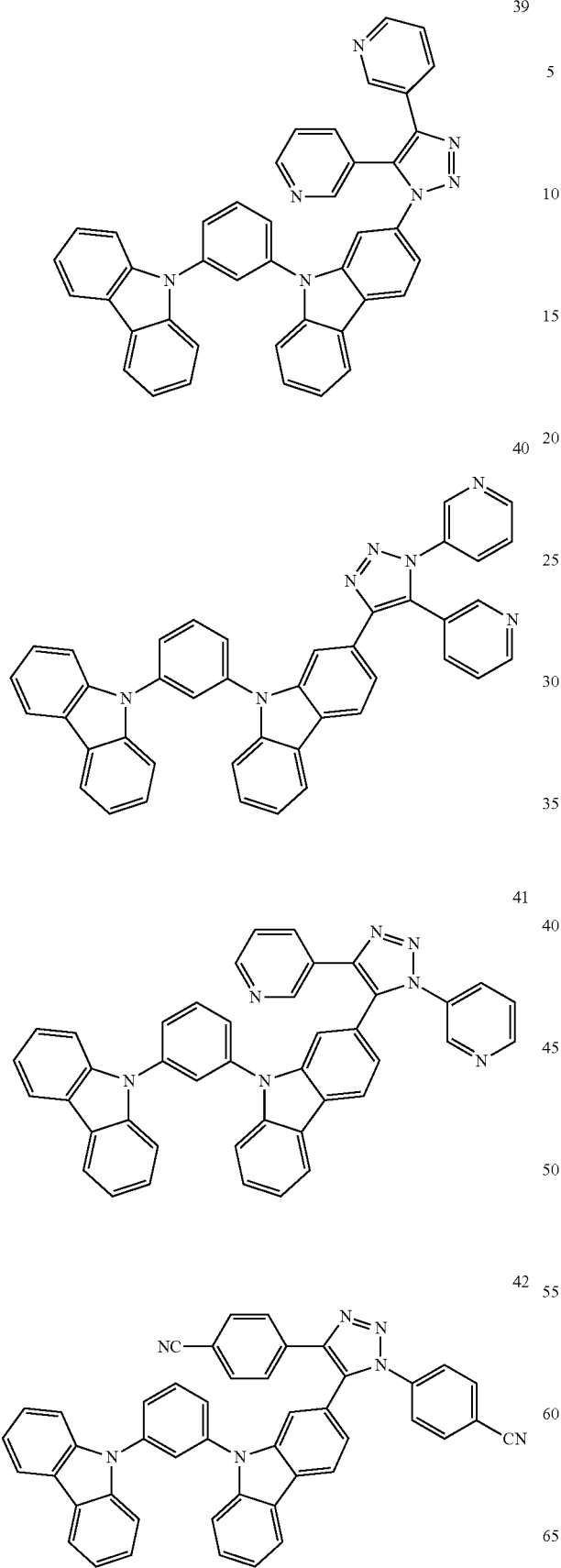
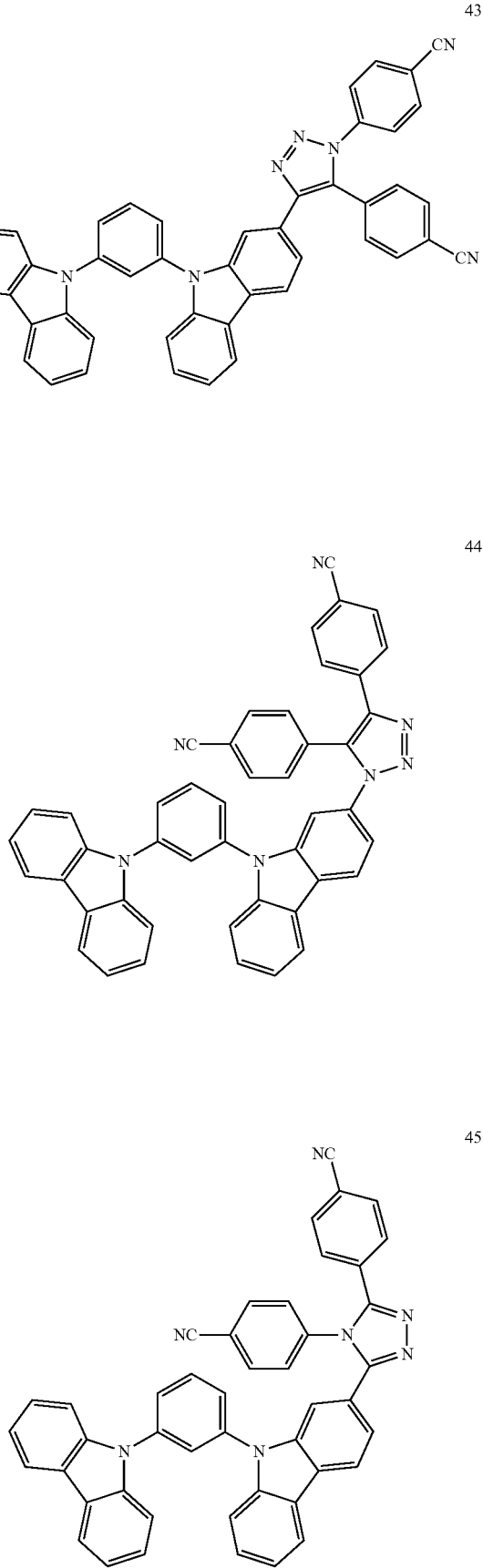

47
-continued
46
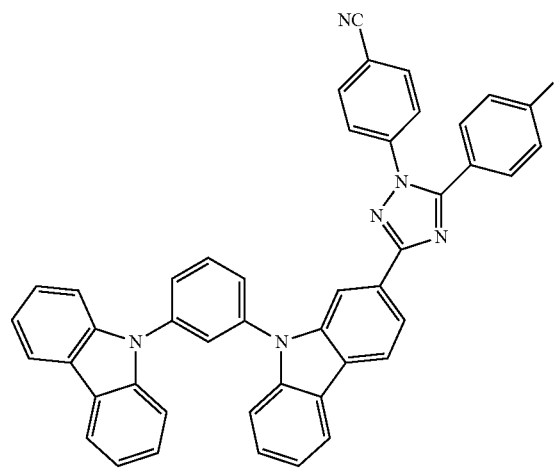
47
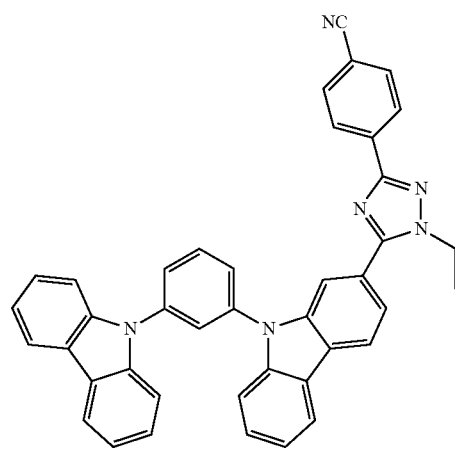
48
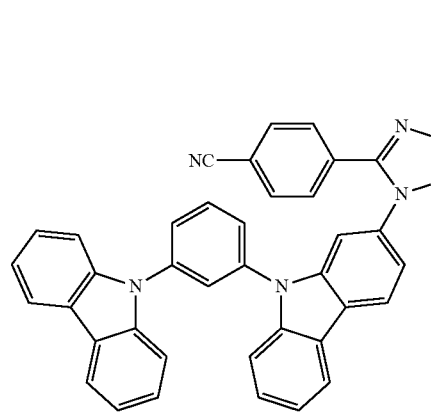
48
-continued
49
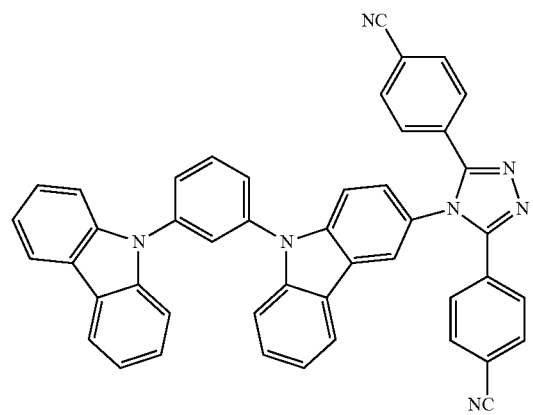
50
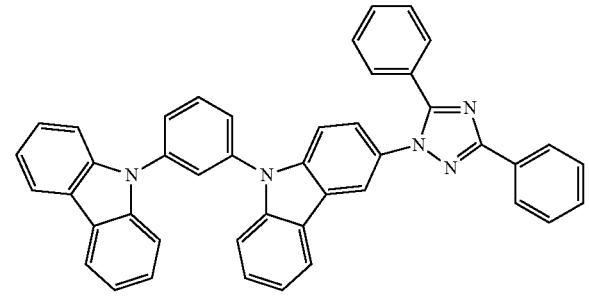
51
52
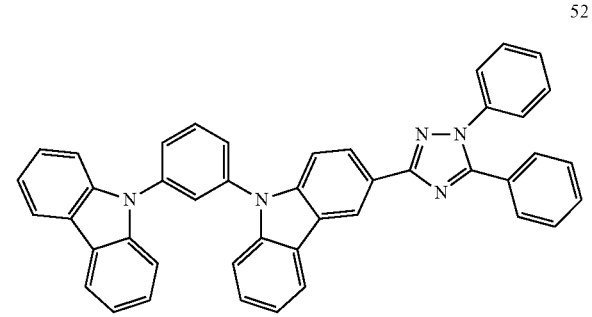

-continued
53
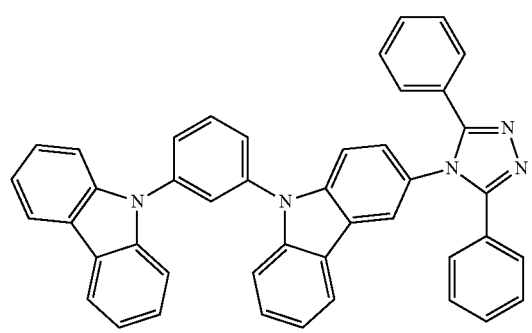
54
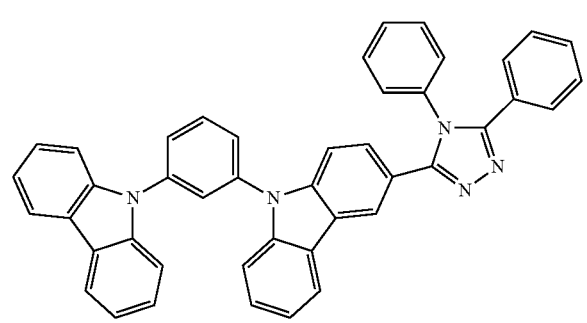
55
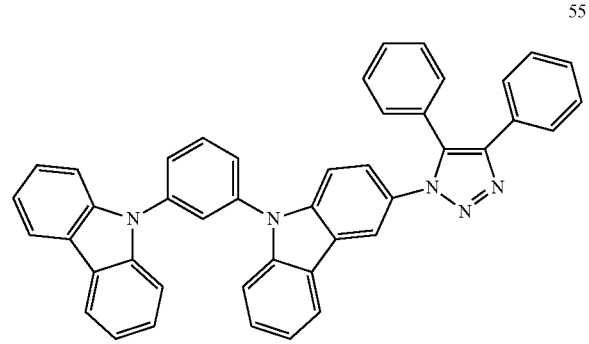
56
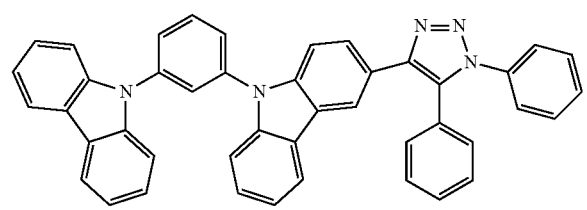
57
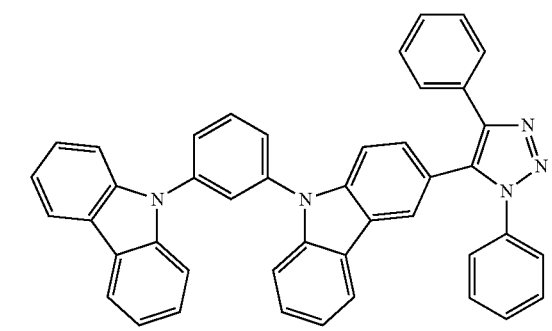
-continued
58
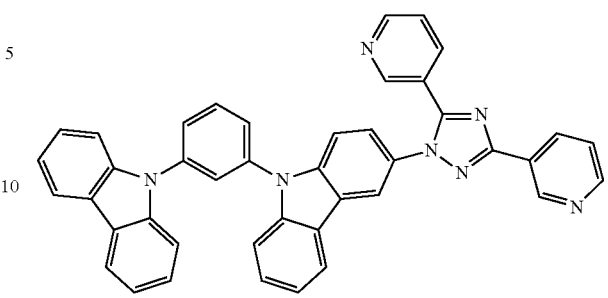
59
60
61
62

51
-continued
63
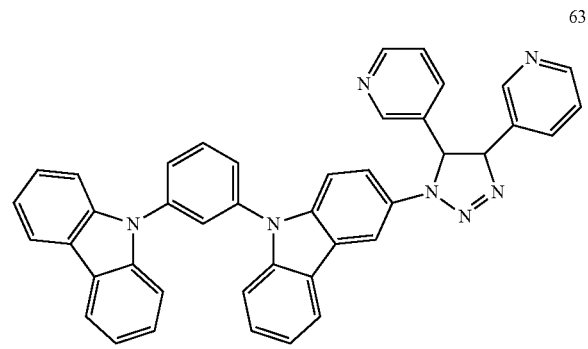
64
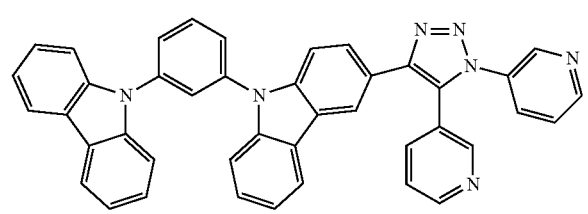
65
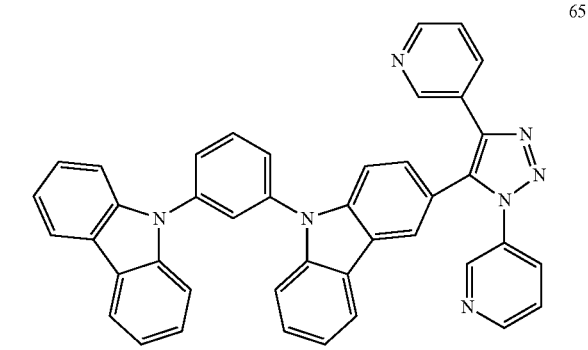
66
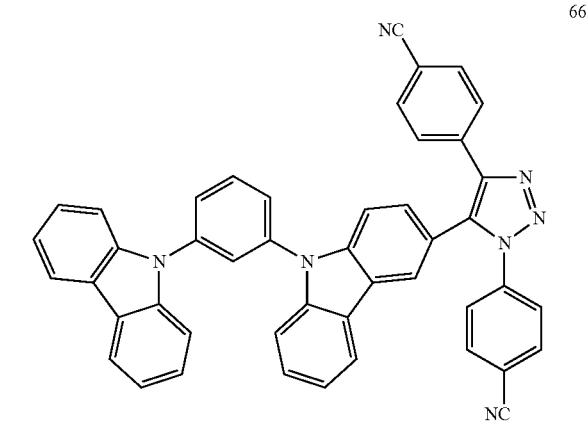
67
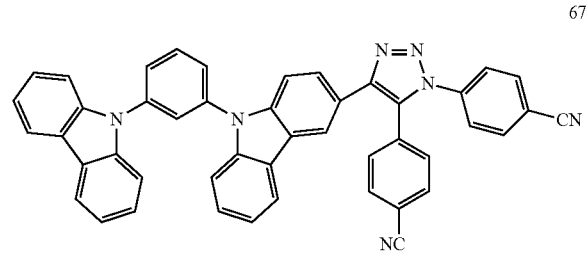
52
-continued
68
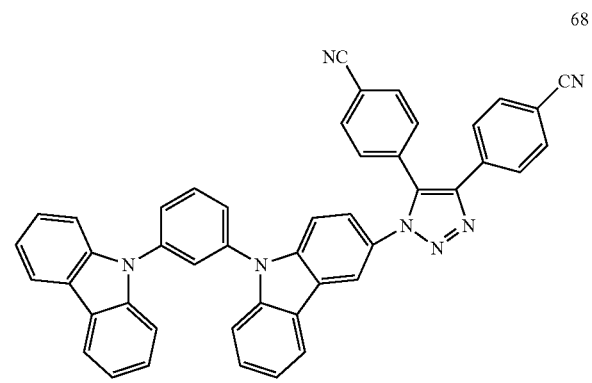
69
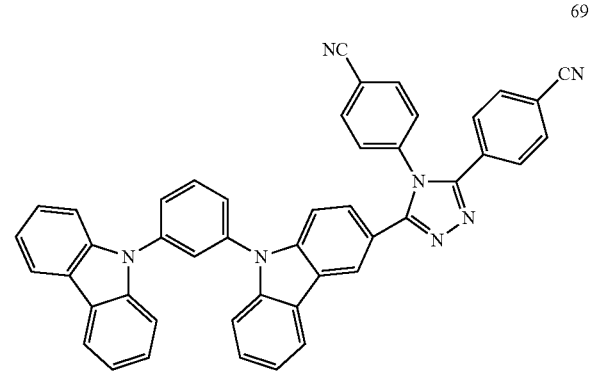
70
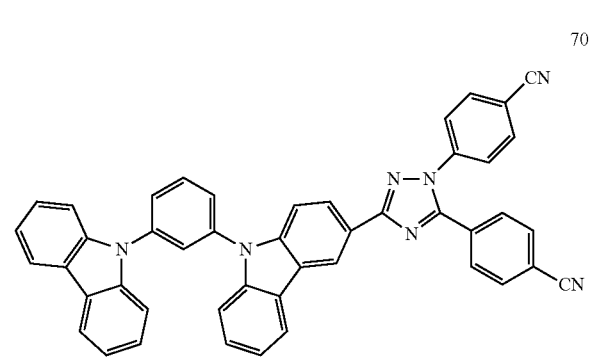
71
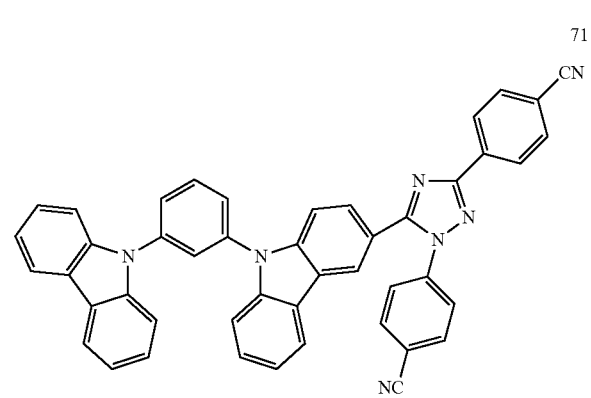

-continued
72
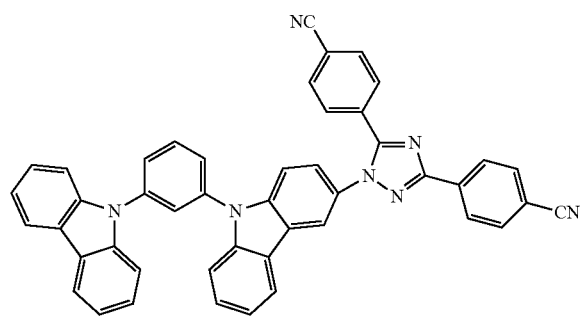
73
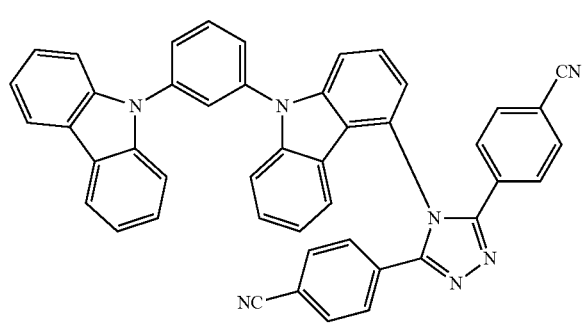
74
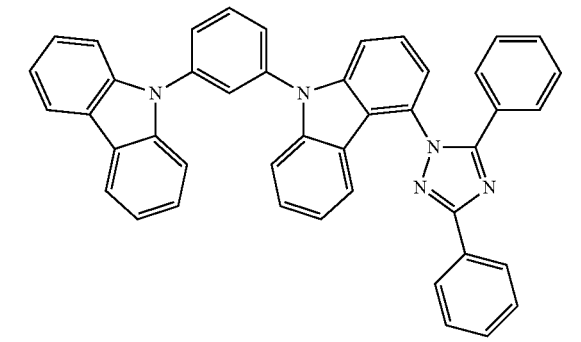
75
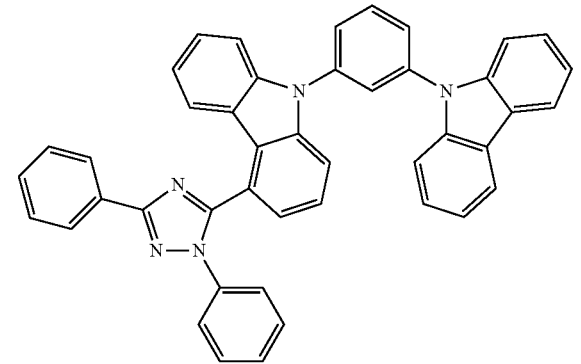
-continued
76
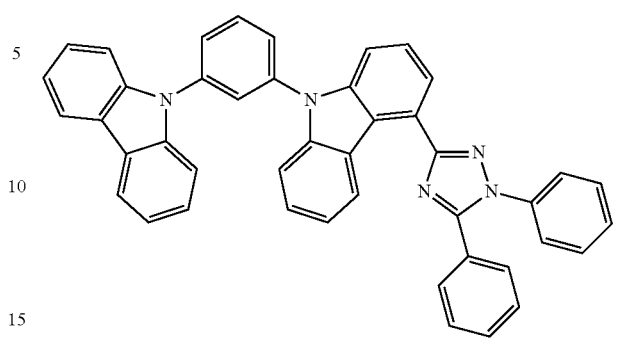
77
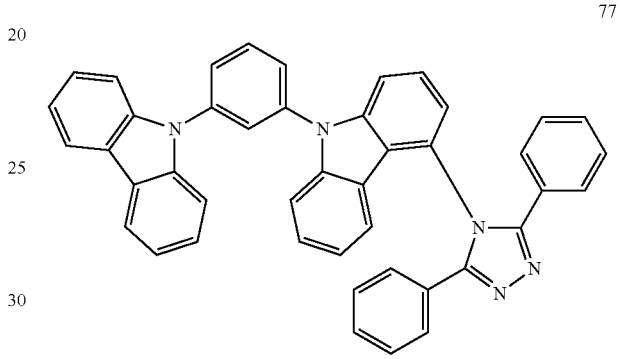
78
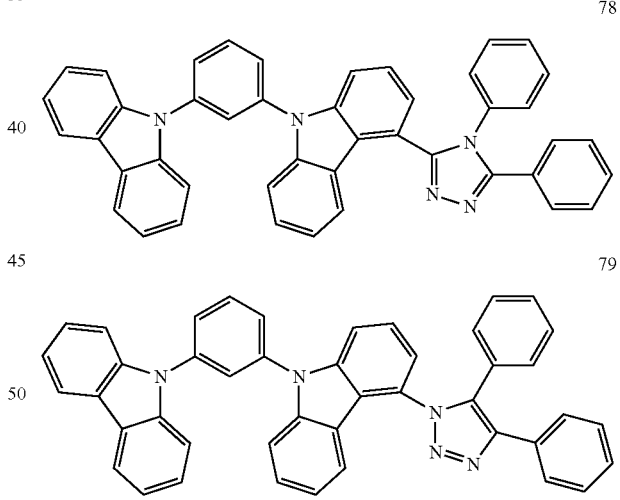
79
80
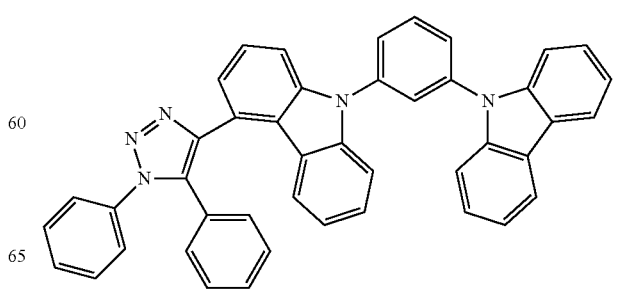

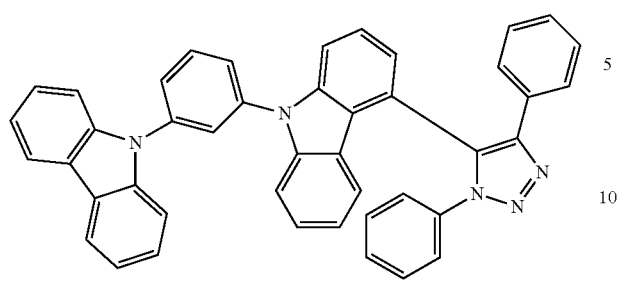
81
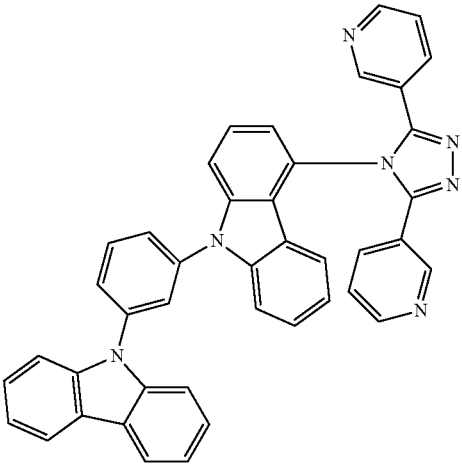
85
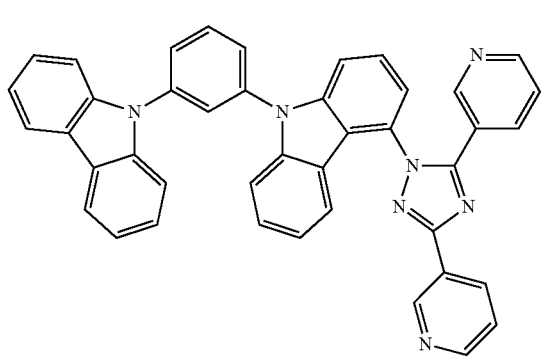
82
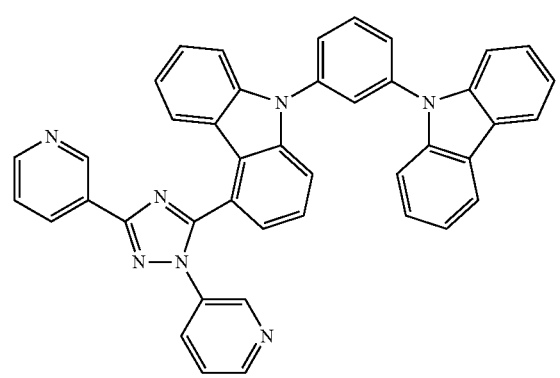
83
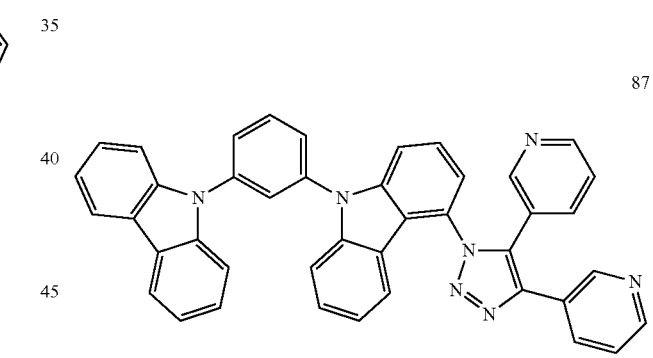
86
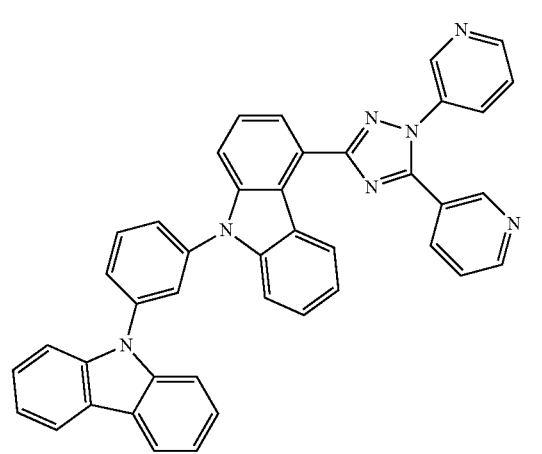
84
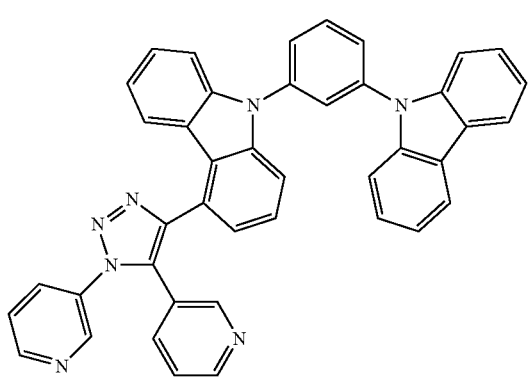
87
88

89
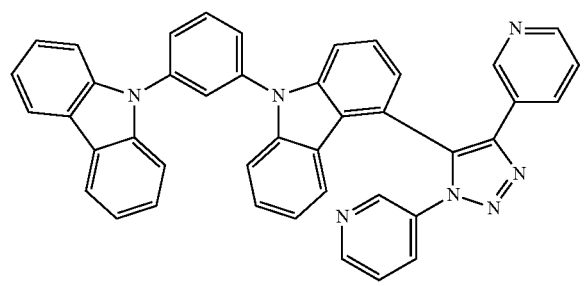
90
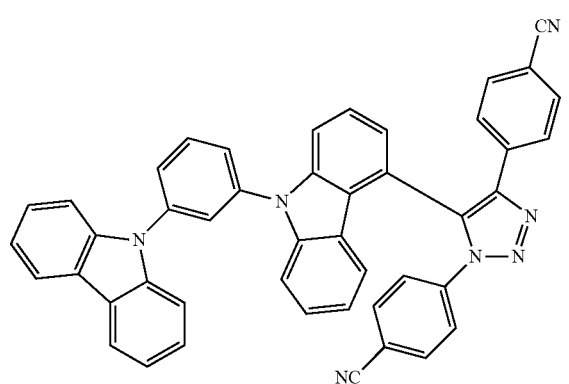
91
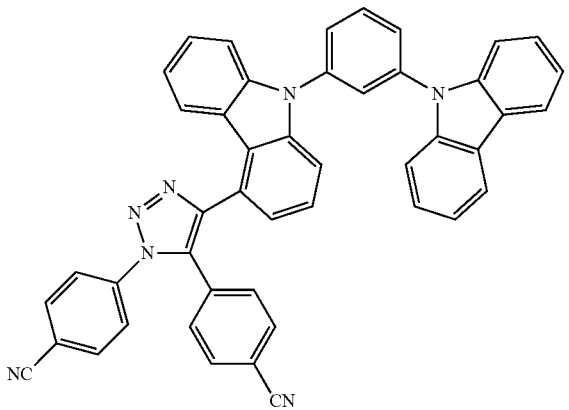
92
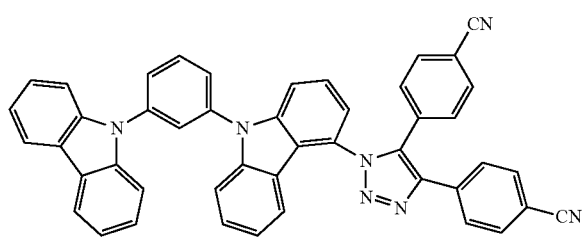
93
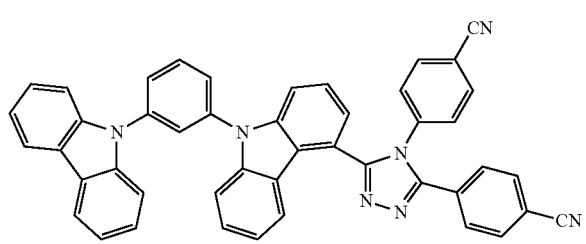
94
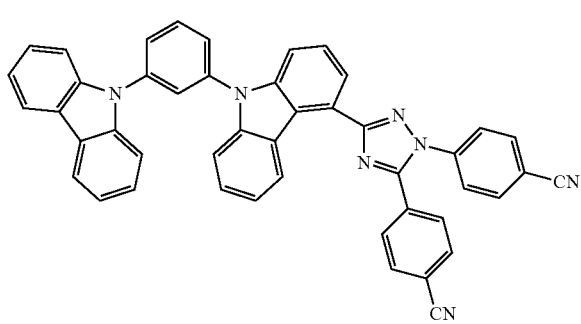
95
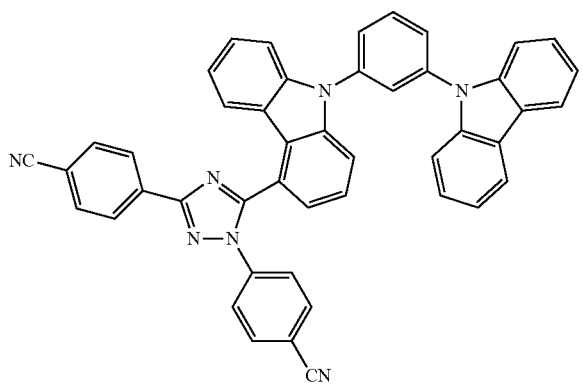
96
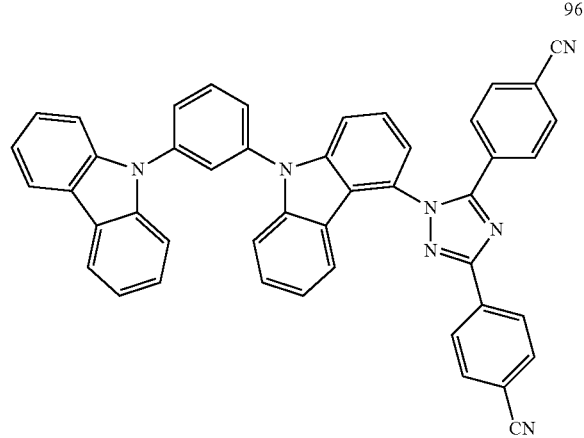

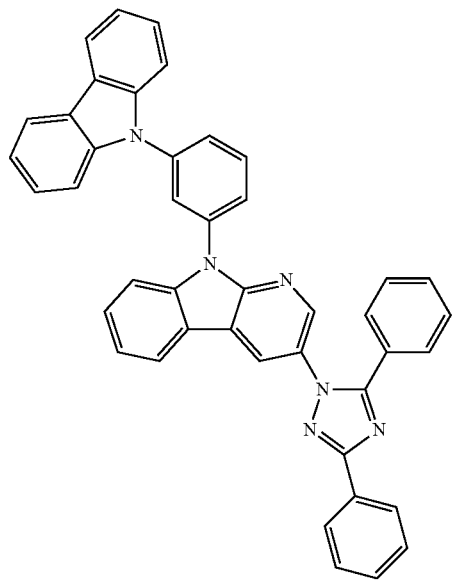
97
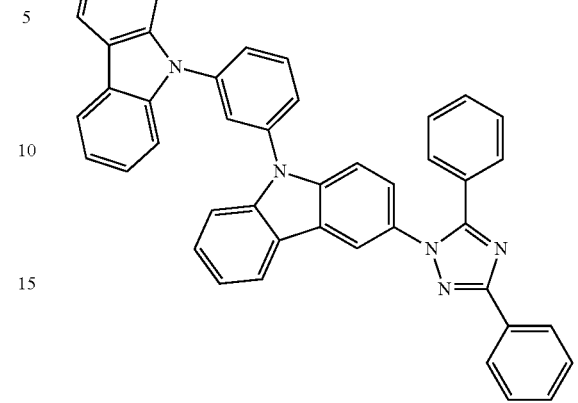
100
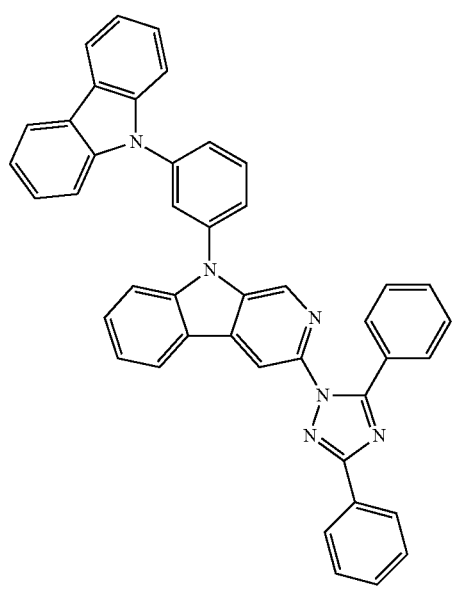
98
101
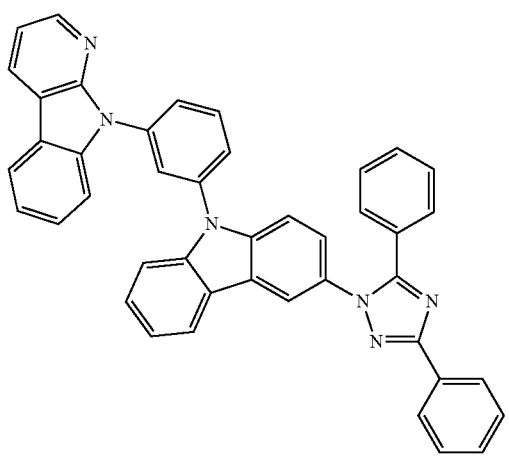
99
102

103 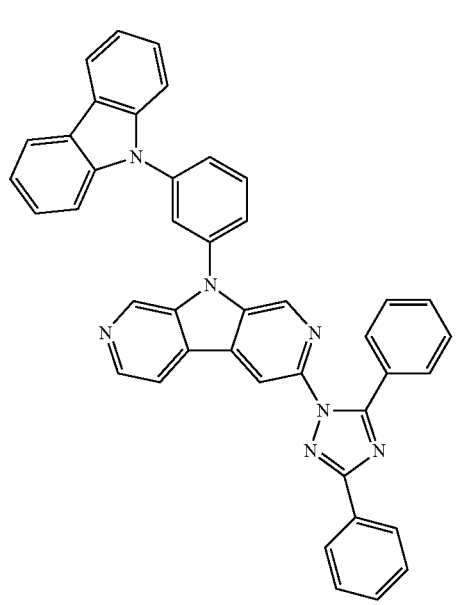
104 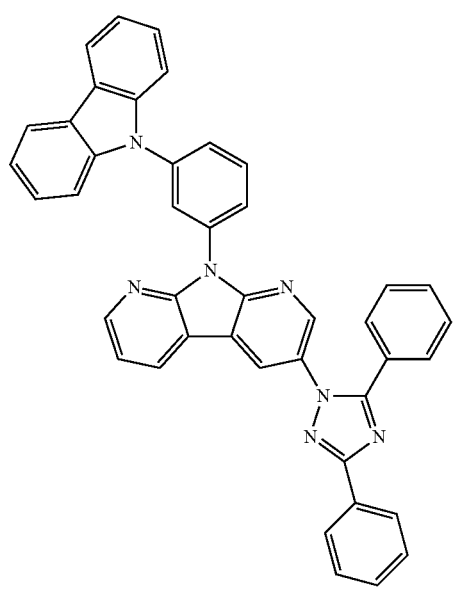
105 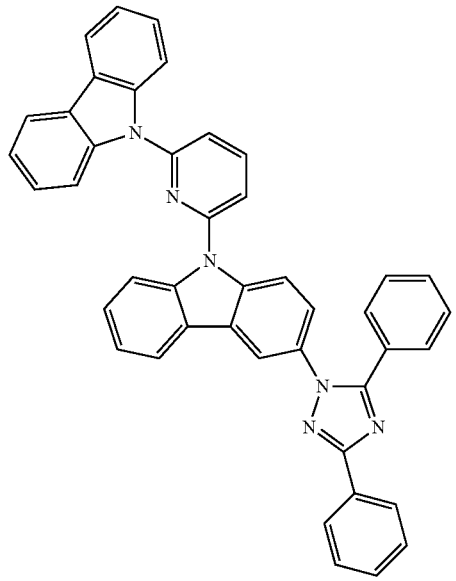
106 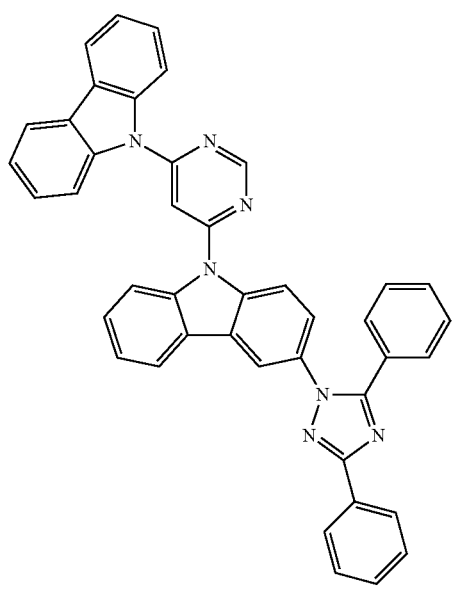

-continued

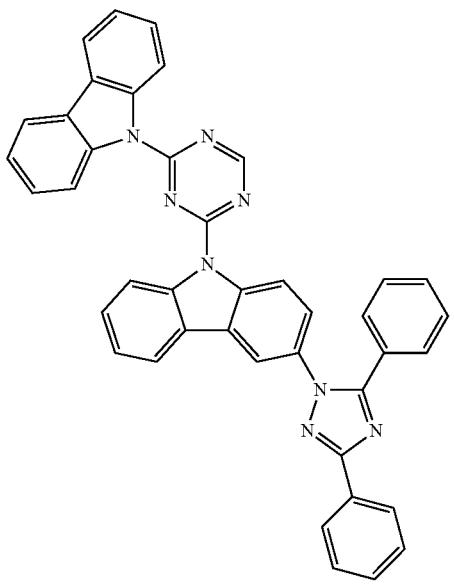

107

The condensed cyclic compound represented by Formula 1 may have a triplet energy of 2.5 electron volt (eV) to 3.3 eV.

The condensed cyclic compound represented by Formula 1 may have a glass transition temperature (Tg) of 100° C. to 200° C.

The condensed cyclic compound represented by Formula 1 may have a decomposition temperature (Td) of 300° C. to 450° C.

The structure of the condensed cyclic compound represented by Formula 1 may be controlled such that its conjugation length is increased only to such a level that the structure of "carbazolyl-$L_1$-carbazolyl-triazolyl" is included in its conjugation segment. Thus, the condensed cyclic compound represented by Formula 1 may have a high triplet energy. Accordingly, efficiency of an organic light-emitting device including the condensed cyclic compound may be improved.

The condensed cyclic compound represented by Formula 1 may have at least one triazole group as a substituent. As illustrated in Formula 1', a conjugation length of the condensed cyclic compound represented by Formula 1 may vary according to whether $R_{21}$ and $R_{22}$, which are substituents of a triazole group, are involved in the conjugation:

Formula 1'

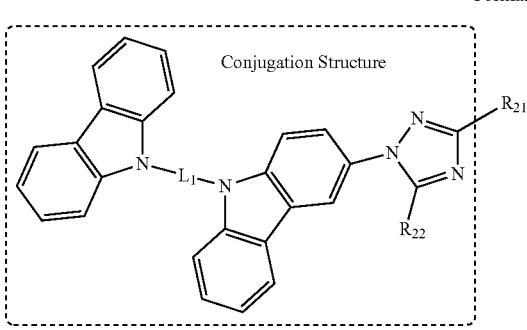

The condensed cyclic compound represented by Formula 1 includes two carbazolyl groups, as illustrated in Formula 1''. The condensed cyclic compound represented by Formula 1 may have high thermal stability and high charge mobility due to characteristics of substituents of the carbazolyl group.

Formula 1''

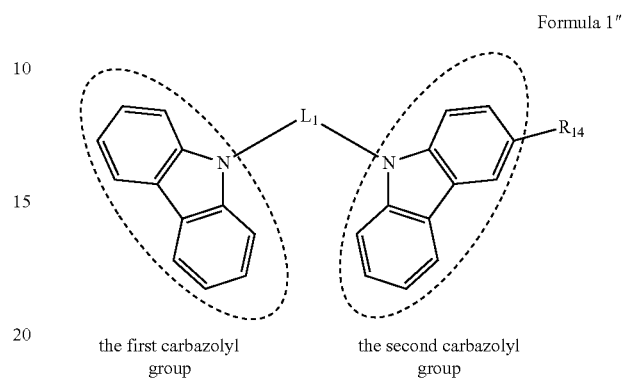

the first carbazolyl group      the second carbazolyl group

The condensed cyclic compound represented by Formula 1 may have a molecular weight of 550 grams per mole (g/mol) or more, for example, a molecular weight of 550 to 700 g/mol. However, embodiments are not limited thereto. When the molecular weight satisfies the conditions described above, the condensed cyclic compound represented by Formula 1 may have a Td that is suitable for deposition. When the molecular weight satisfies the conditions described above, the condensed cyclic compound represented by Formula 1 may have a sufficient Tg. Accordingly, an organic light-emitting device including the condensed cyclic compound represented by Formula 1 may have improved thermal stability.

A molecular weight, the highest occupied molecular orbital (HOMO) energy level, the lowest unoccupied molecular orbital (LUMO) energy level, and the triplet energy level $T_1$ of some of the condensed cyclic compound represented by Formula 1 was evaluated by using a Gaussian 09 program accompanied with optimization of molecular structure according to B3LYP-based density functional theory (DFT). The results thereof are shown in Table 1 below.

TABLE 1

|    | HOMO (eV) | LUMO (eV) | $T_1$ (eV) | Molecular weight |
|----|-----------|-----------|------------|------------------|
| 1  | −5.627    | −2.257    | 2.699      | 677              |
| 2  | −5.336    | −1.144    | 3.086      | 627              |
| 3  | −5.324    | −1.153    | 3.079      | 627              |
| 4  | −5.318    | −1.166    | 3.086      | 627              |
| 5  | −5.291    | −1.265    | 3.005      | 627              |
| 6  | −5.47     | −1.044    | 3.125      | 629              |
| 7  | −5.242    | −1.066    | 2.908      | 629              |
| 8  | −5.437    | −1.155    | 3.137      | 627              |
| 9  | −5.321    | −1.123    | 3.113      | 627              |
| 10 | −5.398    | −1.448    | 3.104      | 629              |
| 11 | −5.411    | −1.429    | 3.076      | 629              |
| 12 | −5.348    | −1.64     | 3.049      | 629              |
| 13 | −5.364    | −1.523    | 3.049      | 629              |
| 14 | −5.403    | −1.396    | 3.116      | 629              |
| 15 | −5.282    | −1.302    | 2.902      | 631              |
| 16 | −5.535    | −1.562    | 3.131      | 629              |
| 17 | −5.421    | −1.432    | 3.106      | 629              |
| 18 | −5.576    | −2.148    | 2.918      | 677              |
| 19 | −5.688    | −2.297    | 2.927      | 677              |
| 20 | −5.465    | −1.956    | 2.871      | 679              |
| 21 | −5.7      | −2.203    | 2.978      | 677              |

TABLE 1-continued

|  | HOMO (eV) | LUMO (eV) | T₁ (eV) | Molecular weight |
|---|---|---|---|---|
| 22 | −5.538 | −2.358 | 2.744 | 677 |
| 23 | −5.578 | −2.15 | 2.839 | 677 |
| 24 | −5.579 | −2.178 | 2.839 | 677 |
| 25 | −5.718 | −2.161 | 2.777 | 677 |
| 26 | −5.573 | −1.318 | 2.974 | 627 |
| 27 | −5.579 | −1.361 | 2.872 | 627 |
| 28 | −5.381 | −1.254 | 2.798 | 627 |
| 29 | −5.591 | −1.327 | 3.102 | 627 |
| 30 | −5.588 | −1.246 | 2.89 | 627 |
| 31 | −5.293 | −0.998 | 2.748 | 629 |
| 32 | −5.448 | −1.193 | 2.902 | 627 |
| 33 | −5.591 | −1.315 | 2.977 | 627 |
| 34 | −5.63 | −1.593 | 2.989 | 629 |
| 35 | −5.627 | −1.62 | 2.869 | 629 |
| 36 | −5.43 | −1.686 | 2.77 | 629 |
| 37 | −5.664 | −1.562 | 3.103 | 629 |
| 38 | −5.665 | −1.565 | 2.855 | 629 |
| 39 | −5.448 | −1.238 | 2.75 | 631 |
| 40 | −5.476 | −1.611 | 2.851 | 629 |
| 41 | −5.646 | −1.575 | 2.991 | 629 |
| 42 | −5.689 | −2.111 | 2.91 | 677 |
| 43 | −5.618 | −2.244 | 2.71 | 677 |
| 44 | −5.555 | −1.987 | 2.693 | 679 |
| 45 | −5.711 | −2.234 | 2.713 | 677 |
| 46 | −5.552 | −2.406 | 2.609 | 677 |
| 47 | −5.661 | −2.154 | 2.731 | 677 |
| 48 | −5.672 | −2.163 | 2.832 | 677 |
| 49 | −5.748 | −2.164 | 2.777 | 677 |
| 50 | −5.556 | −1.13 | 3.054 | 627 |
| 51 | −5.49 | −1.111 | 2.975 | 627 |
| 52 | −5.241 | −1.164 | 2.925 | 627 |
| 53 | −5.647 | −1.296 | 3.141 | 627 |
| 54 | −5.392 | −1.018 | 3.022 | 627 |
| 55 | −5.138 | −0.911 | 2.78 | 629 |
| 56 | −5.267 | −1.083 | 3.01 | 627 |
| 57 | −5.587 | −1.107 | 3.105 | 627 |
| 58 | −5.615 | −1.445 | 3.072 | 629 |
| 59 | −5.61 | −1.436 | 2.973 | 629 |
| 60 | −5.375 | −1.627 | 2.848 | 629 |
| 61 | −5.735 | −1.515 | 3.155 | 629 |
| 62 | −5.555 | −1.494 | 3.019 | 629 |
| 63 | −5.281 | −1.171 | 2.768 | 631 |
| 64 | −5.413 | −1.477 | 2.945 | 629 |
| 65 | −5.674 | −1.361 | 3.107 | 629 |
| 66 | −5.7 | −2.086 | 2.934 | 677 |
| 67 | −5.573 | −2.267 | 2.629 | 677 |
| 68 | −5.489 | −1.891 | 2.732 | 679 |
| 69 | −5.624 | −2.247 | 2.754 | 677 |
| 70 | −5.563 | −2.359 | 2.558 | 677 |
| 71 | −5.672 | −2.119 | 2.771 | 677 |
| 72 | −5.7 | −2.126 | 2.837 | 677 |
| 73 | −5.752 | −2.174 | 2.781 | 677 |
| 74 | −5.568 | −1.228 | 3.071 | 627 |
| 75 | −5.522 | −1.269 | 2.959 | 627 |
| 76 | −5.209 | −1.223 | 2.839 | 627 |
| 77 | −5.632 | −1.268 | 3.118 | 627 |
| 78 | −5.429 | −1.144 | 2.998 | 627 |
| 79 | −5.341 | −0.97 | 2.921 | 629 |
| 80 | −5.309 | −1.14 | 3.024 | 627 |
| 81 | −5.593 | −1.19 | 3.102 | 627 |
| 82 | −5.638 | −1.491 | 3.094 | 629 |
| 83 | −5.619 | −1.531 | 2.964 | 629 |
| 84 | −5.322 | −1.67 | 2.791 | 629 |
| 85 | −5.723 | −1.496 | 3.134 | 629 |
| 86 | −5.586 | −1.448 | 3 | 629 |
| 87 | −5.459 | −1.181 | 2.925 | 631 |
| 88 | −5.429 | −1.562 | 2.992 | 629 |
| 89 | −5.687 | −1.436 | 3.107 | 629 |
| 90 | −5.718 | −2.082 | 2.949 | 677 |
| 91 | −5.582 | −2.313 | 2.741 | 677 |
| 92 | −5.602 | −1.842 | 2.922 | 679 |
| 93 | −5.63 | −2.247 | 2.856 | 677 |
| 94 | −5.531 | −2.403 | 2.58 | 677 |
| 95 | −5.668 | −2.159 | 2.814 | 677 |
| 96 | −5.703 | −2.143 | 2.862 | 677 |
| 97 | −5.461 | −1.503 | 3.051 | 628 |
| 98 | −5.609 | −1.484 | 3.008 | 628 |
| 99 | −5.496 | −1.255 | 3.056 | 628 |
| 100 | −5.601 | −1.265 | 3.054 | 628 |
| 101 | −5.611 | −1.675 | 3.03 | 629 |
| 102 | −5.394 | −1.607 | 3.059 | 629 |
| 103 | −5.641 | −1.851 | 2.829 | 629 |
| 104 | −5.32 | −1.793 | 3.043 | 629 |
| 105 | −5.555 | −1.267 | 3.042 | 628 |
| 106 | −5.707 | −1.538 | 3.023 | 629 |
| 107 | −5.737 | −1.599 | 3.022 | 630 |

Synthesis methods of the condensed cyclic compound represented by Formula 1 may be easily understood by one of ordinary skill in the art by referring to Synthesis Examples provided below.

Accordingly, another aspect of embodiments provides an organic light-emitting device that includes:

a first electrode;

a second electrode; and an organic layer that is disposed between the first electrode and the second electrode, wherein the organic layer includes an emission layer and at least one condensed cyclic compound represented by Formula 1.

The condensed cyclic compound represented by Formula 1 may be used in the organic layer of the organic light-emitting device. For example, the condensed cyclic compound represented by Formula 1 may be used as a host in the emission layer of the organic layer. However, embodiments are not limited thereto.

The organic light-emitting device may have, due to the inclusion of an organic layer including the condensed cyclic compound represented by Formula 1, low driving voltage, high efficiency, high brightness, and long lifespan.

The condensed cyclic compound of Formula 1 may be used between a pair of electrodes of an organic light-emitting device. For example, the condensed cyclic compound represented by Formula 1 may be included in the emission layer. In this regard, the condensed cyclic compound may be a host, and the emission layer may further include a dopant (that is, an amount of the condensed cyclic compound represented by Formula 1 may be greater than an amount of the dopant). The emission layer may be a green emission layer emitting green light or a blue emission layer emitting blue light, and the dopant may be a phosphorescent dopant.

The expression that "(an organic layer) includes at least one condensed cyclic compound" used herein may include a case in which "(an organic layer) includes identical compounds represented by Formula 1 and a case in which (an organic layer) includes two or more different condensed cyclic compounds represented by Formula 1.

For example, the organic layer may include, as the condensed cyclic compound, only Compound 1. In this regard, Compound 1 may be situated in an emission layer of the organic light-emitting device. In some embodiments, the organic layer may include, as the condensed cyclic compound, Compound 1 and Compound 2. In this regard, Compound 1 and Compound 2 may be situated in an identical layer (for example, Compound 1 and Compound 2 all may be situated in an emission layer).

The first electrode may be an anode, which is a hole injection electrode, and the second electrode may be a cathode, which is an electron injection electrode, or the first electrode may be a cathode, which is an electron injection electrode, or the second electrode may be an anode, which is a hole injection electrode.

For example, the first electrode is an anode, and the second electrode may be a cathode, and the organic layer may include:

i) a hole transport region that is disposed between the first electrode and the emission layer, wherein the hole transport region includes at least one of a hole injection layer, a hole transport layer, and an electron blocking layer, and ii) an electron transport region that is disposed between the emission layer and the second electrode, wherein the electron transport region includes at least one layer selected from a hole blocking layer, an electron transport layer, and an electron injection layer.

The term "organic layer" used herein refers to a single layer and/or a plurality of layers disposed between the first electrode and the second electrode of an organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

In FIG. 1, a substrate may be additionally disposed under the first electrode 11 or above the second electrode 19. For use as the substrate, any substrate that is used in general organic light-emitting devices may be used, and the substrate may be a glass substrate or transparent plastic substrate, each with excellent mechanical strength, thermal stability, transparency, surface smoothness, ease of handling, and water-proofness.

The first electrode 11 may be formed by depositing or sputtering a material for forming the first electrode on the substrate. The first electrode 11 may be an anode. The material for the first electrode 11 may be selected from materials with a high work function to allow holes be easily provided. The first electrode 11 may be a reflective electrode or a transmissive electrode. The material for the first electrode 11 may be an indium tin oxide (ITO), indium zinc oxide (IZO), tin oxide ($SnO_2$), or zinc oxide (ZnO). In some embodiments, the material for the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layer structure or a multi-layer structure including two or more layers. For example, the first electrode 11 may have a three-layered structure of ITO/Ag/ITO, but the structure of the first electrode 110 is not limited thereto.

An organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one of a hole injection layer, a hole transport layer, an electron blocking layer, and a buffer layer.

The hole transport region may include only either a hole injection layer or a hole transport layer. In some embodiments, the hole transport region may have a structure of hole injection layer/hole transport layer or hole injection layer/hole transport layer/electron blocking layer, which are sequentially stacked in this stated order from the first electrode 11.

When the hole transport region includes a hole injection layer (HIL), the hole injection layer may be formed on the first electrode 11 by using any one of various methods, for example, vacuum deposition, spin coating, casting, or Langmuir-Blodgett (LB) deposition.

When a hole injection layer is formed by vacuum deposition, the deposition conditions may vary depending on a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (Å/sec). However, the deposition conditions are not limited thereto.

When the hole injection layer is formed using spin coating, coating conditions may vary depending on the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202:

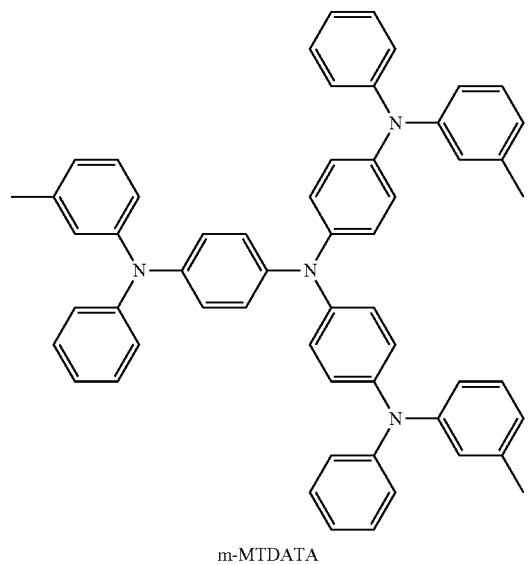

m-MTDATA

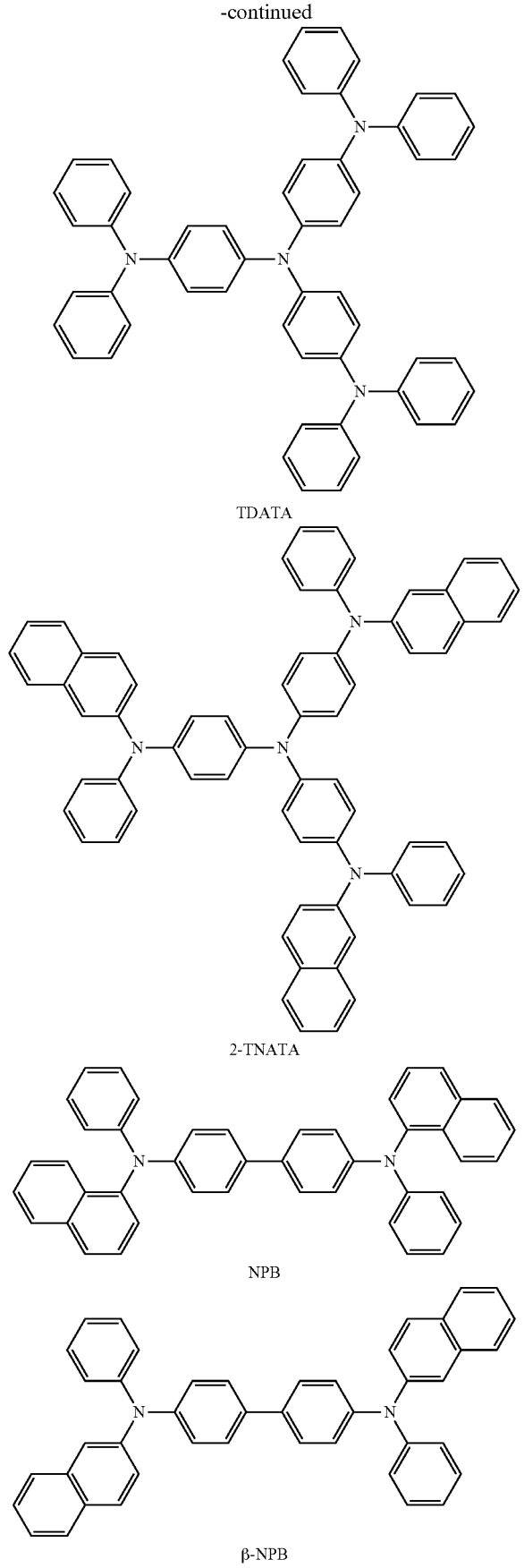
TDATA
2-TNATA
NPB
β-NPB
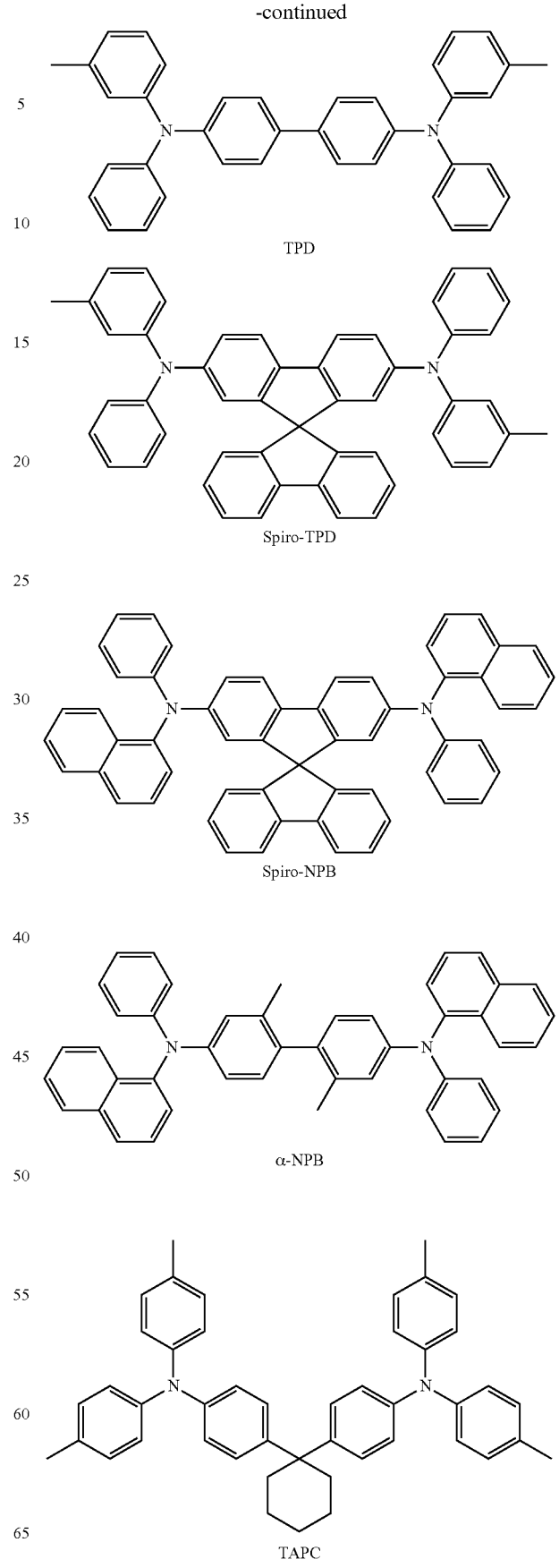
TPD
Spiro-TPD
Spiro-NPB
α-NPB
TAPC

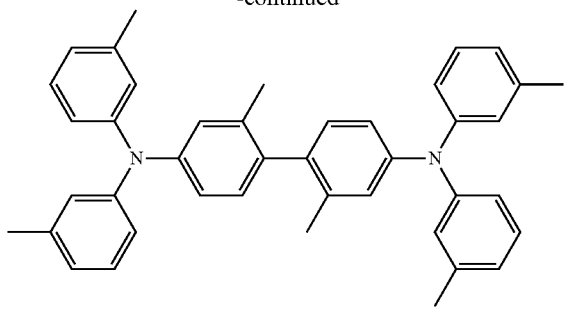

HMTPD

Formula 201

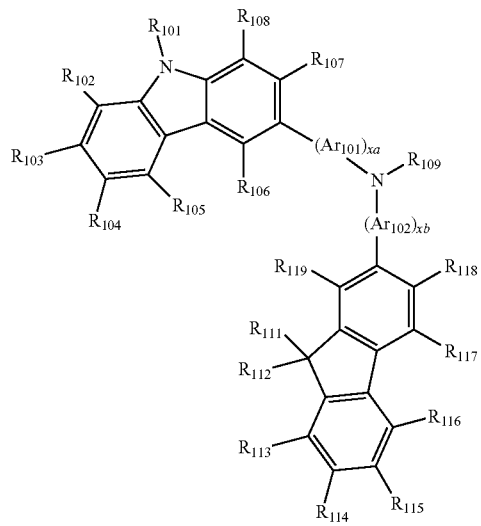

Formula 202

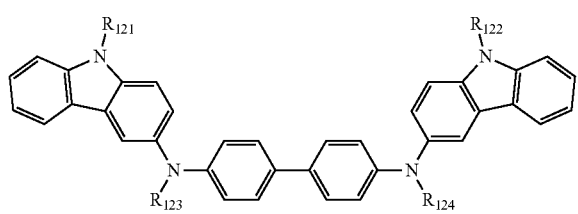

$Ar_{101}$ and $Ar_{102}$ in Formula 201 may be each independently selected from phenylene, pentalenylene, indenylene, naphthylene, azulenylene, heptalenylene, acenaphthylene, fluorenylene, pentalenylene, phenanthrenylene, anthracenylene, fluoranthenylene, triphenylenylene, pyrenylene, chrysenylenylene, naphthacenylene, picenylene, perylenylene, and pentacenylene; and a phenylene, a pentalenylene, an indenylene, a naphthylene, an azulenylene, a heptalenylene, an acenaphthylene, a fluorenylene, a pentalenylene, a phenanthrenylene, an anthracenylene, a fluoranthenylene, a triphenylenylene, a pyrenylene, a chrysenylenylene, a naphthacenylene, a picenylene, a perylenylene, and a pentacenylene, each substituted with at least one selected from a deuterium, a halogen atom, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

xa and xb in Formula 201 may be each independently an integer of 0 to 5, or 0, 1 or 2. For example, xa may be 1 and xb may be 0, but xa and xb are not limited thereto.

$R_{101}$ to $R_{108}$, $R_{111}$ to $R_{119}$, and $R_{121}$ to $R_{124}$ in Formulae 201 and 202 may be each independently selected from a hydrogen, a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl (for example, methyl, ethyl, propyl, butyl, pentyl, or hexyl), and a $C_1$-$C_{10}$ alkoxy (for example, methoxy, ethoxy, propoxy, butoxy, or pentoxy);

a $C_1$-$C_{10}$ alkyl group and a $C_1$-$C_{10}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

phenyl, naphthyl, anthracenyl, fluorenyl, and pyrenyl; and a phenyl, a naphthyl, an anthracenyl, a fluorenyl, and a pyrenyl, each substituted with at least one selected from deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

$R_{109}$ in Formula 201 may be one selected from phenyl, naphthyl, anthracenyl, biphenyl, and pyridinyl, each substituted with at least one selected from phenyl, naphthyl, anthracenyl, biphenyl and pyridinyl; and deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl, and a $C_1$-$C_{20}$ alkoxy.

According to an embodiment, the compound represented by Formula 201 may be represented by Formula 201A below, but is not limited thereto:

Formula 201A

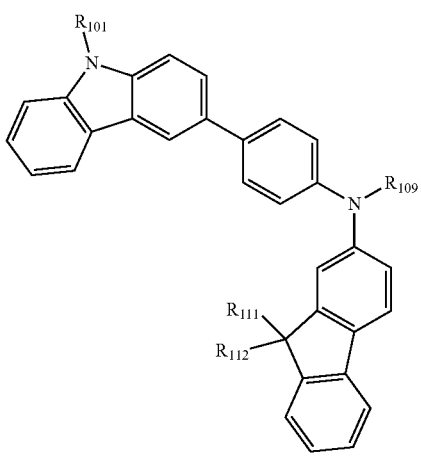

$R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto.

HT1
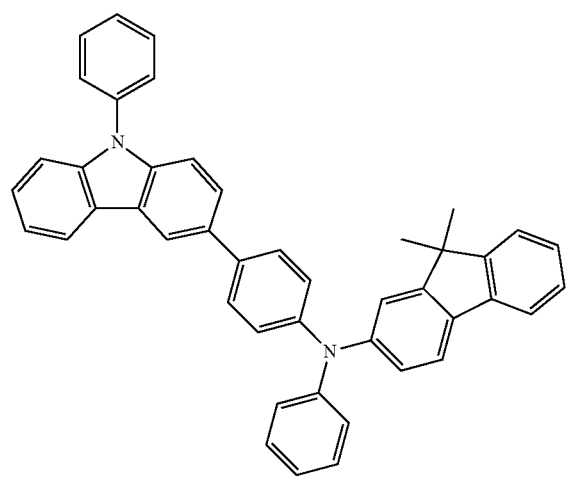
HT2
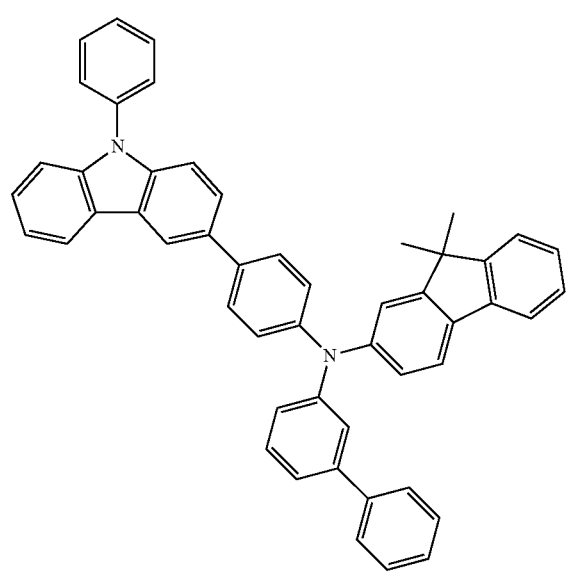
HT3
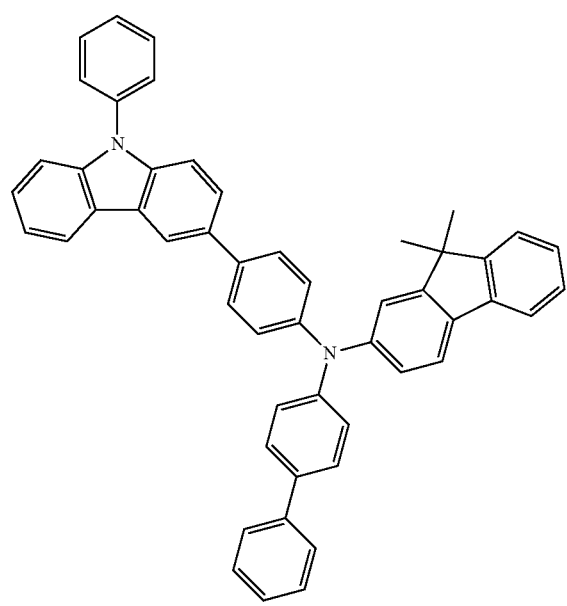
HT4
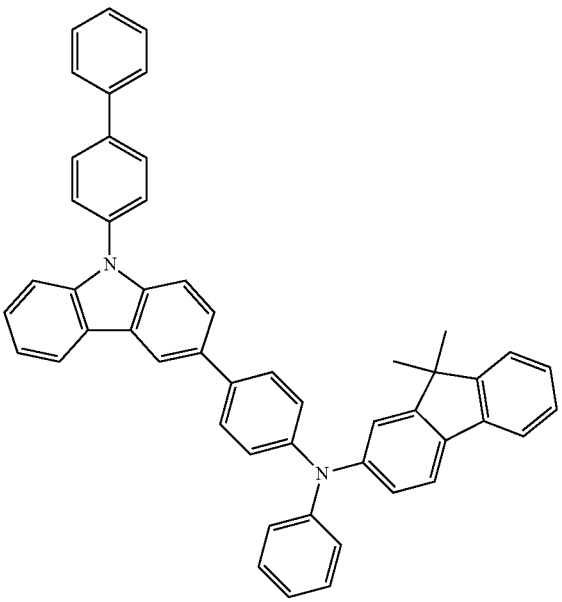
HT5
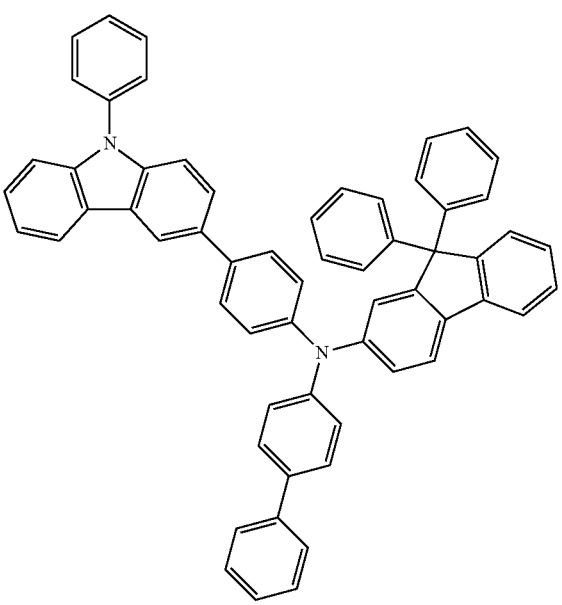

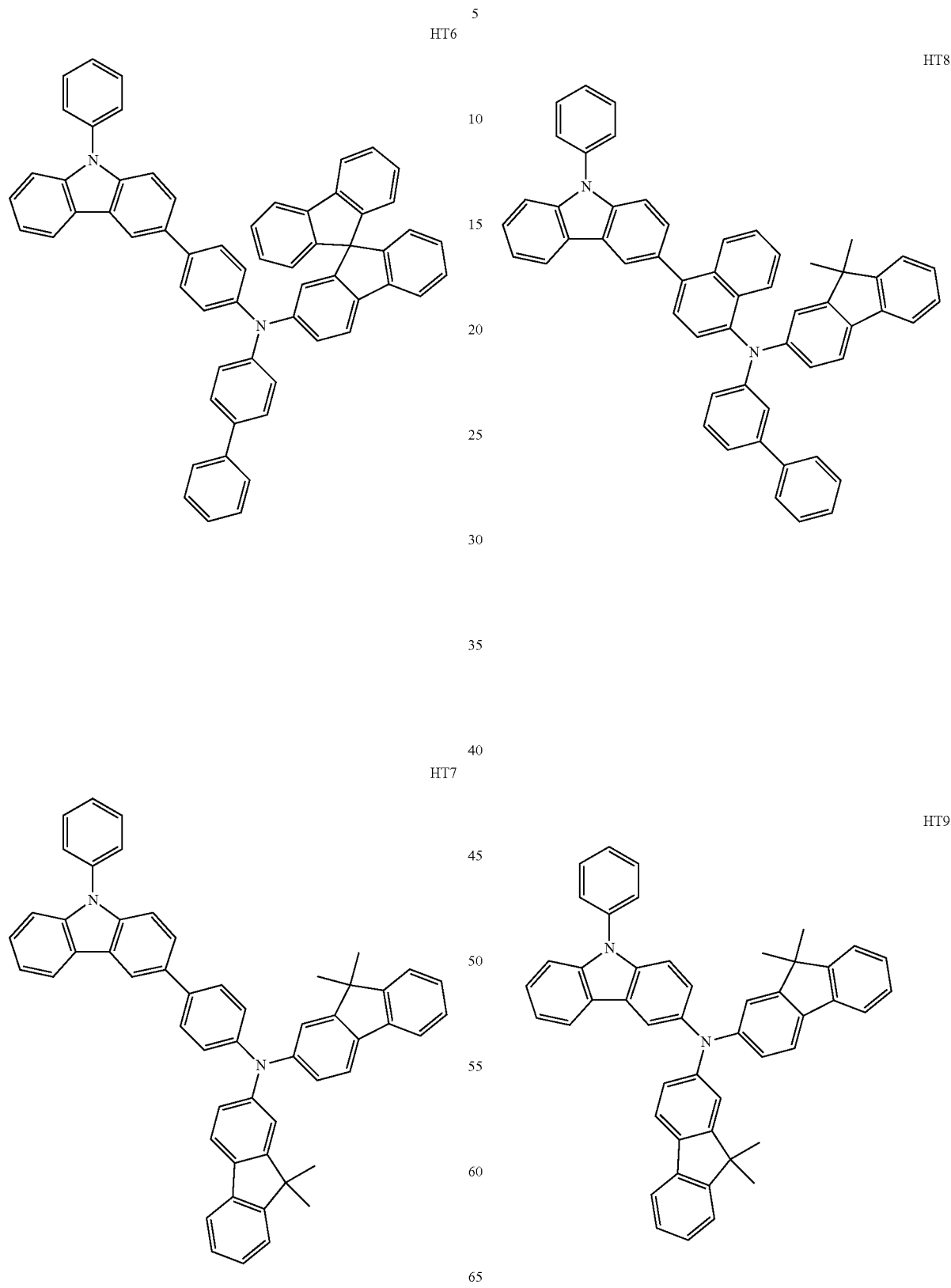

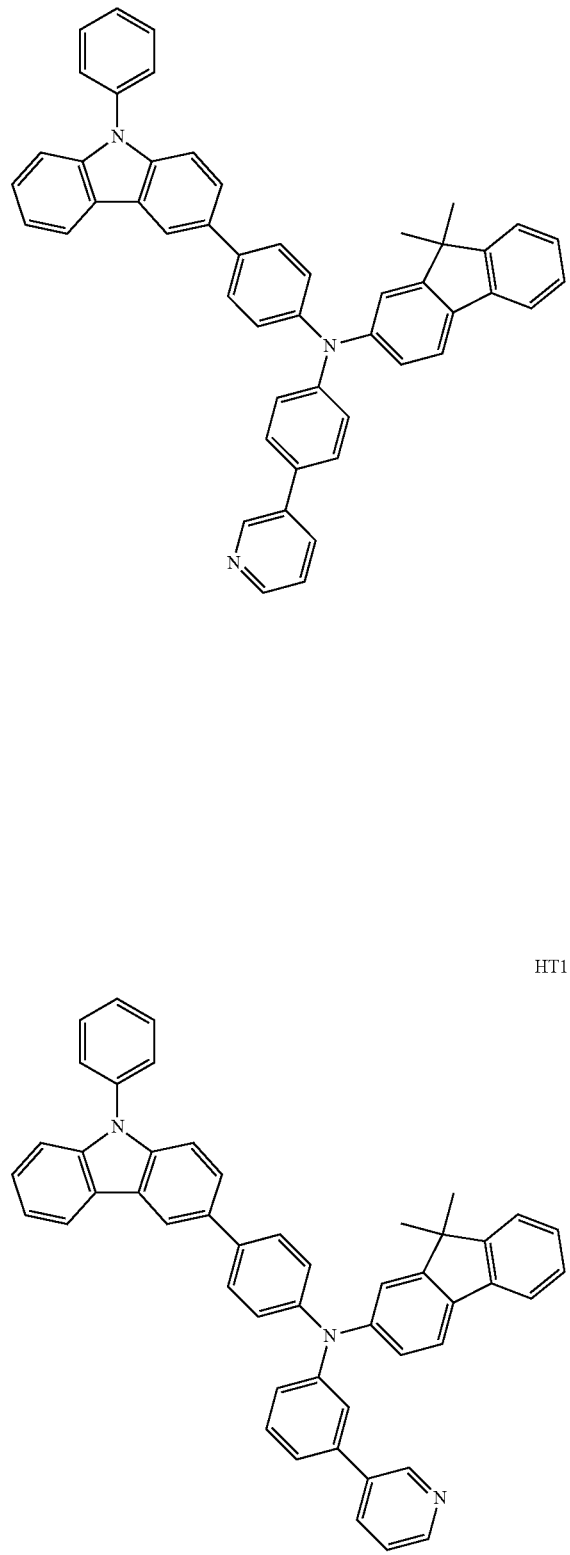
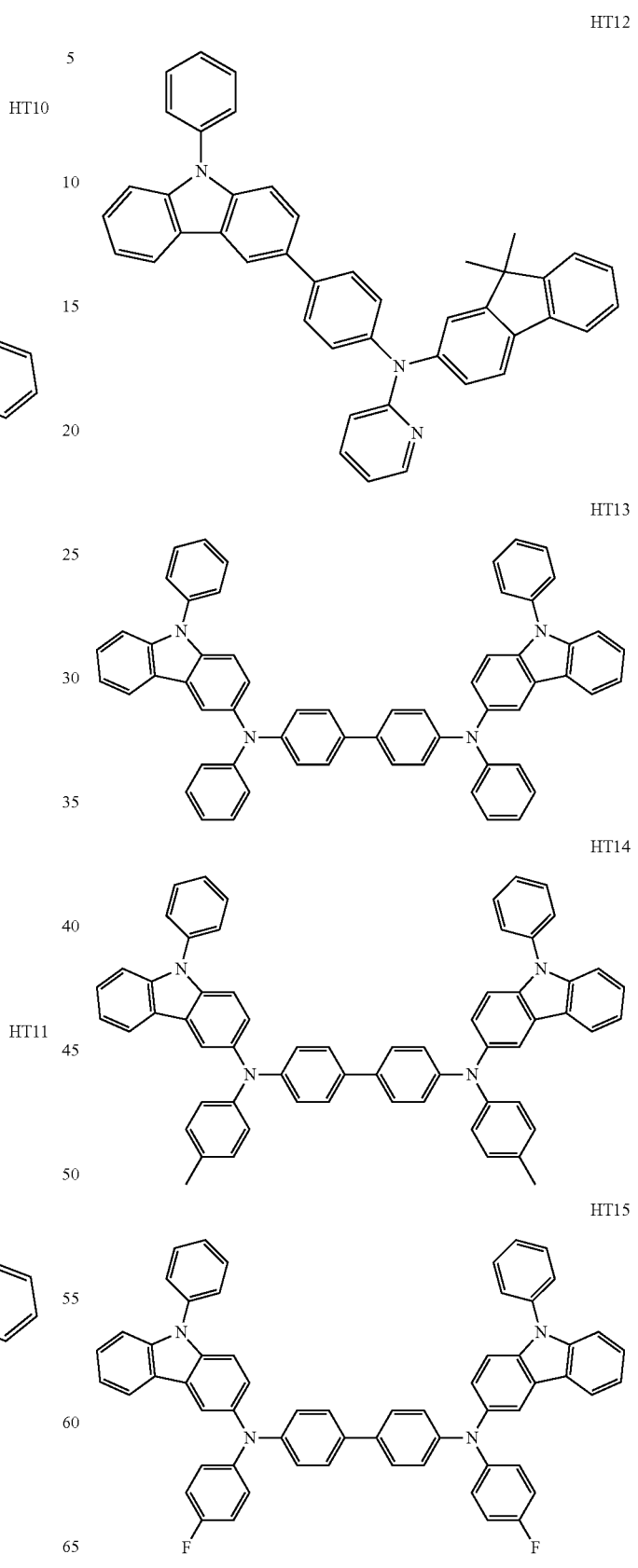

-continued

HT16

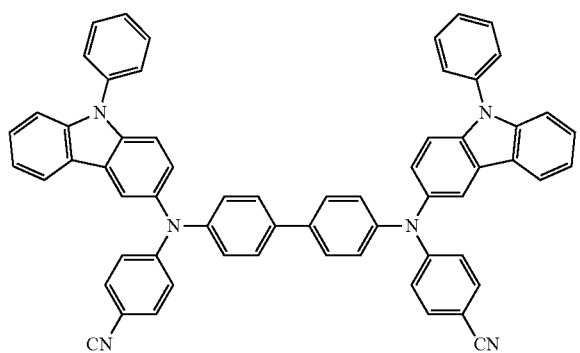

HT17

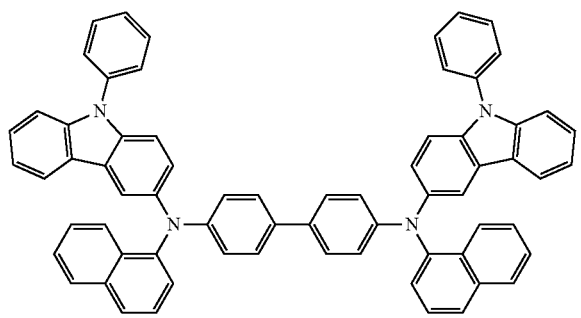

HT18

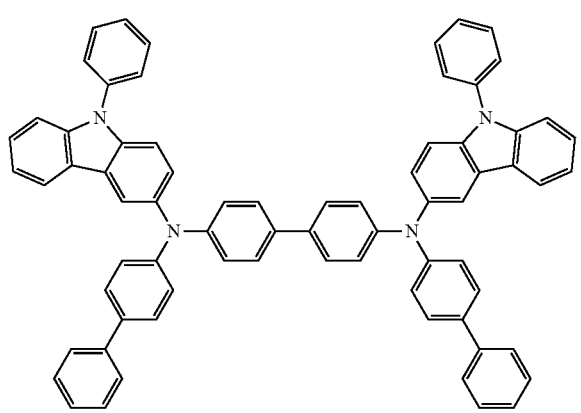

HT19

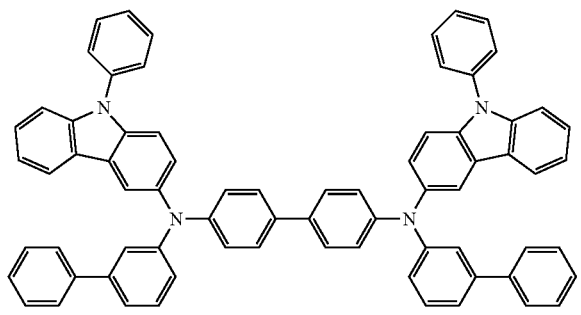

-continued

HT20

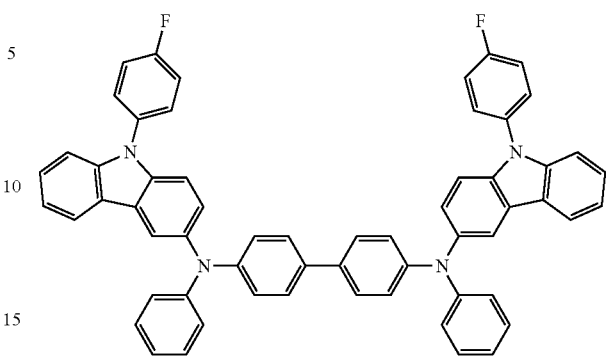

A thickness of the hole transport region may be in a range of about 100 Angstroms (Å) to about 10,000 Å, for example, about 100 Å to about 1,000 Å. When the hole transport region includes both a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one of a quinone derivative, a metal oxide, and a cyano group-containing compound, but is not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 below, but embodiments are not limited thereto.

Compound HT-D1

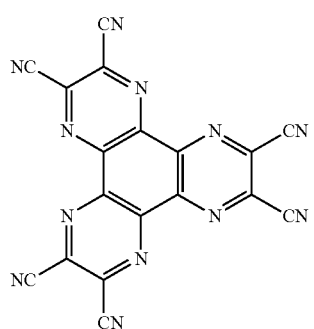

-continued

F4-TCNQ

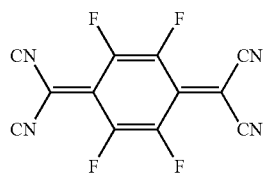

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

The electron transport region may further include an electron blocking layer. The electron blocking layer may include, for example, mCP, but a material therefor is not limited thereto.

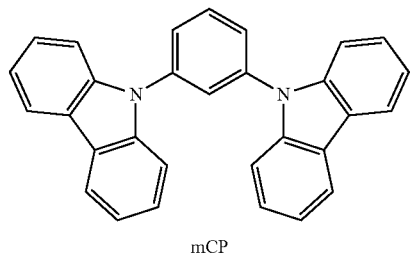 [SMILES: c1cc(-n2c3ccccc3c3ccccc32)cc(-n2c3ccccc3c3ccccc32)c1]

mCP

When the organic light-emitting device is a full color organic light-emitting device, the emission layer may be patterned into a red emission layer, a green emission layer, and a blue emission layer. In some embodiments, due to a stack structure including a red emission layer, a green emission layer, and/or a blue emission layer, the emission layer may emit white light.

The emission layer may include the condensed cyclic compound represented by Formula 1. The emission layer may include a dopant. The dopant may be at least one selected from a phosphorescent dopant and a fluorescent dopant.

For example, a host in the emission layer may include the condensed cyclic compound represented by Formula 1.

The dopant in the emission layer may include a phosphorescent dopant that emits light according to a phosphorescent emission mechanism. In detail, the phosphorescent dopant may emit blue light, but embodiments are not limited thereto.

The phosphorescent dopant may include an organometallic compound represented by Formula 401:

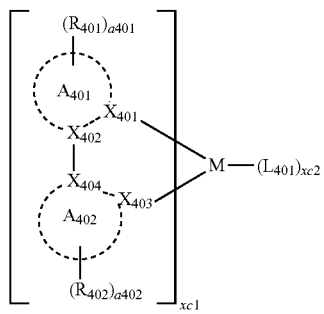

Formula 401 wherein in Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently nitrogen or carbon;

$Y_{401}$ and $Y_{402}$ are linked via a single bond or a double bond, and $Y_{403}$ and $Y_{404}$ are linked via a single bond or a double bond;

$A_{401}$ and $A_{402}$ rings are each independently selected from a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, an oxadiazole, a triazine, a dibenzofuran, and a dibenzothiophene, and the $A_{401}$ and $A_{402}$ rings are optionally linked to each other through a single bond or an organic linking group;

$R_{401}$ to $R_{402}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), or —B(Q$_6$)(Q$_7$);

a81 and a82 are each independently an integer of 1 to 5;

$L_{401}$ is an organic ligand;

xc1 is 1, 2, or 3;

xc2 is 0, 1, 2, or 3; and $Q_1$ to $Q_7$ are each independently selected from a $C_1$-$C_{60}$ alkyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

$L_{401}$ may be a monovalent, divalent, or trivalent organic ligand. For example, $L_{401}$ may be selected from a halogen ligand (for example, Cl or F), a diketone ligand (for example, acetylacetonate, 1,3-diphenyl-1,3-propanedionate, 2,2,6,6-tetramethyl-3,5-heptanedionate, or hexafluoroacetonate), a carboxylic acid ligand (for example, picolinate, dimethyl-3-pyrazolecarboxylate, or benzoate), a carbon monoxide ligand, an isonitrile ligand, a cyano ligand, and a phosphorous ligand (for example, phosphine, and phosphite), but is not limited thereto.

When $A_{401}$ in Formula 401 has two or more substituents, the substituents of $A_{401}$ may bind to each other to form a saturated or unsaturated ring.

When $A_{401}$ in Formula 402 has two or more substituents, the substituents of $A_{402}$ may bind to each other to form a saturated or unsaturated ring.

When xc1 in Formula 401 is two or more, ligands

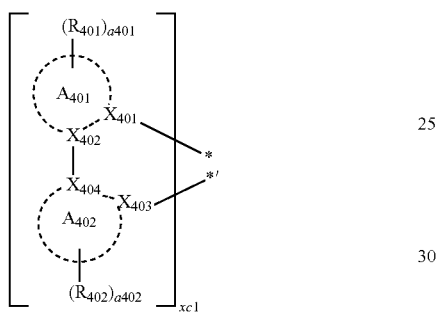

in Formula 401 may be identical or different. When xc1 in Formula 401 is two or more, $A_{401}$ and $A_{402}$ may be respectively directly connected to $A_{401}$ and $A_{402}$ of other neighboring ligands with or without a linker, for example, a $C_1$-$C_5$ alkylene, or —N(R')—, (wherein R' may be a $C_1$-$C_{10}$ alkyl group or a $C_6$-$C_{20}$ aryl group) or —C(=O)—) therebetween.

The phosphorescent dopant may include at least one of Compounds PD1 to PD74 below, but is not limited thereto:

PD1

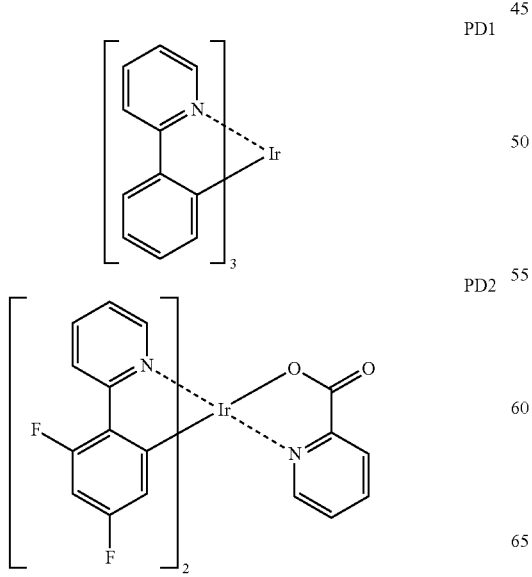

PD2

PD3

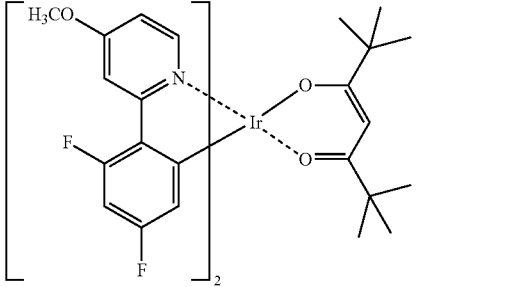

PD4

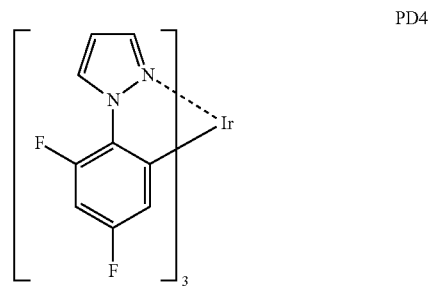

PD5

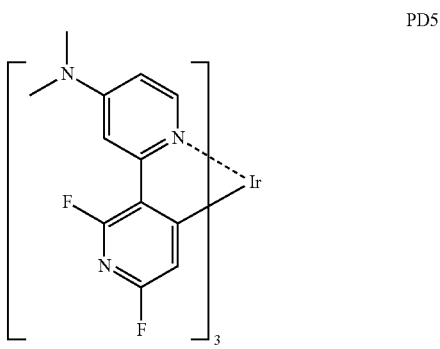

PD6

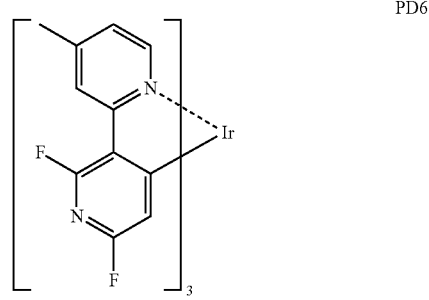

PD7

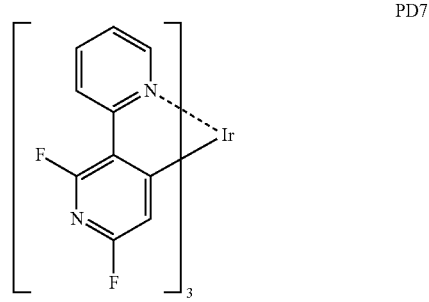

PD8
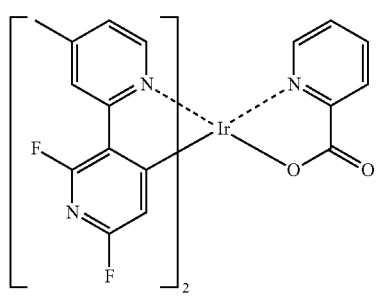
PD9
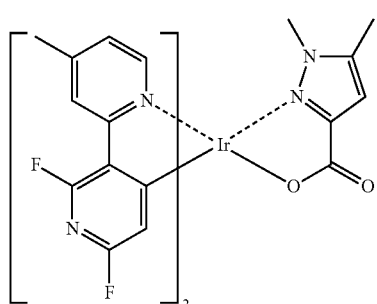
PD10
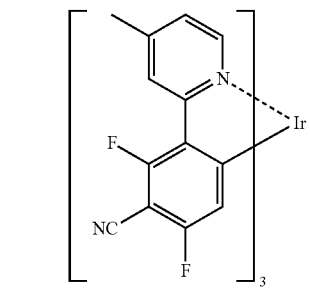
PD11
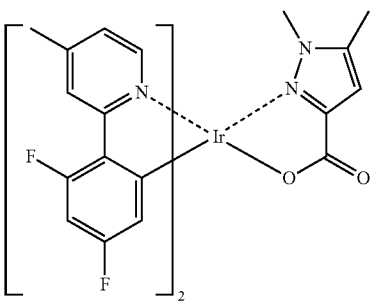
PD12
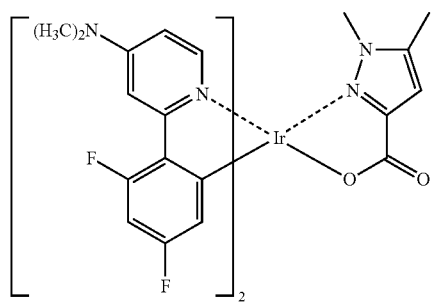
PD13
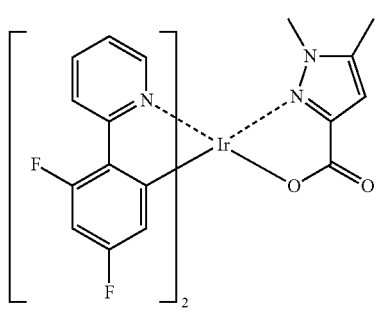
PD14
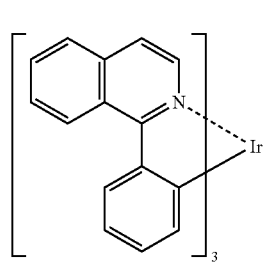
PD15
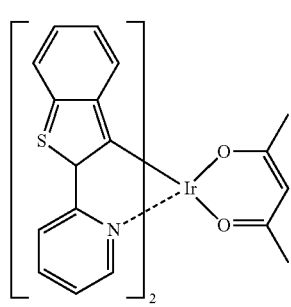
PD16
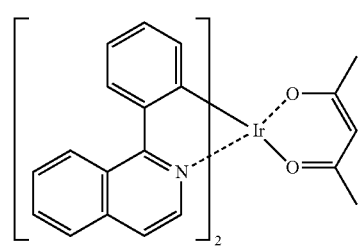
PD17
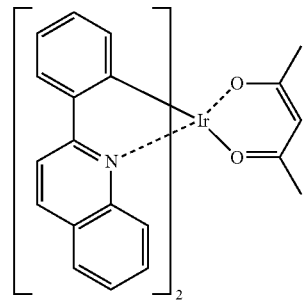

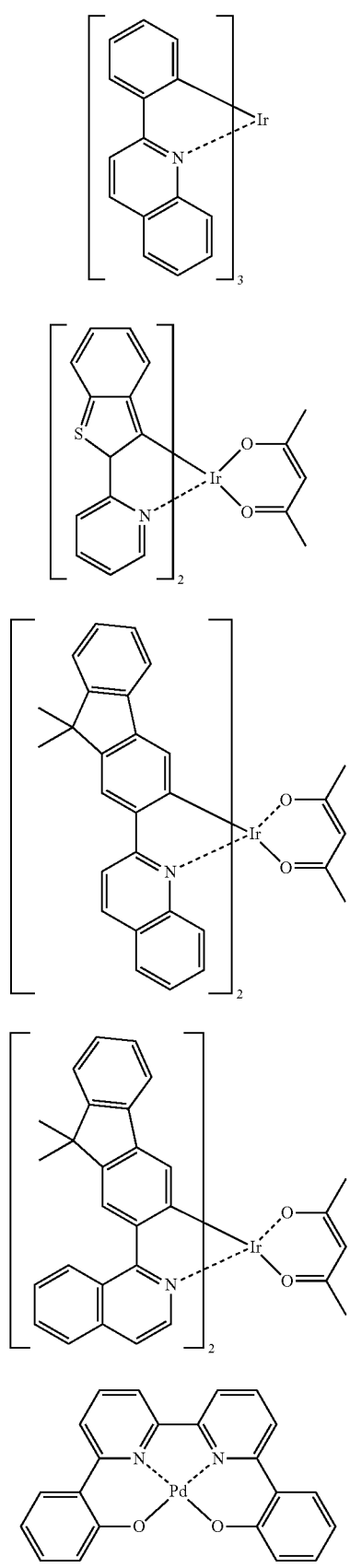
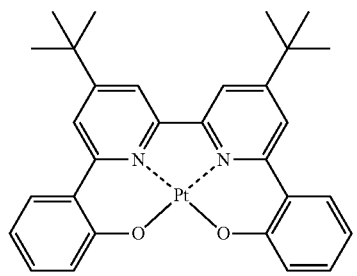
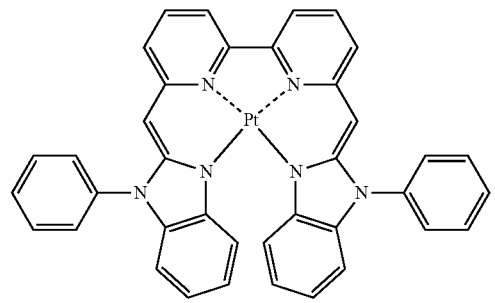
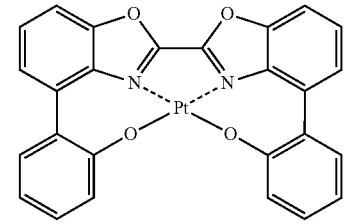
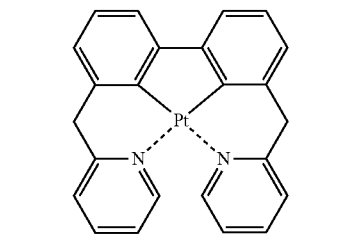
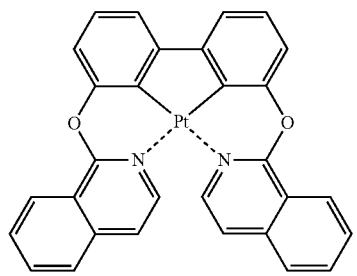
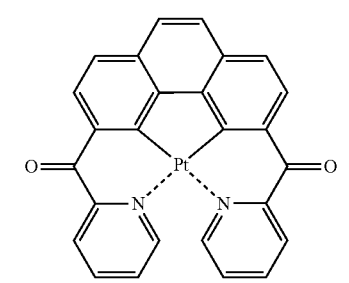

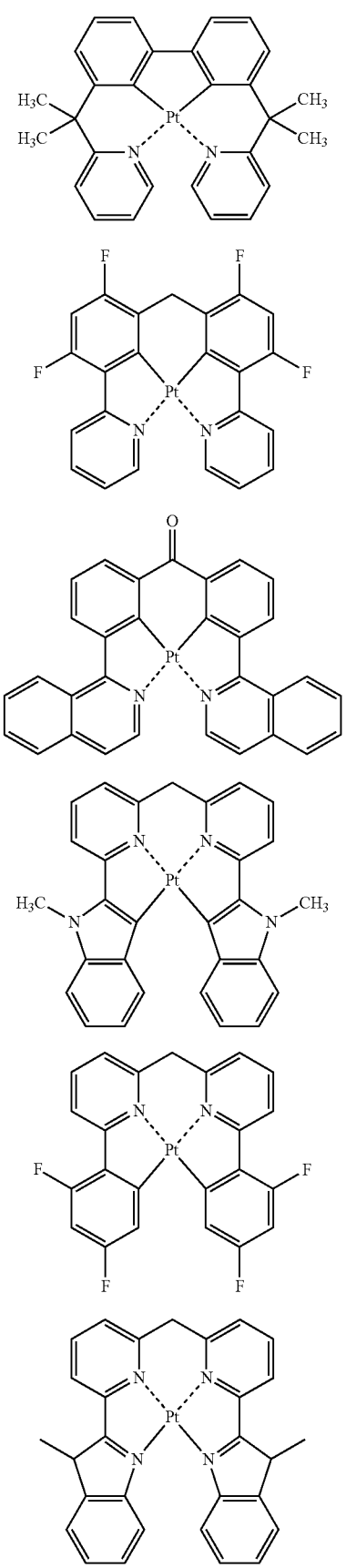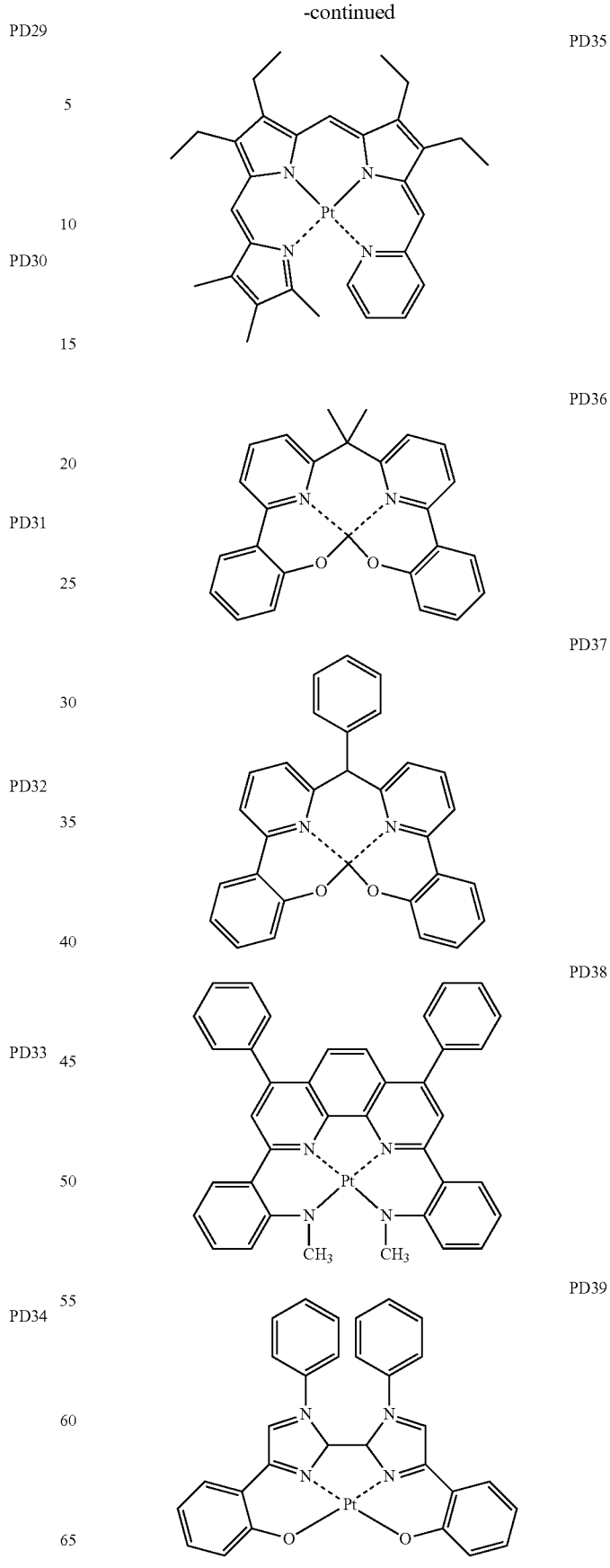

PD40 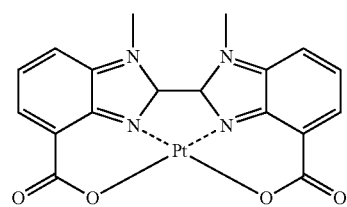
PD41 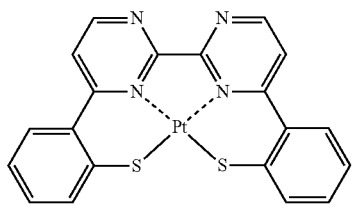
PD42 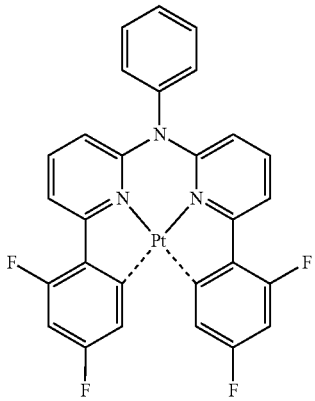
PD43 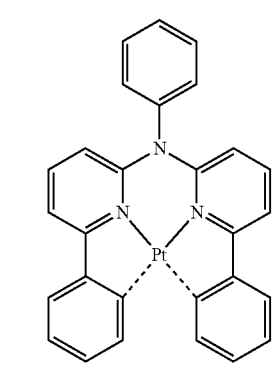
PD44 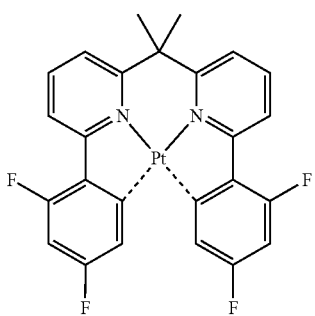
PD45 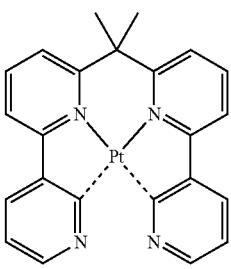
PD46 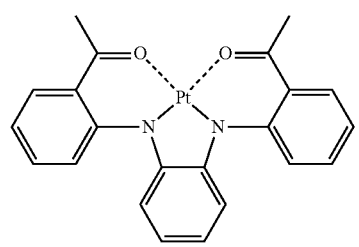
PD47 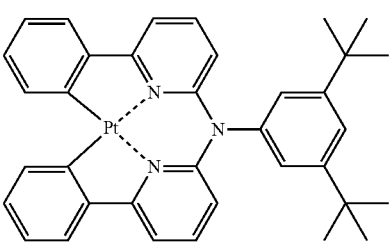
PD48 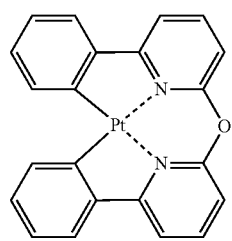
PD49 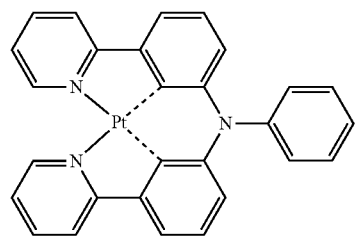
PD50 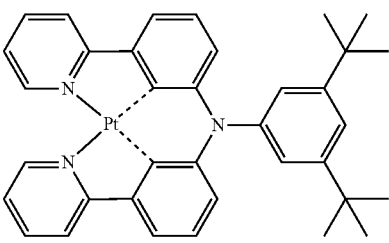

PD51 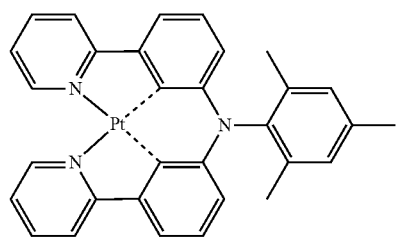
PD52 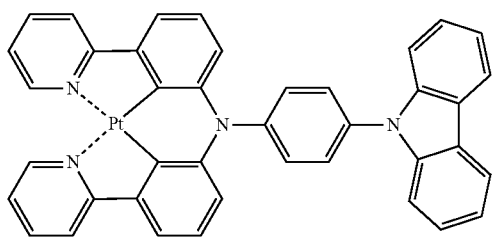
PD53 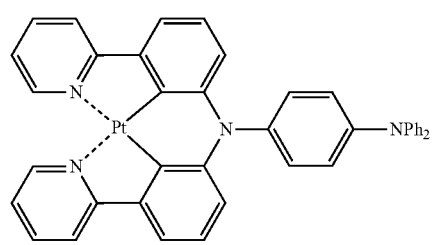
PD54 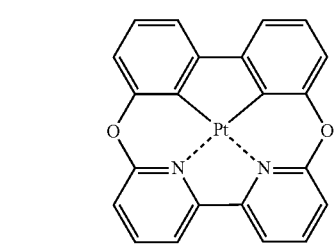
PD55 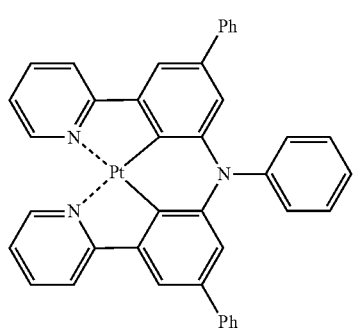
PD56 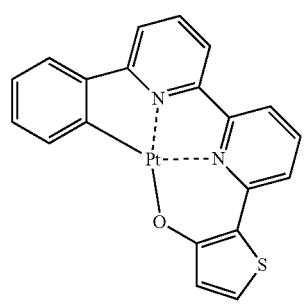
PD57 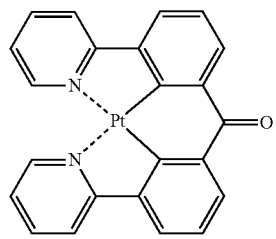
PD58 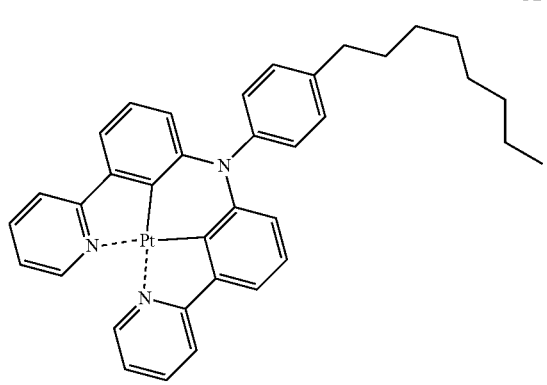
PD59 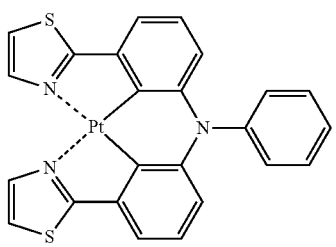
PD60 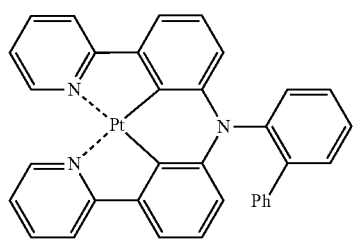
PD61 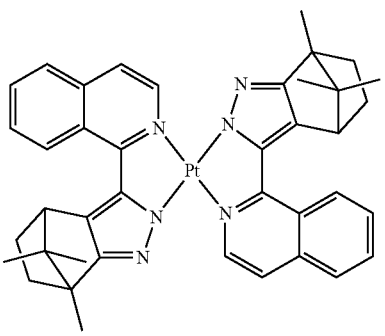

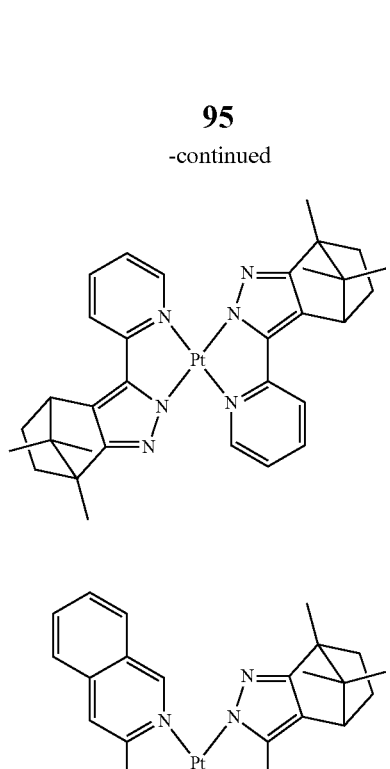
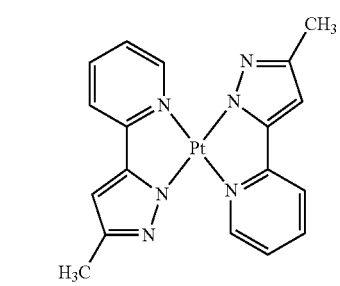
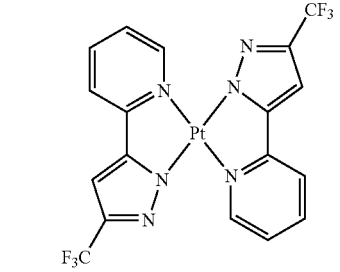
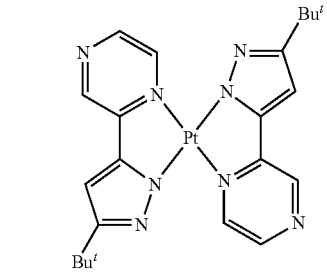

-continued
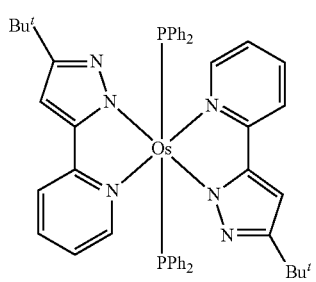
PD72
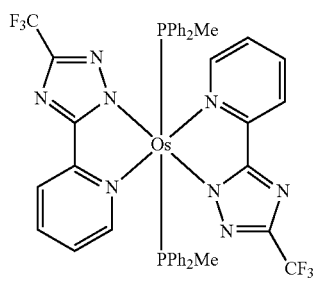
PD73
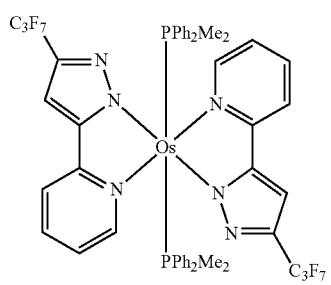
PD74
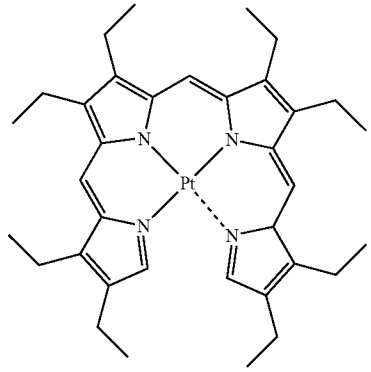
PtOEP
-continued
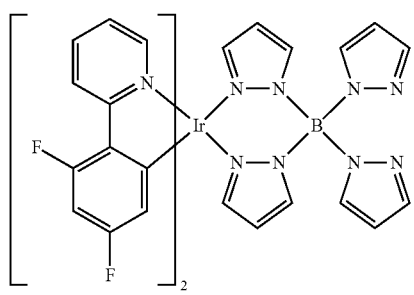
FIr6
In some embodiments, the phosphorescent dopant may include PtOEP or Fir 6:
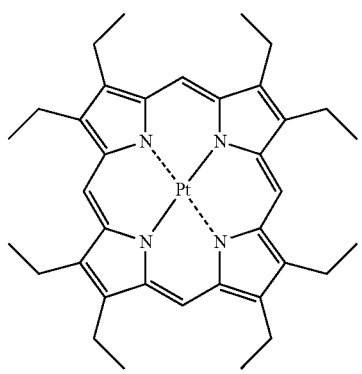
PtOEP
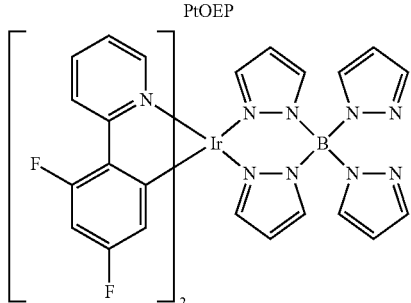
FIr6
The fluorescent dopant may include at least one selected from DPAVBi, BDAVBi, TBPe, DCM, DCJTB, Coumarin 6, and C545T.
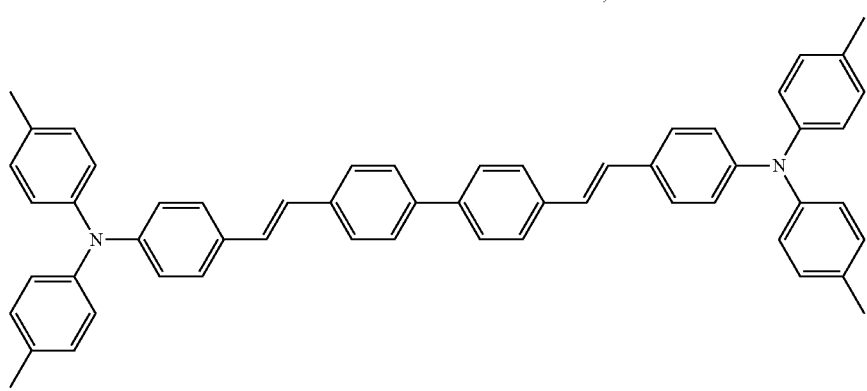
DPAVBi -continued

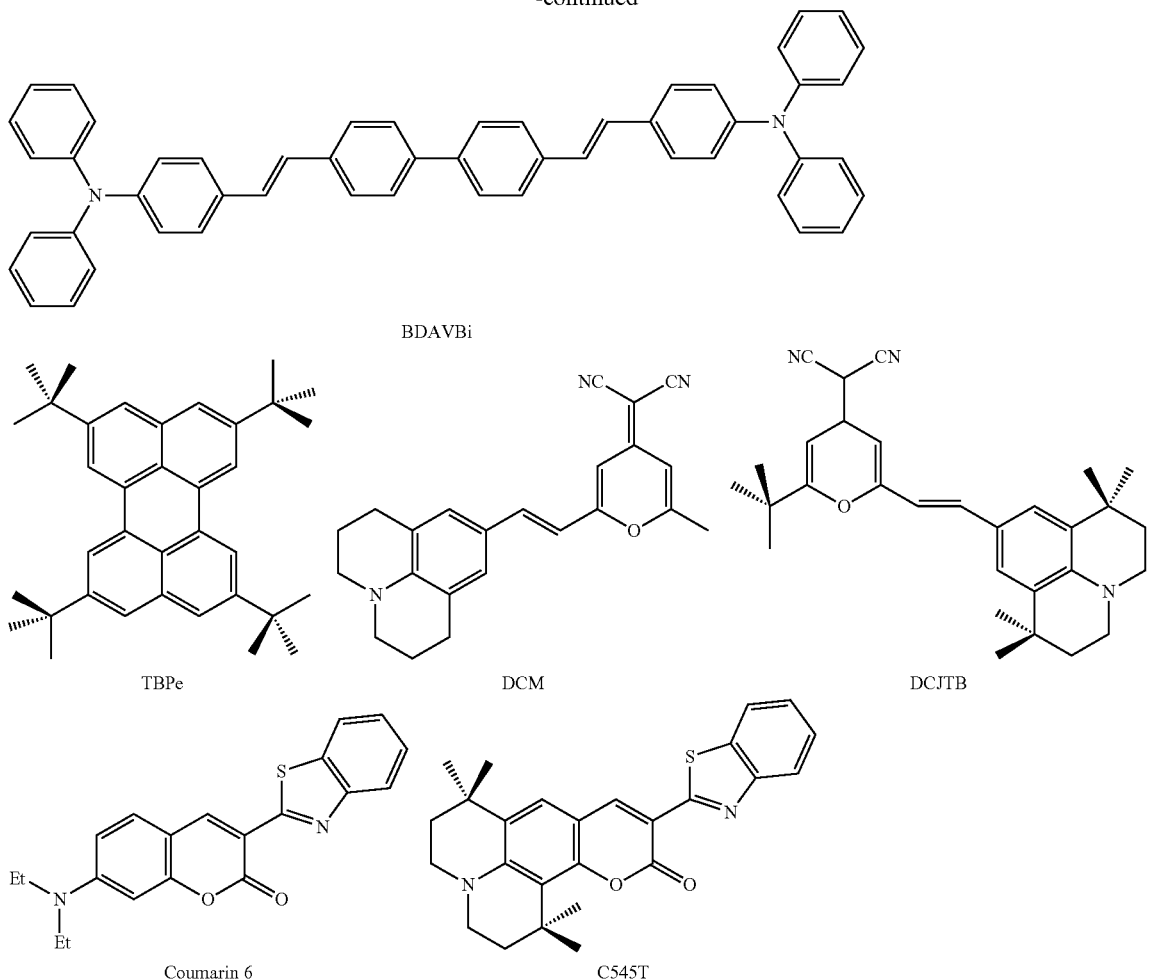

When the emission layer includes a host and a dopant, an amount of the dopant may be in a range of about 0.01 to about 20 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport layer includes a hole blocking layer, the hole blocking layer may include, for example, at least one of BCP, Bphen, and TmPyPB, but embodiments are not limited thereto.

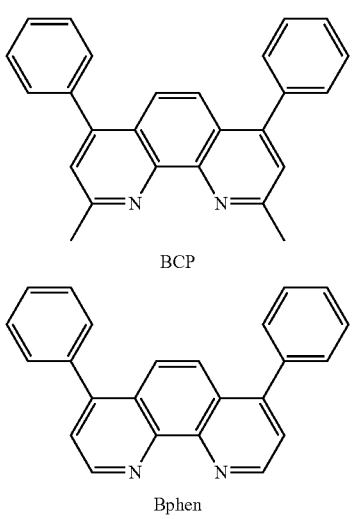

-continued

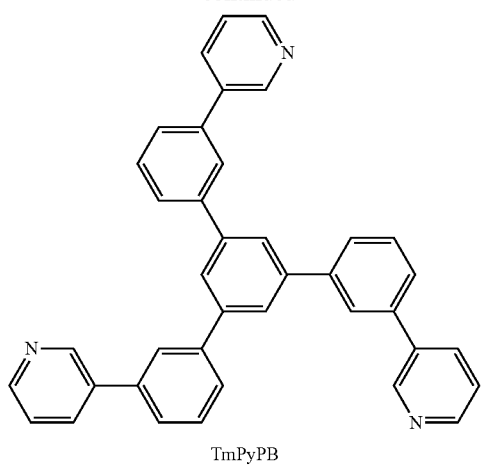

TmPyPB

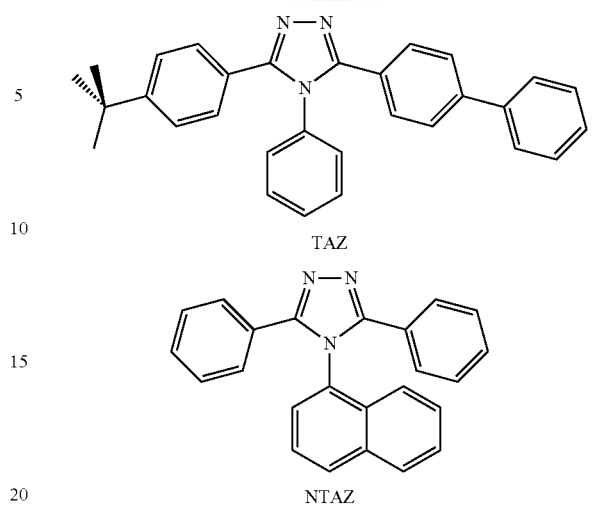

TAZ

NTAZ

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include, in addition to the organometallic compound represented by Formula 1, at least one selected from BCP, Bphen, $Alq_3$, Balq, TAZ, and NTAZ.

In some embodiments, the electron transport layer may include at least one of Compounds ET1, ET2, and ET3, but embodiments are not limited thereto:

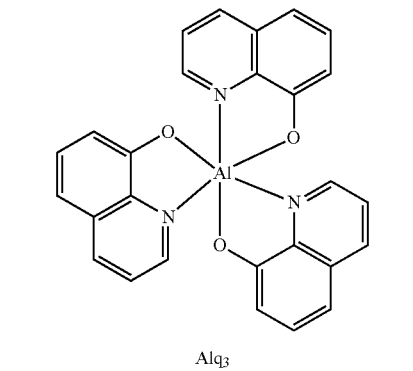

$Alq_3$

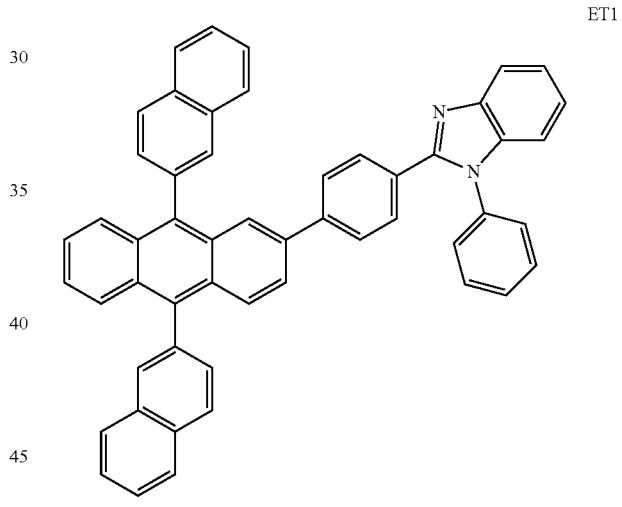

ET1

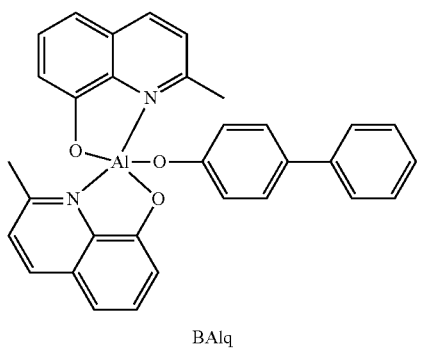

BAlq

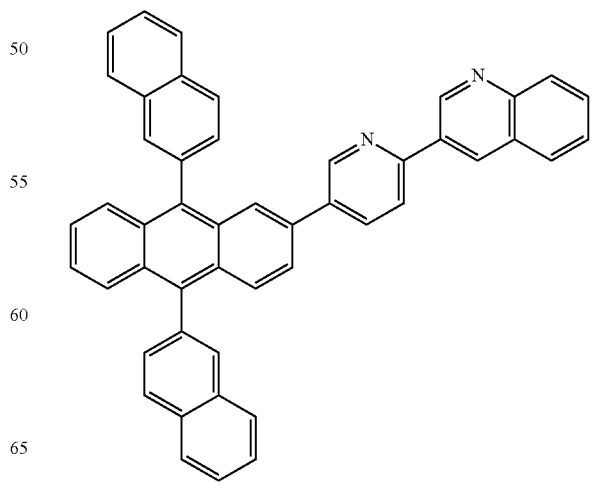

ET2

ET3

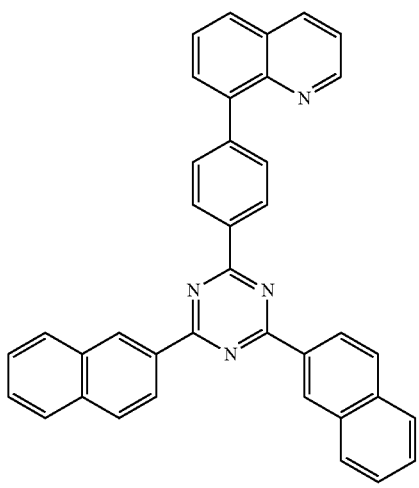

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-D1

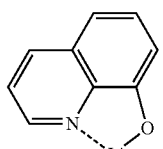

ET-D2

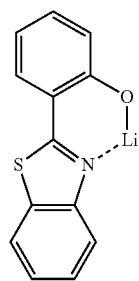

The electron transport region may include an electron injection layer (EIL) that allows electrons to be easily provided from a second electrode 19.

The electron injection layer may include at least one selected from, LiF, NaCl, CsF, $Li_2O$, BaO, and LiQ.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top emission type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{60}$ alkyl group as used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a hydrocarbon group formed by substituting at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group formed by substituting at least one carbon triple bond in the middle or at the terminal of the $C_2$-$C_{60}$ alkyl group. Detailed examples thereof are an ethynyl group, and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent mono cyclic group having at least one hetero atom selected from N, O, P, and S as a ring-forming atom and 1 to 10 carbon atoms. Detailed examples thereof are a tetrahydrofuranyl group, and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in the ring thereof, which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one hetero atom selected from N, O, P, and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system that has at least one hetero atom selected from N, O, P, and S as a ring-forming atom, and 1 to 60 carbon atoms. A $C_1$-$C_{60}$ heteroarylene group as used herein refers to a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group indicates —$SA_{103}$ (wherein $A_{103}$ is the $C_6$-$C_{60}$ aryl group).

A monovalent non-aromatic condensed polycyclic group as used herein refers to a monovalent group that has two or more rings condensed to each other, only carbon atoms (for example, the number of carbon atoms may be in a range of 8 to 60) as a ring forming atom, and which is non-aromatic. An example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent group that has two or more rings condensed to each other, has a heteroatom selected from N, O, P, and S, other than carbon atoms (for example, the number of carbon atoms may be in a range of 2 to 60), as a ring forming atom, and which is non-aromatic. An example of the monovalent non-aromatic condensed heteropolycyclic group is a carbazolyl group. A divalent non-aromatic condensed heteropolycyclic group as used herein refers to a divalent group having the same structure as the monovalent non-aromatic condensed heteropolycyclic group.

A "biphenyl group" as used herein refers to a "phenyl group substituted with a phenyl group.

Hereinafter, a compound and an organic light-emitting device according to embodiments are described in detail with reference to Synthesis Example and Examples. However, the organic light-emitting device is not limited thereto. The phrase "'B' was used instead of 'A'" used in describing Synthesis Examples means that a molar equivalent of 'A' was identical to a molar equivalent of 'B'.

EXAMPLE

Synthesis Example 1: Synthesis of Compound 2

(1) Synthesis of Intermediate 53-1

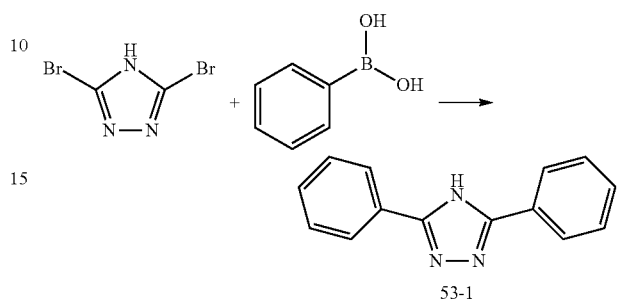

3,5-dibromo-4H-1,2,4-triazole (10.00 g, 1 eq.), a phenylboronic acid (11.82 g, 2.2 eq.), a palladium catalyst (2.54 g, 0.05 mol %), and tetrahydrofuran were added to a flask. Potassium carbonate (12.19 g) was subsequently added, and the result was stirred at a temperature of 100° C. under reflux. When the reaction was completed, a reaction product was cooled, and 500 mL of methanol was added thereto to form a precipitate. The precipitate was filtered, and recrystallized by using hexane to obtain 6.83 g (yield: 70%) of Intermediate 53-1 which had yellow color.

(2) Synthesis of Intermediate 53-2

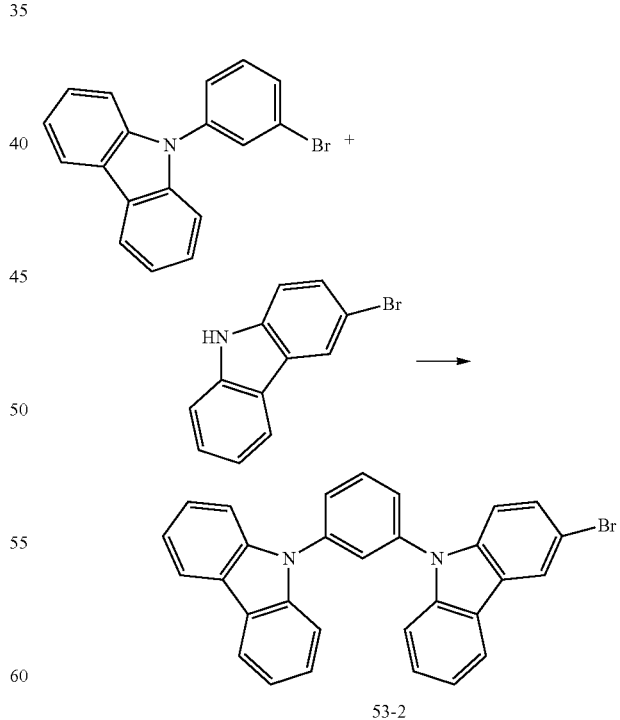

9-(3-bromophenyl)-9H-carbazole (1.95 g, 1.5 eq.) and 3-bromo-carbazole (1.00 g, 1 eq.) were added to a flask, a copper catalyst (0.52 g, 2 eq.), 4 eq. of potassium carbonate (2.24 g), dibenzo-18-crown-6 (0.14 g, 0.1 eq.), and xylene were added thereto, and the result was stirred at a temperature of 140° C. under reflux. When the reaction was complete, the reaction mixture was cooled and filtered to remove copper therefrom. A solvent was removed from the remaining solution, and the result was purified by column chromatography using methylene chloride and hexane as an eluent to obtain Intermediate 53-2 (1.43 g) in the yield of 72%.

(3) Synthesis of Compound 53

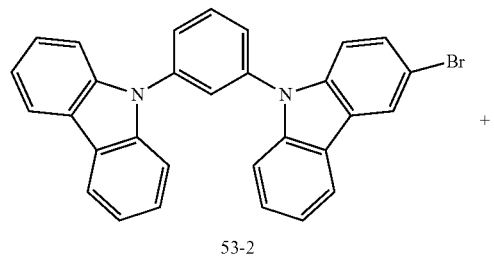

53-2

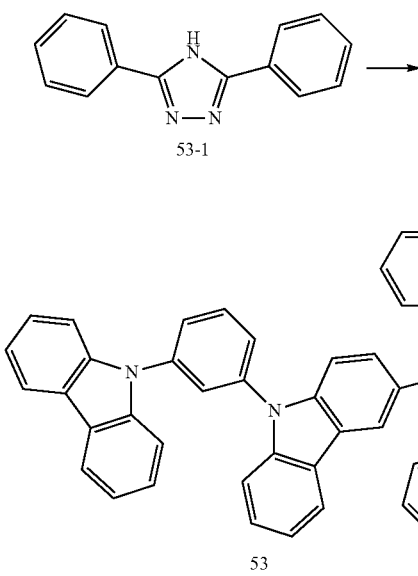

53-1

53

20 g of Intermediate 53-2, 11 g of Intermediate 53-1, 0.294 g of copper oxide, 18.718 g of cesium carbonate, 1.479 g of a ligand, 10 g of PEG, and DMF were added into a flask, and then the mixture was stirred at a temperature of 150° C. while refluxing. When the reaction was complete, a reaction product was cooled, and methanol was added thereto to form a precipitate. The precipitate was filtered, the filtered precipitate was completely dissolved in toluene while heating, and the resultant solution was filtered via a filter. A solvent was removed from the remaining solution, and the result was re-crystallized by using methylene chloride and hexane to obtain Compound 53 (13 g, yield: 50%), which was a white solid. Compound 53 was confirmed by LC-MS.

LC-Mass (calculated: 627.75 g/mol, found: M+H=628 g/mol).

Synthesis Example 2: Synthesis of Compound 55

(1) Synthesis of Intermediate 55-1

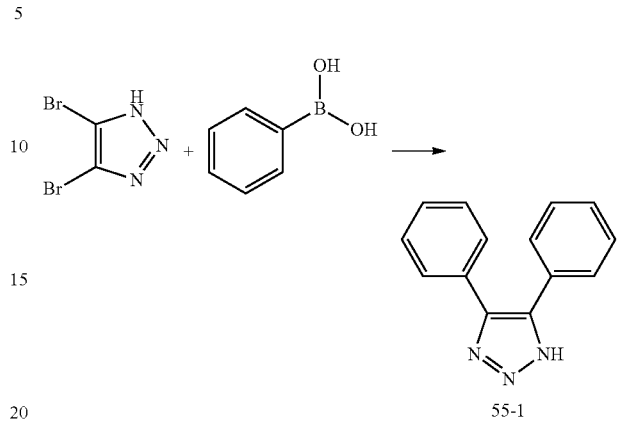

55-1

Intermediate 55-1 (13.5 g, yield: 80%) was obtained in the same manner as used to synthesize Intermediate 53-1, except that 4,5-dibromo-1H-1,2,3-triazole was used instead of 3,5-dibromo-4H-1,2,4-triazole.

(2) Synthesis of Compound 55

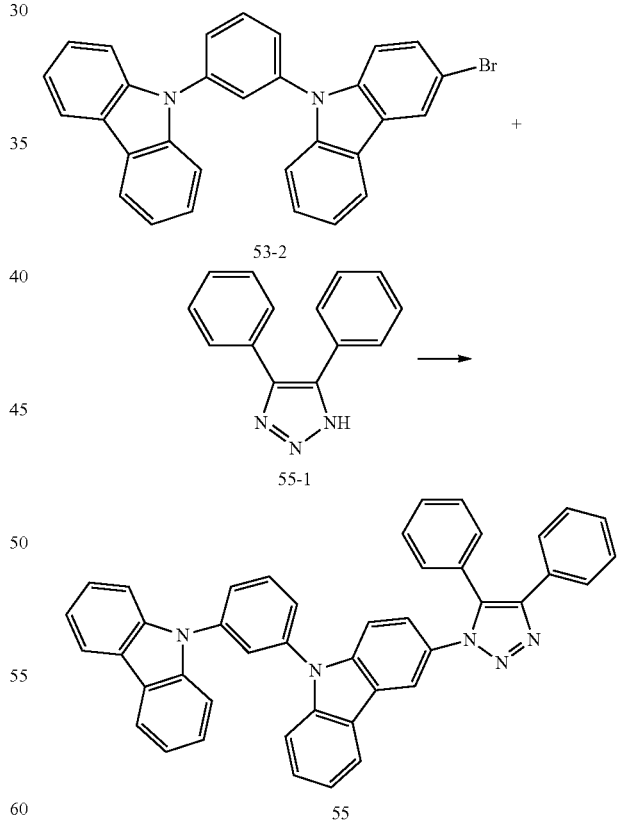

53-2

55-1

55

Compound 55 (8.12 g, 32%) was obtained in the same manner as in synthesizing Compound 53, except that Intermediate 55-1 was used instead of Intermediate 53-1. Compound 55 was confirmed by LC-MS.

LC-Mass (calculated: 627.75 g/mol, found: M+H=628 g/mol).

Evaluation Example 1

Evaluation on HOMO, LUMO, and Triplets (T1) Energy Levels

HOMO, LUMO and T1 energy levels of Compounds 53, 55, and A were evaluated according to the method indicated in Table 2, and results thereof are shown in Table 3.

TABLE 2

| | |
|---|---|
| HOMO energy level evaluation method | A potential (Volts, V)-current (Amperes, A) graph of each compound was obtained by using cyclic voltammetry (CV) (electrolyte: 0.1 molar (M) tetrabutylammonium perchlorate/solvent: acetonitrile/electrode: 3 electrode system (working electrode: carbon, reference electrode: Ag/AgCl, auxiliary electrode: Pt)). From reduction onset of the graph, a HOMO energy level of the compound was calculated. |
| LUMO energy level evaluation method | Each compound was diluted at a concentration of $1 \times 10^{-5}$ M in tetrahydrofuran (THF), and an UV absorption spectrum thereof was measured at room temperature by using a Shimadzu UV-350 spectrometer. The LUMO energy level thereof was calculated by using an optical band gap (Eg) from an edge of the absorption spectrum. |
| T1 energy level evaluation method | Each compound was diluted at a concentration of $1 \times 10^{-5}$ M by using THF, and loaded into a quartz cell. The resultant quartz cell was loaded into liquid nitrogen (77 Kelvins (K)) and a photoluminescence spectrum thereof was measured by using a device for measuring photoluminescence. The obtained spectrum was compared with a photoluminescence spectrum measured at room temperature, and peaks observed only at low temperature were analyzed to calculate T1 energy levels. |

TABLE 3

| Compound No. | HOMO (eV) (calc.) | LUMO (eV) (calc.) | T1 energy level (eV) |
|---|---|---|---|
| A | −5.73 | −2.17 | 3.00 |
| 53 | −5.67 | −2.16 | 3.00 |
| 55 | −5.68 | −2.28 | 2.82 |

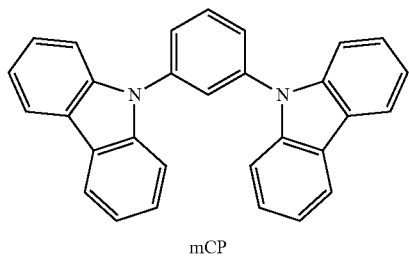

mCP

From Table 3, it is confirmed that the compounds above have electric characteristics that are suitable for use as a material for forming an organic light-emitting device.

Evaluation Example 2: Thermal Characteristics Evaluation

Figure 2:
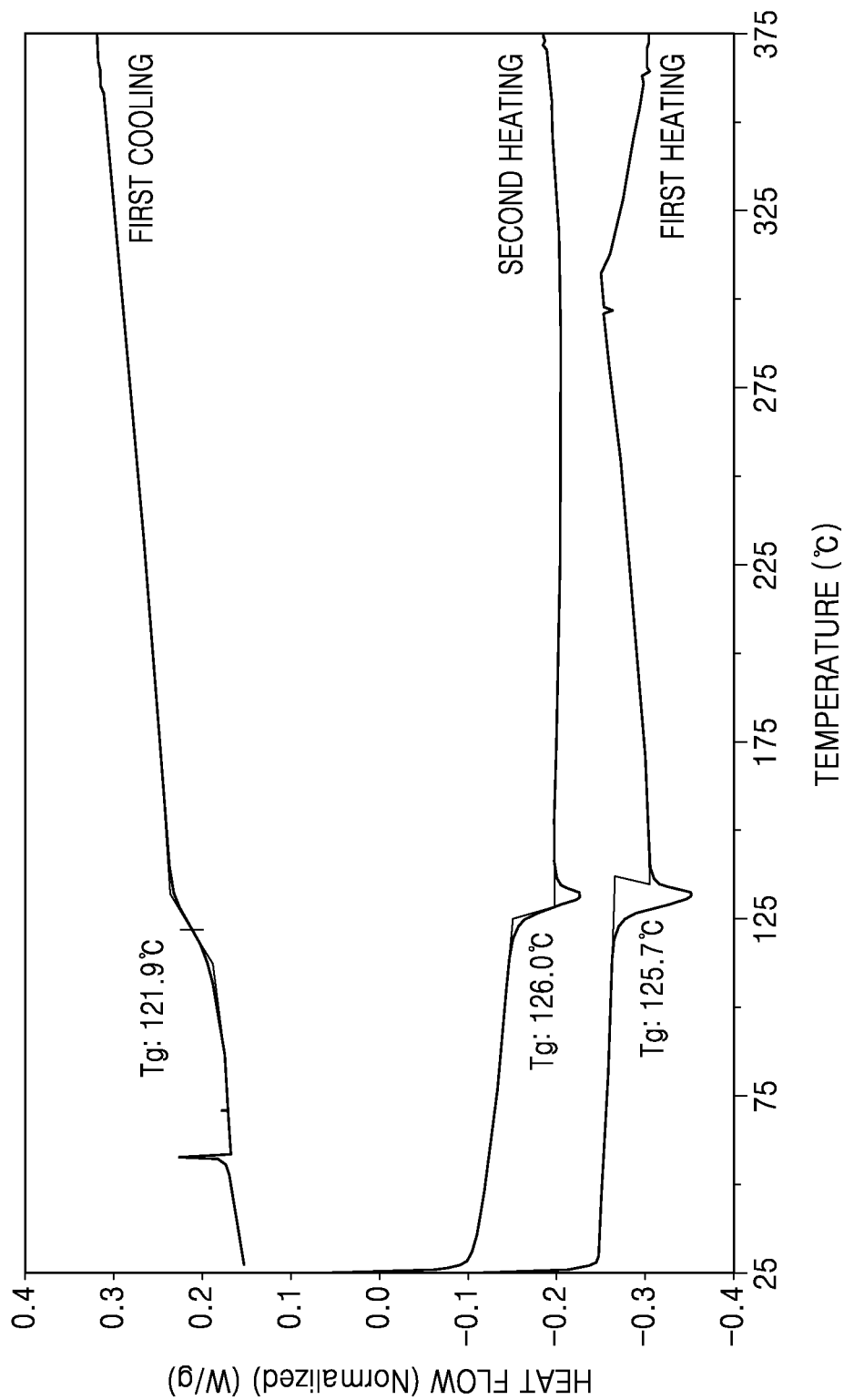
FIG. 2 is a graph of normalized heat flow (Watts per gram) versus temperature (degrees Centigrade, ° C.) showing differential scanning calorimetry (DSC) results of Compound 53 according to an embodiment.
Figure 3:
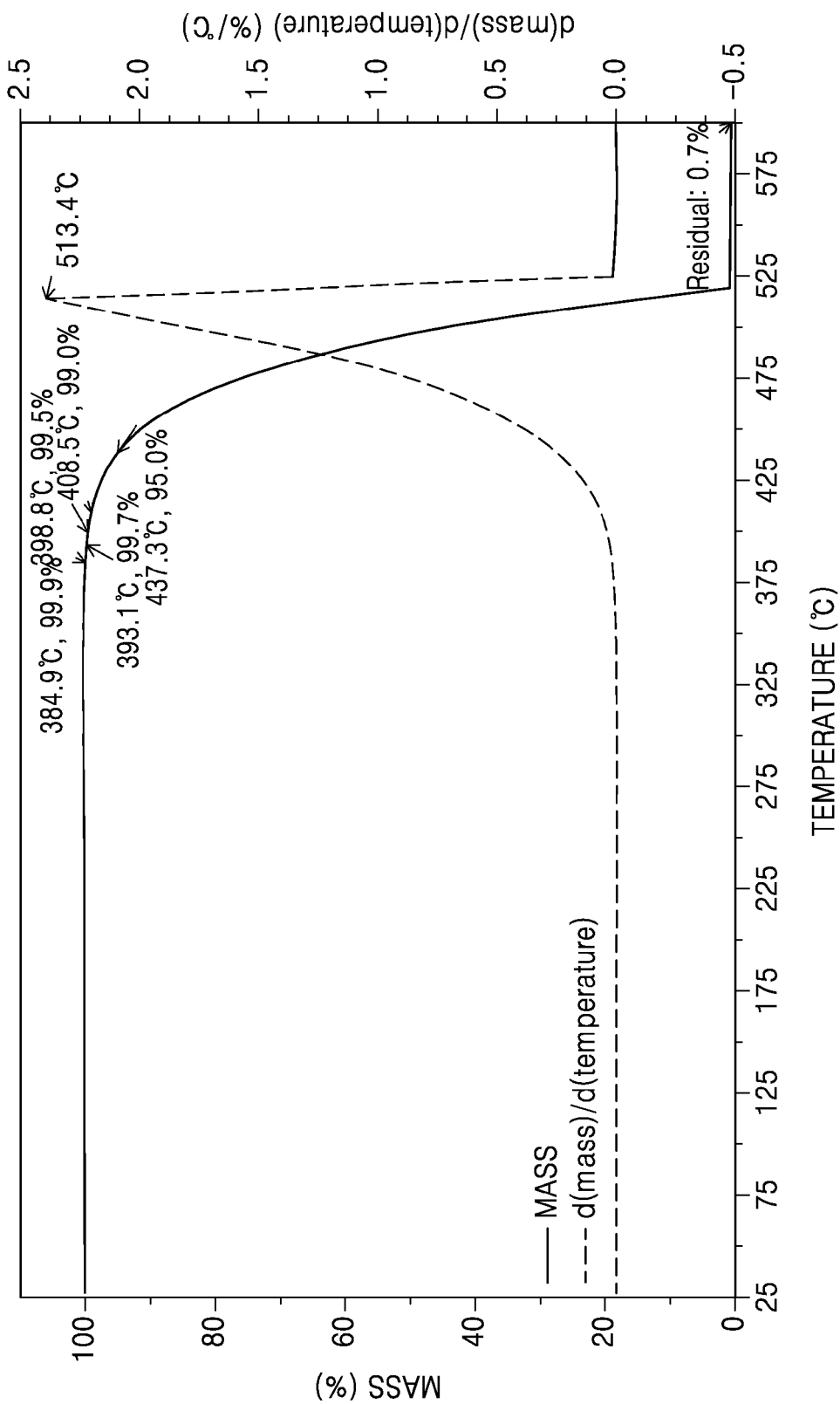
FIG. 3 is a graph of mass (percent, %) and d (mass)/d (temperature) (percent per degree Centigrade, %/° C.) versus temperature (degrees Centigrade, ° C.) showing thermogravimetric analysis (TGA) results of Compound 53 according to an embodiment.
Figure 4:
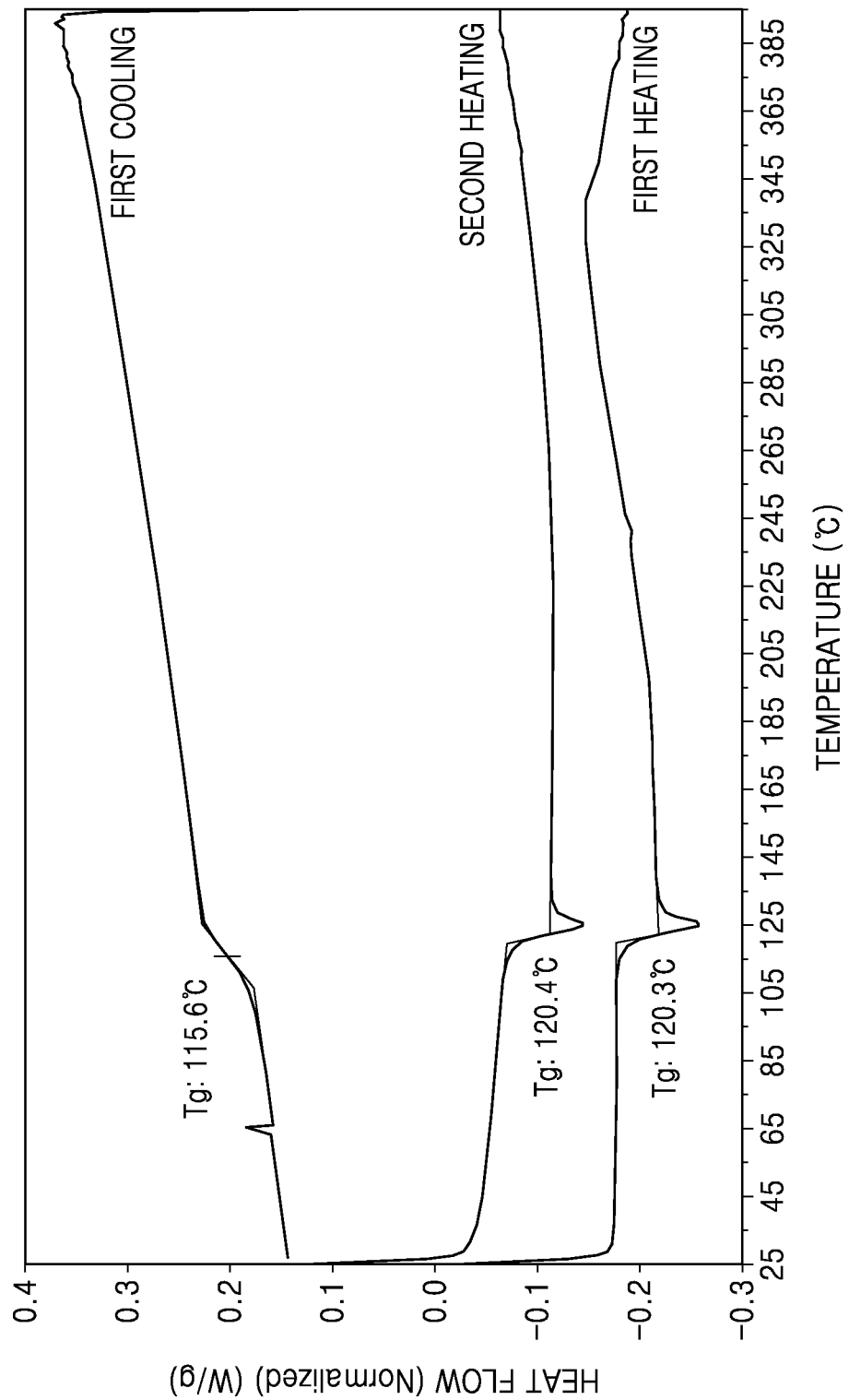
FIG. 4 is a graph of normalized heat flow (Watts per gram) versus temperature (degrees Centigrade, ° C.) showing DSC results of Compound 55 according to an embodiment.
Figure 5:
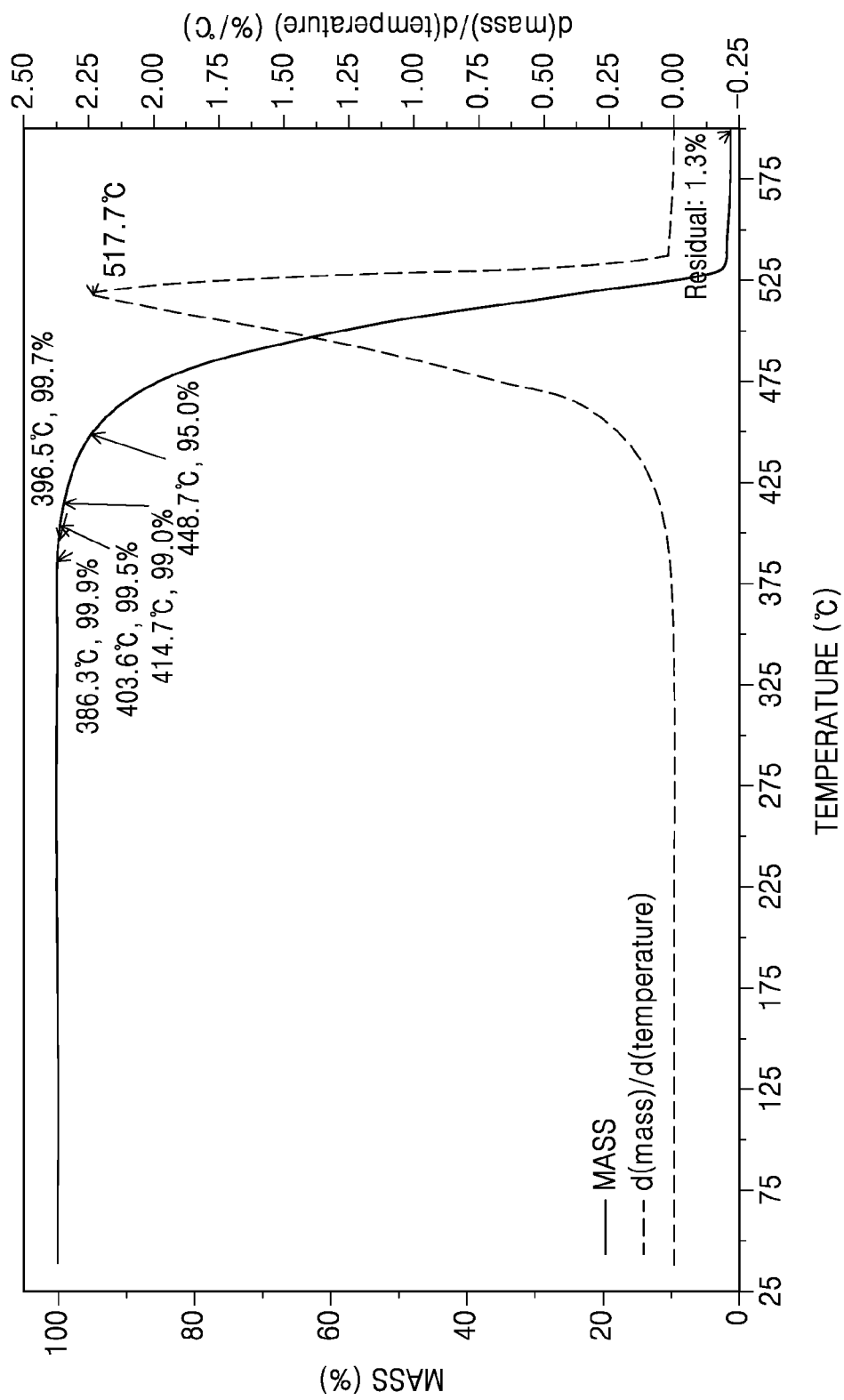
FIG. 5 is a graph of mass (percent, %) and d (mass)/d (temperature) (percent per degree Centigrade, %/° C.) versus temperature (degrees Centigrade, ° C.) showing TGA results of Compound 55 according to an embodiment.

Thermal analysis ($N_2$ atmosphere, temperature range: from room temperature to 800° C. (10° C./min)-TGA, from room temperature to 400° C.-DSC, Pan Type: Pt Pan in disposable Al Pan(TGA), and disposable Al pan(DSC)) was performed on Compounds 53, 55, and A by using thermogravimetric analysis (TGA) and differential scanning calorimetry (DSC), and results thereof are shown in Table 4. FIGS. 2 and 5 show thermal analysis results of Compounds 53 and 55. Referring to Table 4, and FIGS. 2-5, it was confirmed that the compounds had excellent thermal stability.

TABLE 4

| Compound No. | Tg (° C.) | Td (° C.) |
|---|---|---|
| A | 85 | — |
| 53 | 126 | 275 |
| 55 | 120 | 285 |

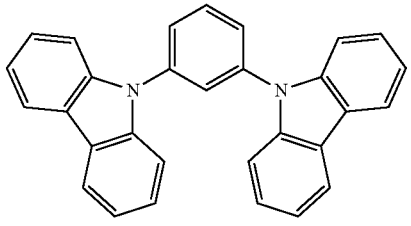

mCP

Example 1

ITO glass substrate (ITO layer acts as an anode) having a surface resistance of 15 Ohms per square centimeter (Q/cm²) was cut to a size of 50 millimeters (mm)×50 mm×0.7 mm, sonicated with acetone, isopropyl alcohol, and pure water, for 15 minutes in each solvent, and cleaned with UV ozone for 30 minutes.

On the ITO anode, NPB was deposited at a vacuum of $650 \times 10^{-7}$ Pascals (Pa) and at a deposition speed of 0.1 to 0.3 nanometers per second (nm/s) to form a hole injection layer having a thickness of 700 Å, and mCP was deposited on the hole injection layer to form an electron blocking layer having a thickness of 50 Å to form a hole transport region.

On the hole transport region, Compound 53 (host) and compound Flr6 (dopant, 10 wt %) were co-deposited to form an emission layer having a thickness of 300 Å.

TmPyPB was vacuum-deposited on the emission layer to form a hole blocking layer having a thickness of 300 Å, Alq₃ was vacuum-deposited on the hole blocking layer to form an electron transport layer having a thickness of 100 Å, and LiQ was deposited on the electron transport layer to form an electron injection layer having a thickness of 5 Å, and an Al second electrode (cathode) having a thickness of 1,000 Å was formed on the electron injection layer to complete manufacturing of an organic light-emitting device.

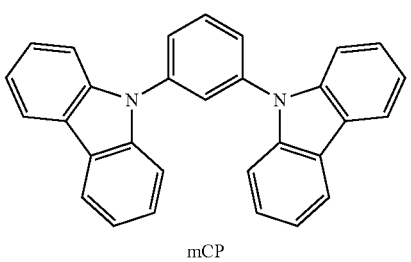

mCP

-continued

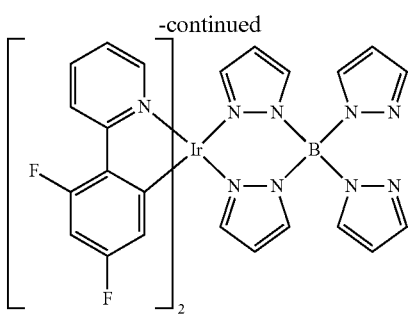

FIr6

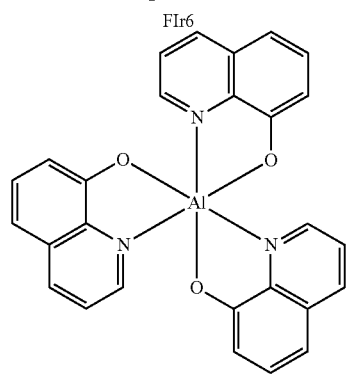

Alq₃

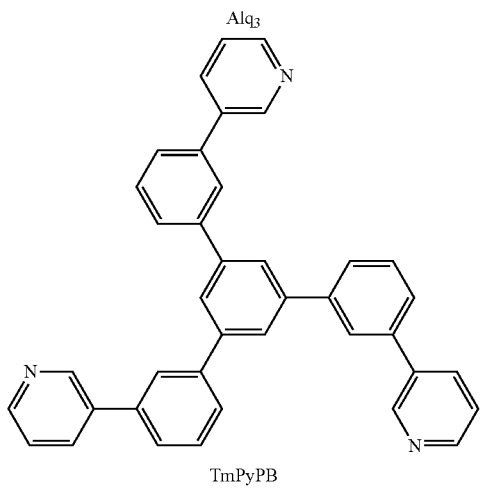

TmPyPB

Example 2

An organic light-emitting device was manufactured in the same manner as in Example 1, except that in forming an emission layer, as a host, Compound 55 was used instead of Compound 53.

Comparative Example 1

An organic light-emitting device was manufactured in the same manner as in Example 53, except that in forming an emission layer, as a host, Compound A was used instead of Compound 1.

Compound A

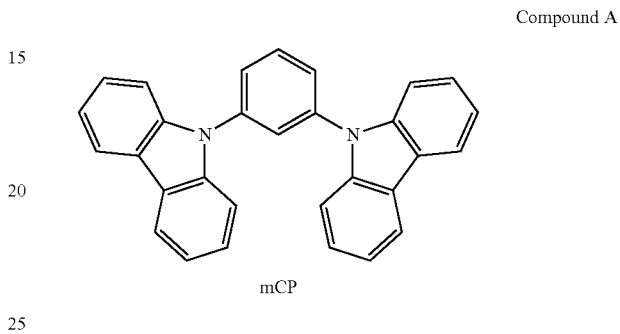

mCP

Evaluation Example 3: Evaluation on Characteristics of Organic Light-Emitting Devices The driving voltage, current efficiency, power efficiency, and lifespan of the organic light-emitting devices manufactured according to Examples 1, 2, and Comparative Example 1 were measured by using a current-voltage meter (Keithley 2400) and a brightness meter (Minolta Cs-1000A). Results thereof are shown in Table 5.

In Table 5, $T_{95}$ (at 500 candelas per square meter ($cd/m^2$)) indicates lifespan data evaluated by measuring the amount of time that elapsed until brightness was reduced to 95% of the initial brightness of 100%.

In Table 5, the driving voltage, current density, quantum efficiency, and lifespan ($T_{95}$) of the organic light-emitting devices of Examples 1 and 2 are values relative to the driving voltage, current density, quantum efficiency, and lifespan ($T_{95}$) of the organic light-emitting device of Comparative Example 1. The driving voltage, current density, quantum efficiency, and lifespan ($T_{95}$) of the organic light-emitting device of Comparative Example 1 were regarded as "100."

TABLE 5

| | Host | Driving voltage (relative value) | Current density (relative value) | Quantum efficiency (relative value) | lifespan ($T_{95}$) (relative value) | Emission color |
|---|---|---|---|---|---|---|
| Example 1 | Compound 53 | 88 | 175 | 124 | 161 | Blue |
| Example 2 | Compound 55 | 96 | 148 | 101 | 108 | Blue |
| Comparative Example 1 | Compound A | 100 | 100 | 100 | 100 | Blue |

The condensed cyclic compounds according to embodiments have excellent electric characteristics and thermal stability. Accordingly, organic light-emitting devices including the condensed cyclic compounds may have a low driving voltage, high efficiency, high brightness, long lifespan, and high color purity.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A condensed cyclic compound represented by Formula 1:

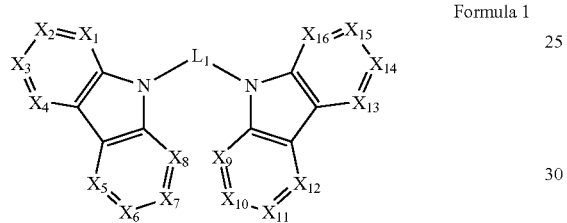

Formula 1 wherein in Formula 1, $L_1$ is selected from a phenylene group, a pyridinylene group, a pyrimidinylene group, and a triazinylene group;

$X_1$ is N or $CR_1$;
$X_2$ is N or $CR_2$;
$X_3$ is N or $CR_3$;
$X_4$ is N or $CR_4$;
$X_5$ is N or $CR_5$;
$X_6$ is N or $CR_6$;
$X_7$ is N or $CR_7$;
$X_8$ is N or $CR_8$;
$X_9$ is N or $CR_9$;
$X_{10}$ is N or $CR_{10}$;
$X_{11}$ is N or $CR_{11}$;
$X_{12}$ is N or $CR_{12}$;
$X_{13}$ is N or $CR_{13}$;
$X_{14}$ is N or $CR_{14}$;
$X_{15}$ is N or $CR_{15}$;
$X_{16}$ is N or $CR_{16}$;

$R_1$ to $R_{16}$ are each independently selected from $R_{ET}$, a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_1$-$C_{60}$ alkoxy group, a substituted or unsubstituted $C_3$-$C_{10}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

at least one selected from $X_1$ to $X_{16}$ is $CR_{ET}$;

$R_{ET}$ is represented by any one of Formulae 2-1 to 2-8:

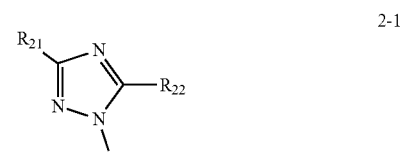

2-1

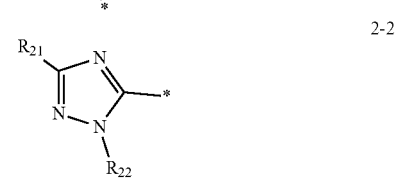

2-2

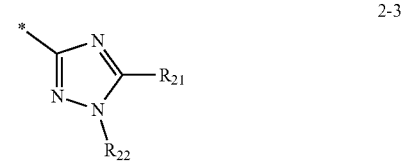

2-3

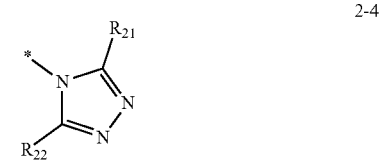

2-4

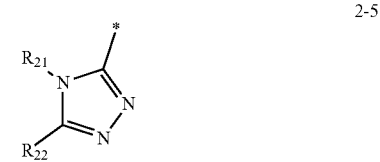

2-5

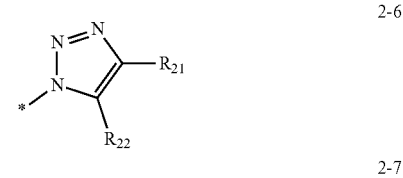

2-6

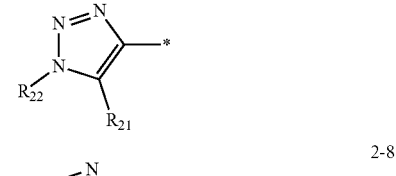

2-7

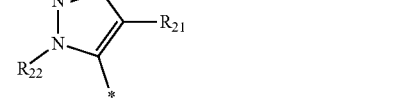

2-8 wherein in Formulae 2-1 to 2-8, $R_{21}$ and $R_{22}$ are each independently selected from a substituted $C_1$-$C_{60}$ alkyl group, a substituted $C_1$-$C_{60}$ alkoxy group, a substituted $C_3$-$C_{10}$ cycloalkyl group, a substituted or unsubstituted $C_6$-$C_{60}$ aryl group, a substituted $C_6$-$C_{60}$ aryloxy group, a substituted $C_6$-$C_{60}$ arylthio group, a substituted unsubstituted $C_1$-$C_{60}$ heteroaryl group, a substituted monovalent non-aromatic condensed polycyclic group, and a substituted monovalent non-aromatic condensed heteropolycyclic group;
* indicates a binding site to a neighboring atom, and
at least one of substituents of the substituted $C_1$-$C_{60}$ alkyl group, substituted $C_1$-$C_{60}$ alkoxy group, substituted $C_3$-$C_{10}$ cycloalkyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from
a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_1$-$C_{60}$ alkenyl group, a $C_1$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$); and
—Si($Q_{31}$)($Q_{32}$)($Q_{33}$),
wherein $Q_{11}$ to $Q_{13}$, $Q_{21}$ to $Q_{23}$ and $Q_{31}$ to $Q_{33}$ are each independently selected from a $C_1$-$C_{60}$ alkyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The condensed cyclic compound of claim 1, wherein $L_1$ is selected from Formulae 3-1 to 3-14;

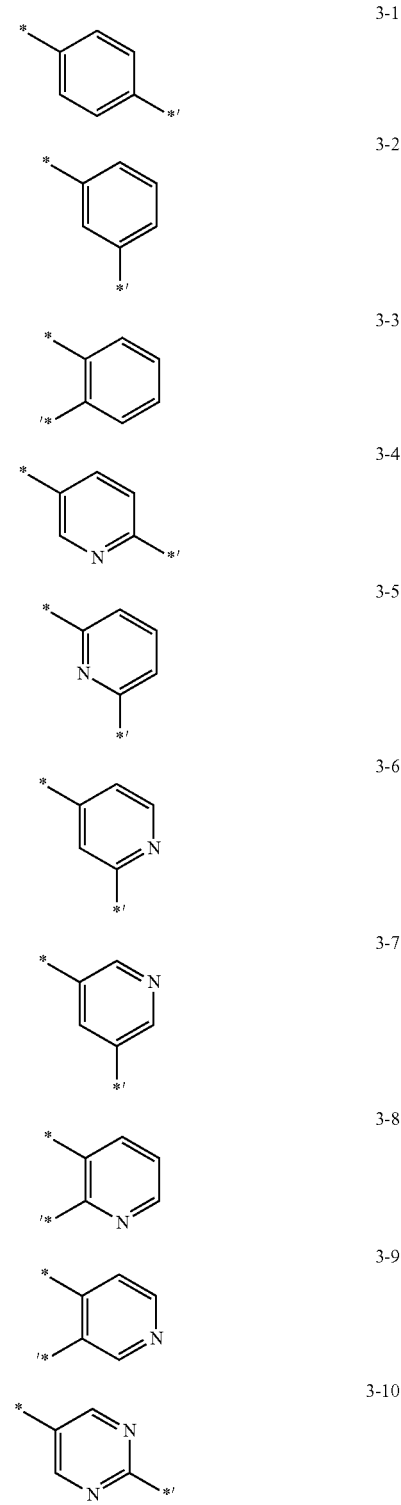

-continued 3-11
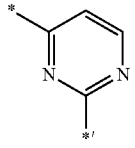

3-12
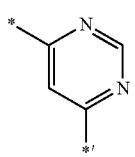

3-13
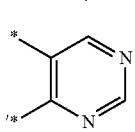

3-14
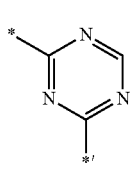

wherein in Formulae 3-1 to 3-14,

* and *' indicate each independently a binding site to a neighboring atom.

3. The condensed cyclic compound of claim 1, wherein $L_1$ is selected from Formulae 3-2, 3-5, 3-6, 3-7, 3-11, 3-12, and 3-14:

3-1
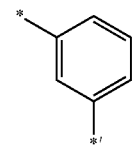

3-2
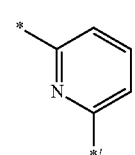

3-3
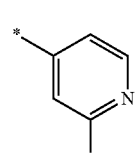

3-4
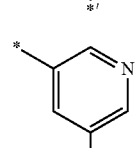

3-5
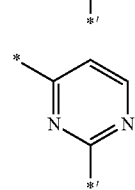

-continued 3-6
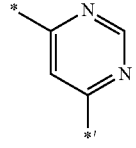

3-7
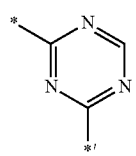

wherein in Formulae 3-2, 3-5, 3-6, 3-7, 3-11, 3-12, and 3-14,

* and *' indicate each independently a binding site to a neighboring atom.

4. The condensed cyclic compound of claim 1, wherein
$X_1$ is $CR_1$ $X_2$ is $CR_2$; $X_3$ is $CR_3$; $X_4$ is $CR_4$; $X_5$ is $CR_5$; $X_6$ is $CR_6$; $X_7$ is $CR_7$; $X_8$ is $CR_8$; $X_9$ is $CR_9$; $X_{10}$ is $CR_{10}$; $X_{11}$ is $CR_{11}$; $X_{12}$ is $CR_{12}$; $X_{13}$ is $CR_{13}$; $X_{14}$ is $CR_{14}$; $X_{15}$ is $CR_{15}$; and $X_{16}$ is $CR_{16}$, or
$X_1$ is N; $X_2$ is $CR_2$; $X_3$ is $CR_3$; $X_4$ is $CR_4$; $X_5$ is $CR_5$; $X_6$ is $CR_6$; $X_7$ is $CR_7$; $X_8$ is $CR_8$; $X_9$ is $CR_9$; $X_{10}$ is $CR_{10}$; $X_{11}$ is $CR_{11}$; $X_{12}$ is $CR_{12}$; $X_{13}$ is $CR_{13}$; $X_{14}$ is $CR_{14}$; $X_{15}$ is $CR_{15}$; and $X_{16}$ is $CR_{16}$, or
$X_1$ is $CR_1$; $X_2$ is N; $X_3$ is $CR_3$; $X_4$ is $CR_4$; $X_5$ is $CR_5$; $X_6$ is $CR_6$; $X_7$ is $CR_7$; $X_8$ is $CR_8$; $X_9$ is $CR_9$; $X_{10}$ is $CR_{10}$; $X_{11}$ is $CR_{11}$; $X_{12}$ is $CR_{12}$; $X_{13}$ is $CR_{13}$; $X_{14}$ is $CR_{14}$; $X_{15}$ is $CR_{15}$; and $X_{16}$ is $CR_{16}$, or
$X_1$ is N; $X_2$ is $CR_2$; $X_3$ is $CR_3$; $X_4$ is $CR_4$; $X_5$ is $CR_5$; $X_6$ is $CR_6$; $X_7$ is $CR_7$; $X_8$ is N; $X_9$ is $CR_9$; $X_{10}$ is $CR_{10}$; $X_{11}$ is $CR_{11}$; $X_{12}$ is $CR_{12}$; $X_{13}$ is $CR_{13}$; $X_{14}$ is $CR_{14}$; $X_{15}$ is $CR_{15}$; and $X_{16}$ is $CR_{16}$, or
$X_1$ is $CR_1$; $X_2$ is N; $X_3$ is $CR_3$; $X_4$ is $CR_4$; $X_5$ is $CR_5$; $X_6$ is $CR_6$; $X_7$ is N; $X_8$ is $CR_8$; $X_9$ is $CR_9$; $X_{10}$ is $CR_{10}$; $X_{11}$ is $CR_{11}$; $X_{12}$ is $CR_{12}$; $X_{13}$ is $CR_{13}$; $X_{14}$ is $CR_{14}$; $X_{15}$ is $CR_{15}$; and $X_{16}$ is $CR_{16}$.

5. The condensed cyclic compound of claim 1, wherein $R_1$ to $R_{16}$ in Formula 1 are each independently selected from $R_{ET}$, a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, an n-pentyl group, an n-hexyl group, a methoxy group, an ethoxy group, an n-propoxy group, an iso-propoxy group, an n-butoxy group, a tert-butoxy group, a cyclopentyl group, a cyclohexyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a methyl group, an ethyl group, an n-propyl group, an iso-propyl group, an n-butyl group, an iso-butyl group, a sec-butyl group, a tert-butyl group, an n-pentyl group, an n-hexyl group, a methoxy group, an ethoxy group, an n-propoxy group, an iso-propoxy group, an n-butoxy group, a tert-butoxy group, a cyclopentyl group, a cyclohexyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group.

6. The condensed cyclic compound of claim 1, wherein $R_1$ to $R_{16}$ are each independently selected from $R_{ET}$, a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group, and a dibenzothiophenyl group; and a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group and a dibenzothiophenyl group, each substituted with at least one selected from a deuterium, —F, —Cl, —Br, —I, a hydroxyl group, a cyano group, a nitro group, a $C_1$-$C_{60}$ alkyl group, a phenyl group, a naphthyl group, a pyridinyl group, a pyrimidinyl group, and a triazinyl group.

7. The condensed cyclic compound of claim 1, wherein one or two selected from $X_1$ to $X_{16}$ are $CR_{ET}$.

8. The condensed cyclic compound of claim 1, wherein one selected from $X_1$ to $X_{16}$ is $R_{ET}$.

9. The condensed cyclic compound of claim 1, wherein $X_{14}$ is $CR_{ET}$.

10. The condensed cyclic compound of claim 1, wherein $R_{ET}$ is a group represented by any one of Formulae 2-1, 2-3, 2-4, and 2-6.

11. The condensed cyclic compound of claim 1, wherein $R_{21}$ and $R_{22}$ are each independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group.

12. The condensed cyclic compound of claim 1, wherein $R_{21}$ and $R_{22}$ are each independently selected from a group represented by Formulae 4-1 to 4-11:

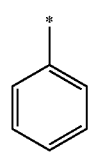

4-1

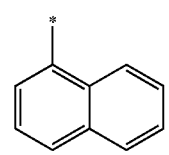

4-2

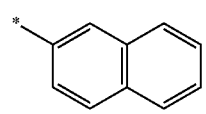

4-3

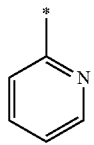

4-4

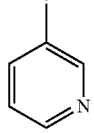

4-5

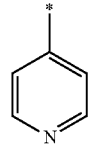

4-6

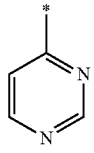

4-7

-continued
4-8
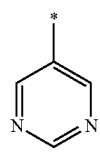
4-9
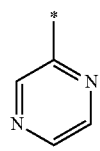
4-10
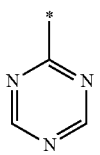
4-11
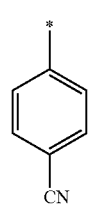
wherein in Formulae 4-1 to 4-11,
* indicates a binding site to a neighboring atom.
13. The condensed cyclic compound of claim 1, wherein $R_{ET}$ is a group represented by any one of Formulae 5-1 to 5-24:
5-1
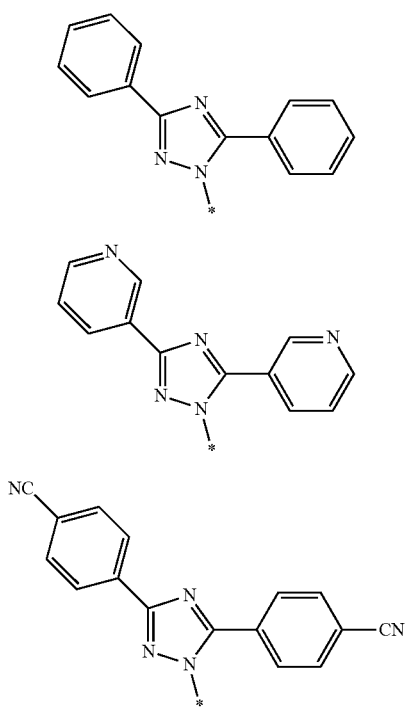
-continued
5-4
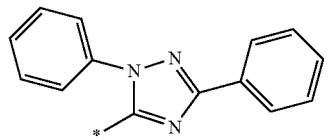
5-5
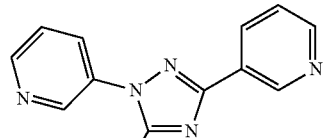
5-6
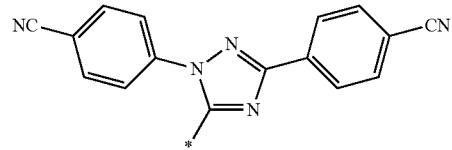
5-7
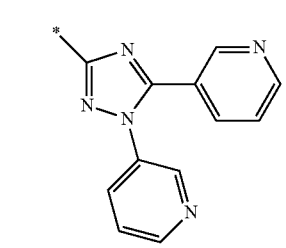
5-8
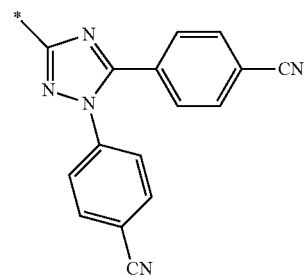
5-9
5-10
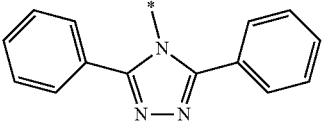
5-11
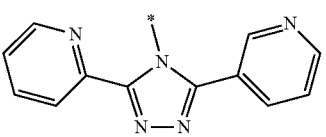

5-12 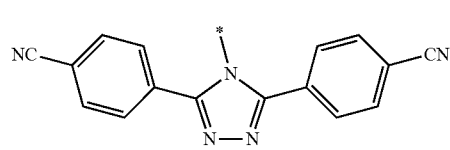
5-13 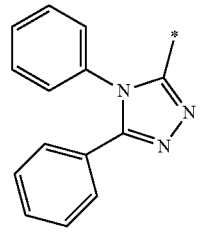
5-14 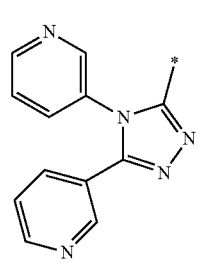
5-15 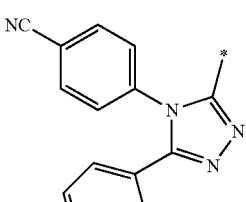
5-16 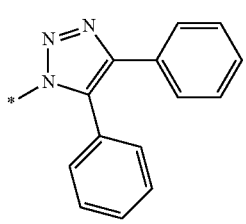
5-17 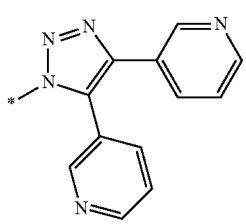
5-18 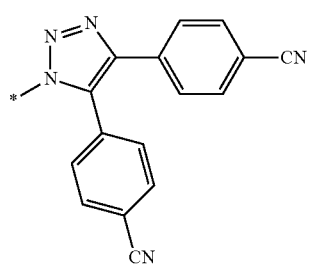
5-19 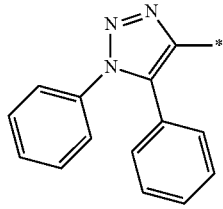
5-20 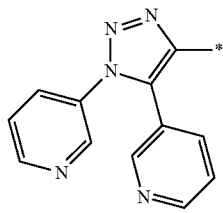
5-21 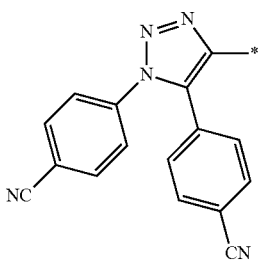
5-22 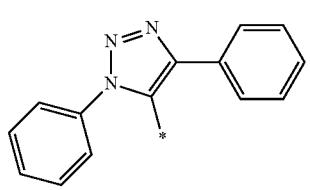
5-23 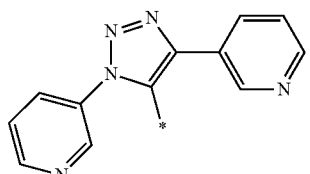
5-24 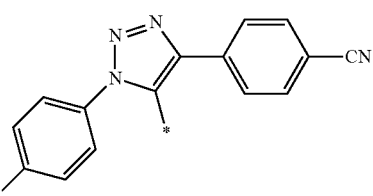
wherein in Formulae 5-1 to 5-24,
* indicates a binding site to a neighboring atom.
14. The condensed cyclic compound of claim 1, wherein the condensed cyclic compound represented by one of Formulae 1A to 1E:

Formula 1A

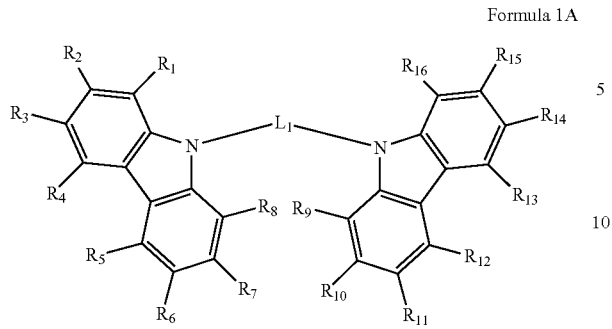

Formula 1B

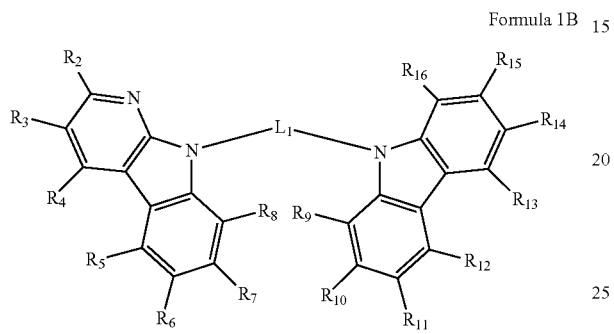

Formula 1C

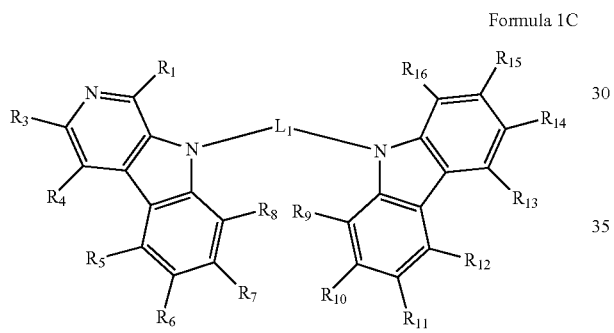

Formula 1D

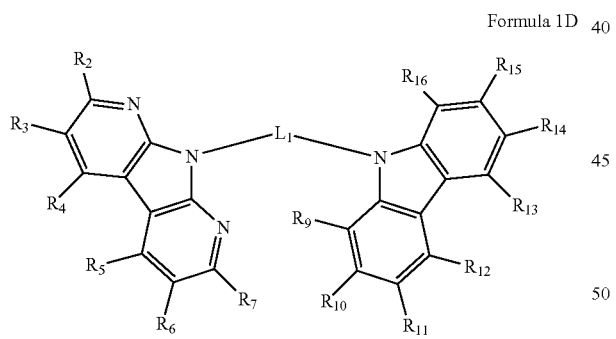

Formula 1E

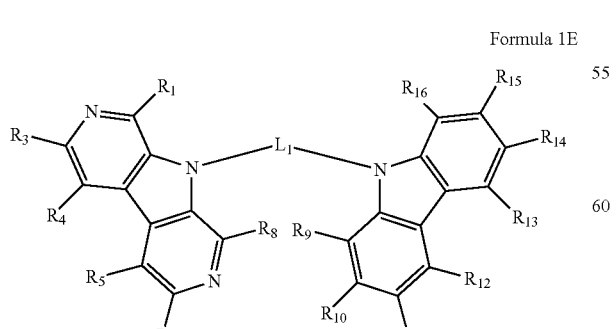

in Formulae 1A to 1E, $L_1$ is selected from a phenylene group, a pyridinylene group, a pyrimidinylene group, and a triazinylene group;

$R_1$ to $R_{16}$ are each independently selected from $R_{ET}$, a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group, and a dibenzothiophenyl group; and a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group and a dibenzothiophenyl group, each substituted with at least one selected from a deuterium, —F, —Cl, —Br, —I, a hydroxyl group, a cyano group, a nitro group, a $C_1$-$C_{60}$ alkyl group, a phenyl group, a naphthyl group, a pyridinyl group, a pyrimidinyl group, and a triazinyl group;

at least one selected from $R_1$ to $R_{16}$ is $R_{ET}$;

$R_{ET}$ is represented by any one of Formulae 2-1 to 2-8:

2-1

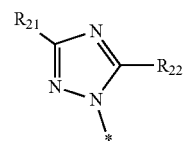

2-2

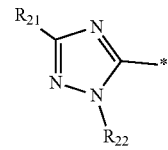

2-3

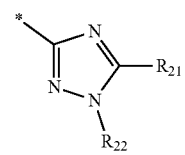

2-4

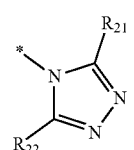

2-5

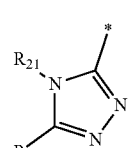

-continued

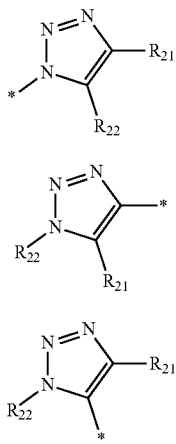

2-6

2-7

2-8 wherein in Formulae 2-1 to 2-8,
$R_{21}$ and $R_{22}$ are each independently selected from a phenyl group, a naphthyl group, a fluorenyl group, a pyridinyl group, a pyrimidinyl group, a pyridazinyl group, and a triazinyl group; and
a phenyl group, a naphthyl group, a fluorenyl group, a pyridinyl group, a pyrimidinyl group, a pyridazinyl group, and a triazinyl group, each substituted with at least one selected from a deuterium, —F, —Cl, —Br, —I, a hydroxyl group, a cyano group, a nitro group, a $C_1$-$C_{60}$ alkyl group, a phenyl group, a naphthyl group, a pyridinyl group, a pyrimidinyl group, and a triazinyl group;
* indicates a binding site to a neighboring atom.

15. The condensed cyclic compound of claim 14, wherein $R_1$ to $R_{13}$, $R_{15}$, and $R_{16}$ are each independently selected from a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group, and a dibenzothiophenyl group; and
a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group and a dibenzothiophenyl group, each substituted with at least one selected from a deuterium, —F, —Cl, —Br, —I, a hydroxyl group, a cyano group, a nitro group, a $C_1$-$C_{60}$ alkyl group, a phenyl group, a naphthyl group, a pyridinyl group, a pyrimidinyl group, and a triazinyl group; and
$R_{14}$ is $R_{ET}$.

16. The condensed cyclic compound of claim 1, wherein the condensed cyclic compound is represented by any one of Formulae 1-1 to 1-9:

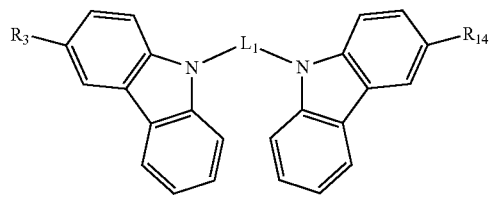

Formula 1-1

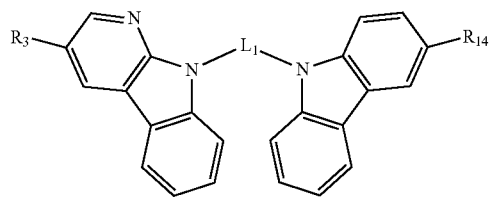

Formula 1-2

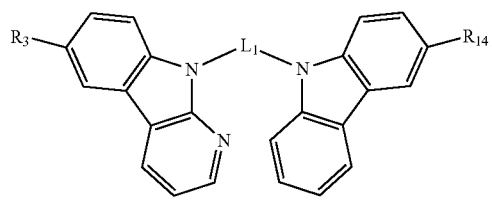

Formula 1-3

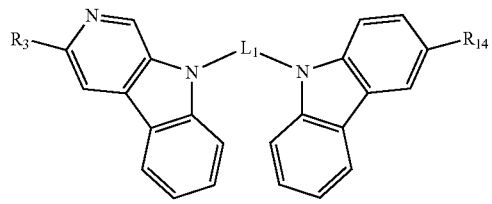

Formula 1-4

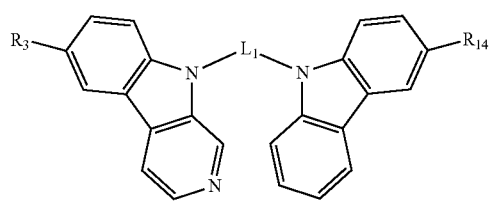

Formula 1-5

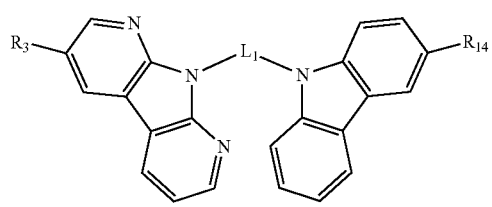

Formula 1-6

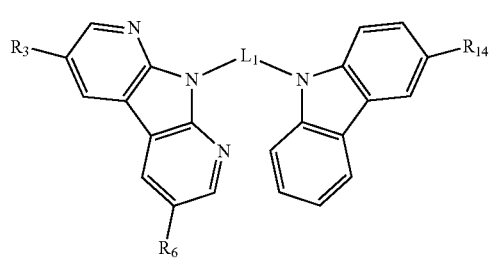

Formula 1-7

Formula 1-8

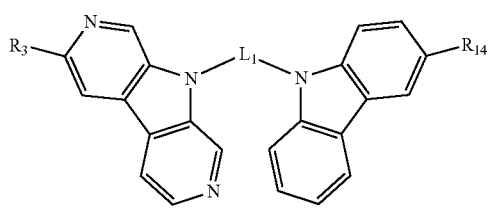

Formula 1-9

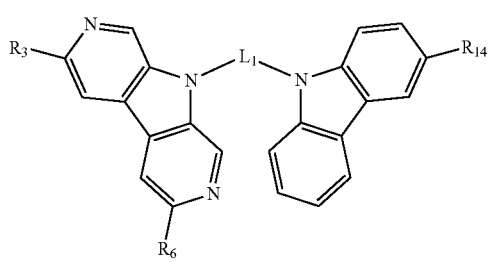

wherein in Formulae 1-1 to 1-9, $L_1$ is selected from a phenylene group, a pyridinylene group, a pyrimidinylene group, and a triazinylene group;

$R_3$, $R_6$, and $R_{14}$ are each independently selected from $R_{ET}$, a hydrogen, a deuterium, —F, —Cl, —Br, —I, a hydroxyl group, a cyano group, a nitro group, a methyl group, an ethyl group, an n-propyl group, an iso-propyl group, an n-butyl group, an iso-butyl group, a sec-butyl group, a tert-butyl group, a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group, and a dibenzothiophenyl group; and a phenyl group, a naphthyl group, a fluorenyl group, an anthracenyl group, a triphenylenyl group, a pyrrolyl group, a thiophenyl group, a furanyl group, a pyridinyl group, a pyrimidinyl group, a pyridazinyl group, an indolyl group, a quinolinyl group, an isoquinolinyl group, a carbazolyl group, a benzofuranyl group, a benzothiophenyl group, a triazolyl group, a triazinyl group, a dibenzofuranyl group and a dibenzothiophenyl group, each substituted with at least one selected from a deuterium, —F, —Cl, —Br, —I, a hydroxyl group, a cyano group, a nitro group, a $C_1$-$C_{20}$ alkyl group, a phenyl group, a naphthyl group, a pyridinyl group, a pyrimidinyl group, and a triazinyl group;

at least one selected from $R_3$, $R_6$, and $R_{14}$ is $R_{ET}$;

$R_{ET}$ is represented by any one of Formulae 2-1 to 2-8:

2-1

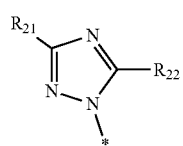

2-2

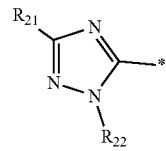

2-3

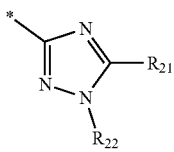

2-4

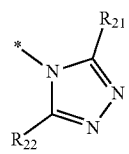

2-5

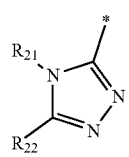

2-6

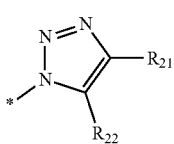

2-7

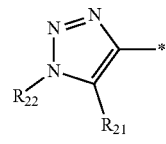

2-8

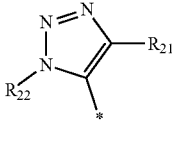

wherein in Formulae 2-1 to 2-8, $R_{21}$ and $R_{22}$ are each independently selected from a phenyl group, a naphthyl group, a fluorenyl group, a pyridinyl group, a pyrimidinyl group, a pyridazinyl group, and a triazinyl group; and a phenyl group, a naphthyl group, a fluorenyl group, a pyridinyl group, a pyrimidinyl group, a pyridazinyl group, and a triazinyl group, each substituted with at least one selected from a deuterium, —F, —Cl, —Br, —I, a hydroxyl group, a cyano group, a nitro group, a $C_1$-$C_{60}$ alkyl group, a phenyl group, a naphthyl group, a pyridinyl group, a pyrimidinyl group, and a triazinyl group, and

* indicates a binding site to a neighboring atom.

17. The condensed cyclic compound of claim 1, wherein the condensed cyclic compound is one of Compounds 1 to 107:

133 134
-continued
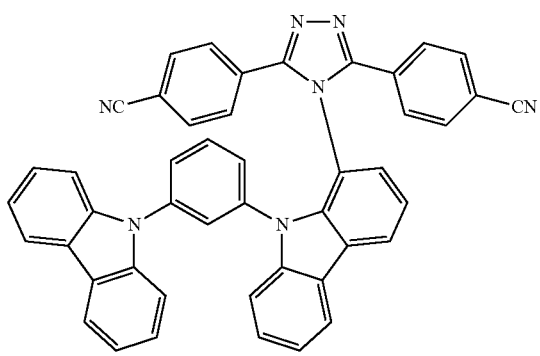
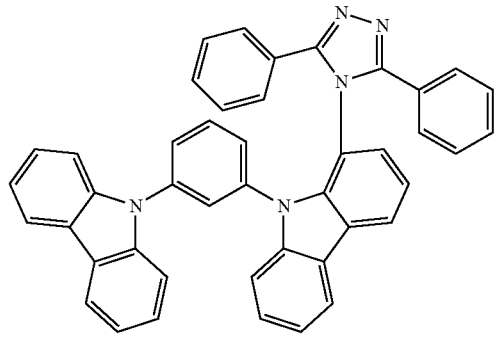
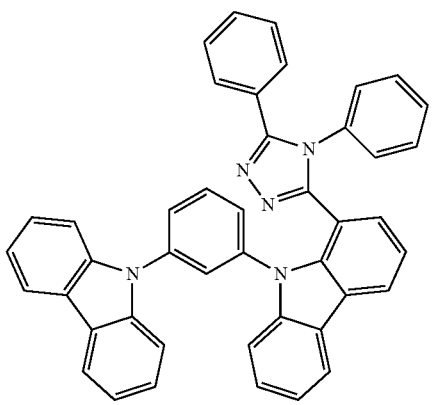
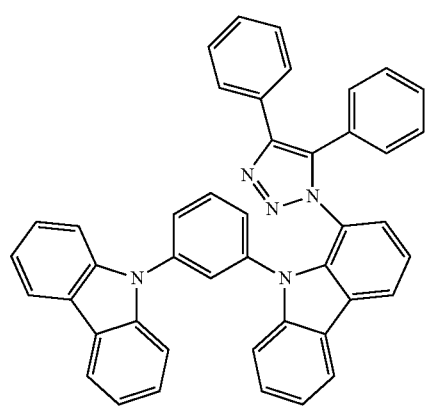
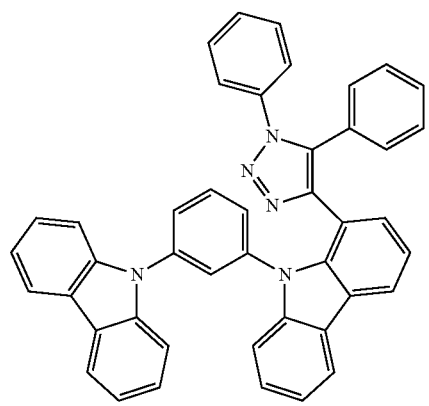

9
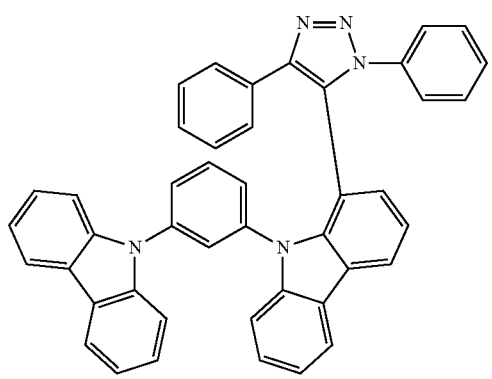
10
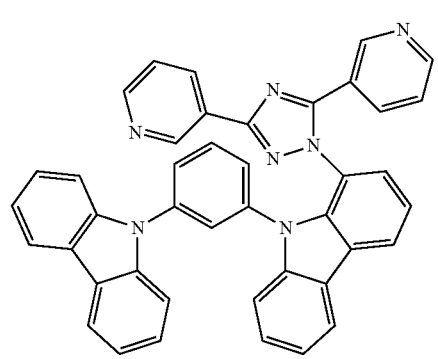
11
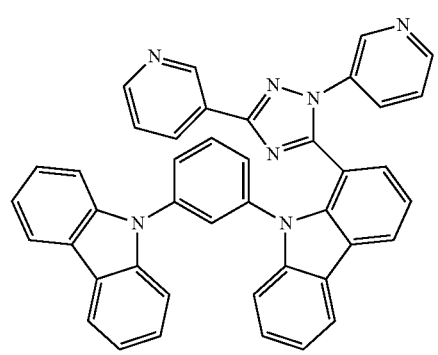
12
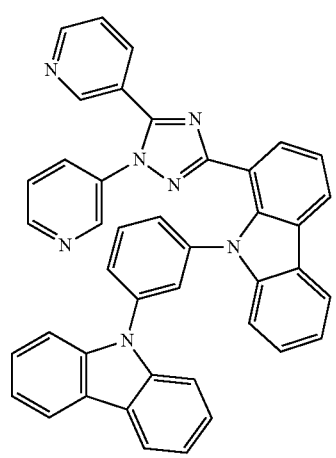
13
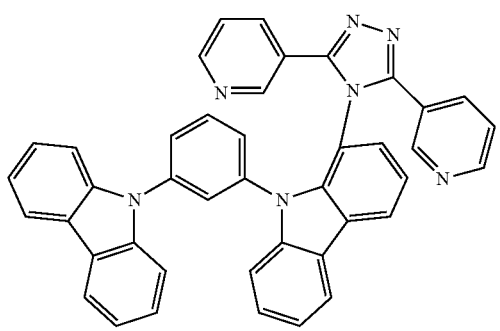
14
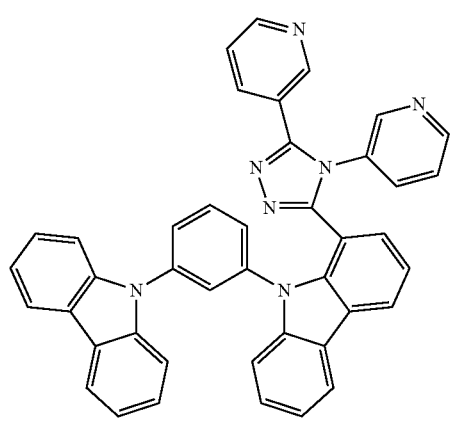
15
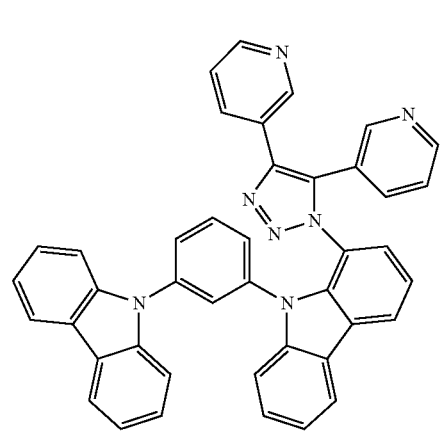
16
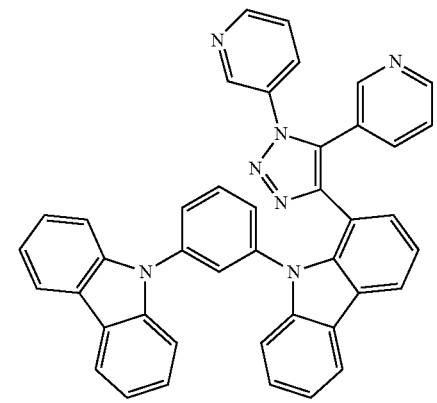

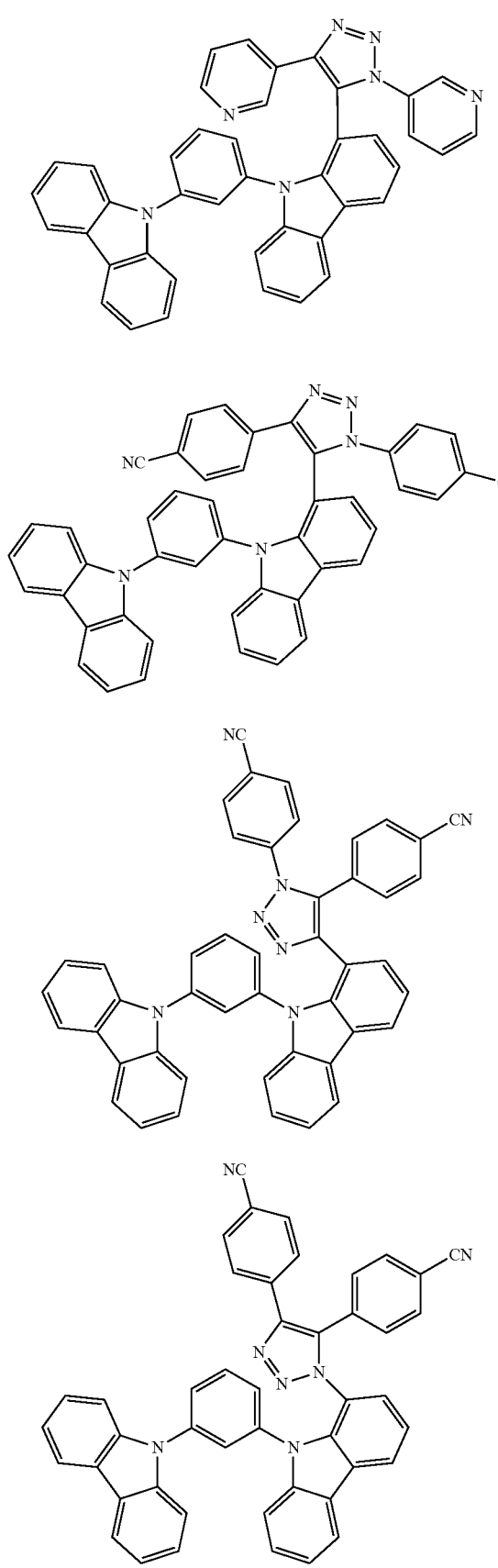
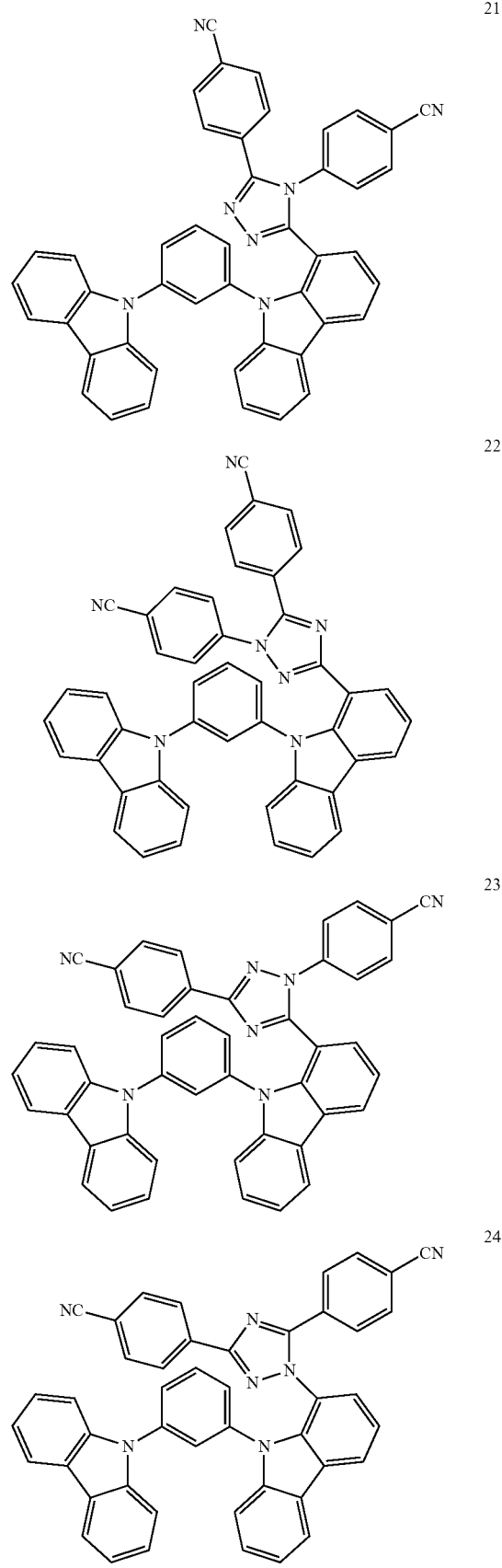

25
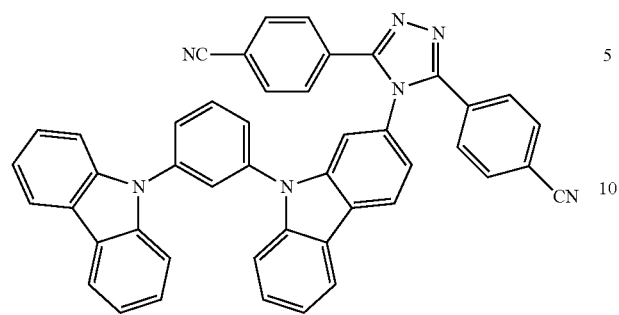
26
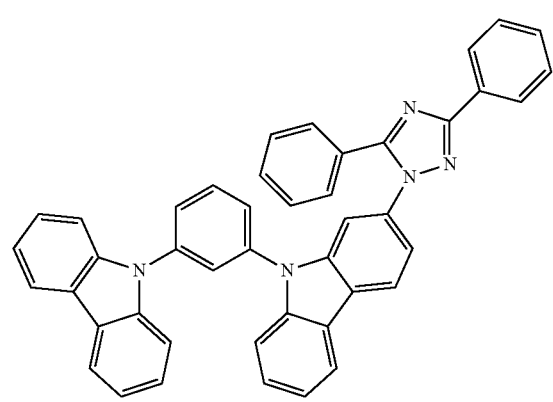
27
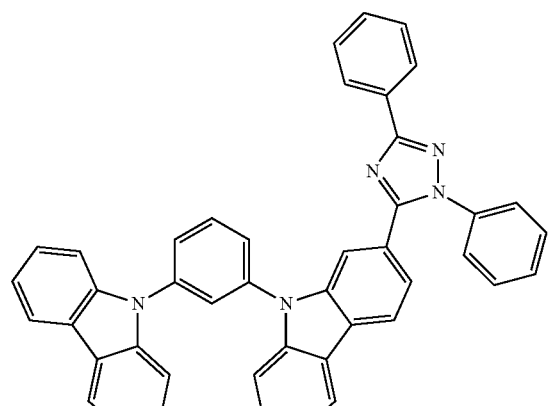
28
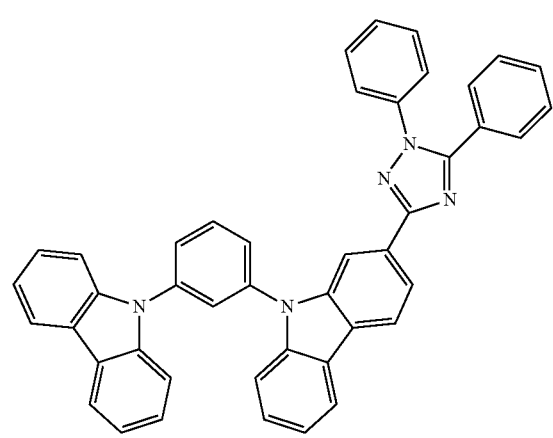
29
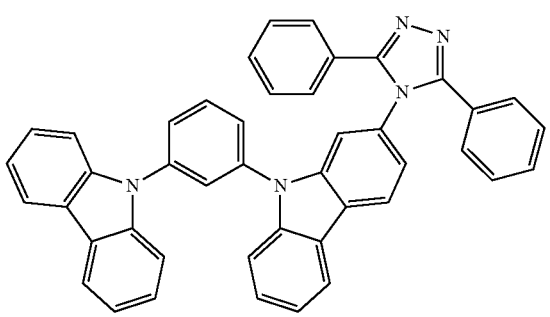
30
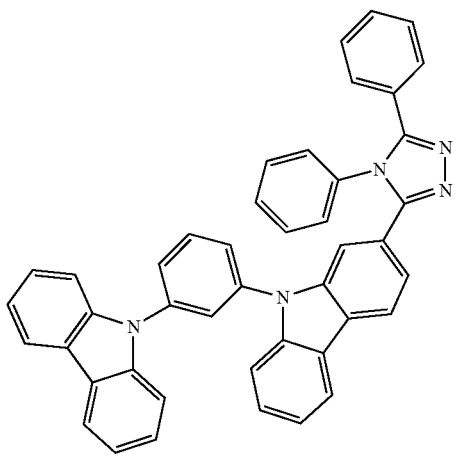
31
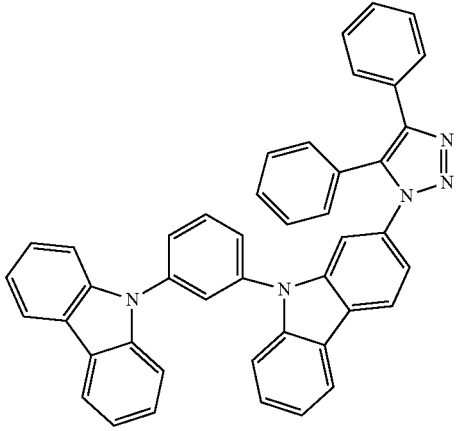
32
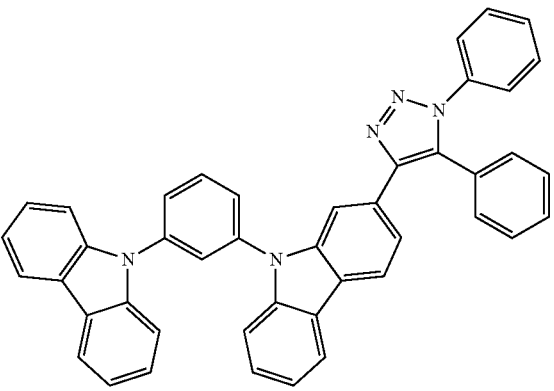

-continued
33
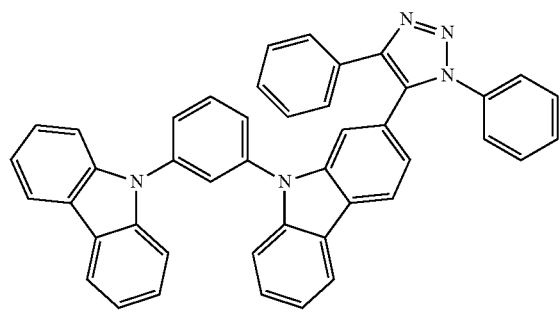
34
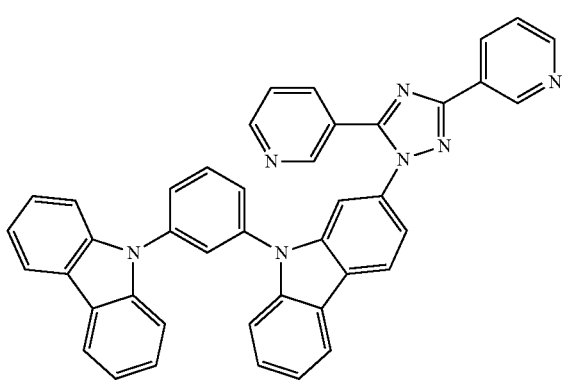
35
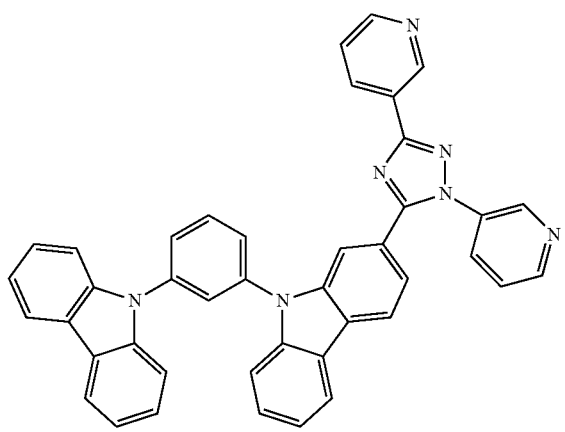
36
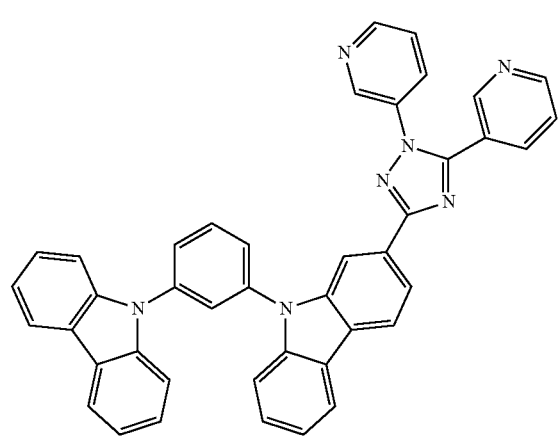
-continued
37
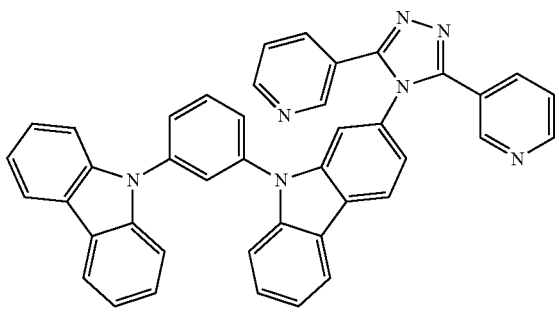
38
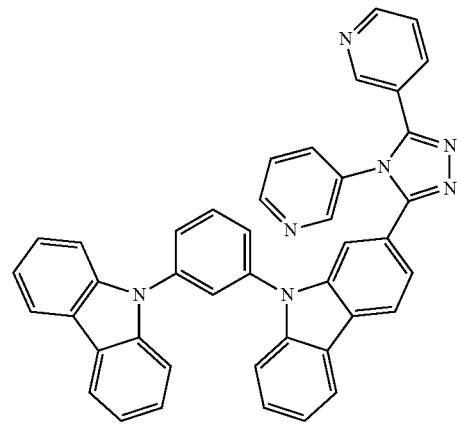
39
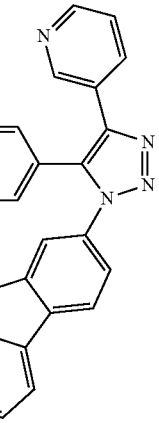
40
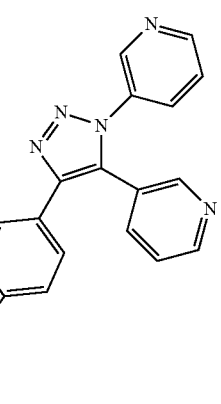

41
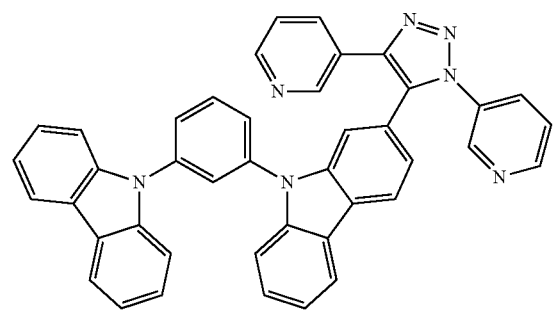
42
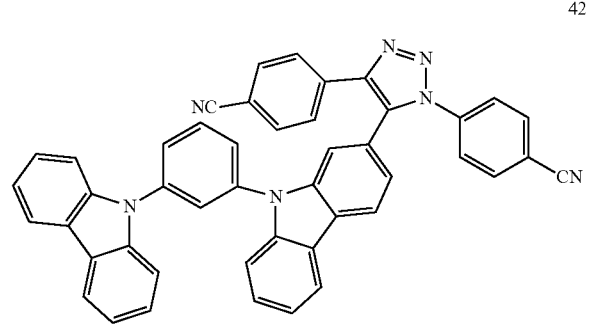
43
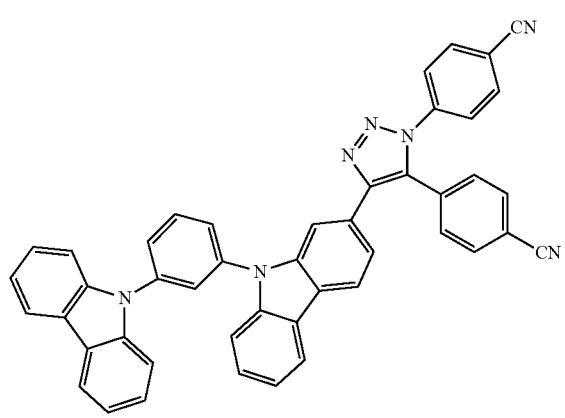
44
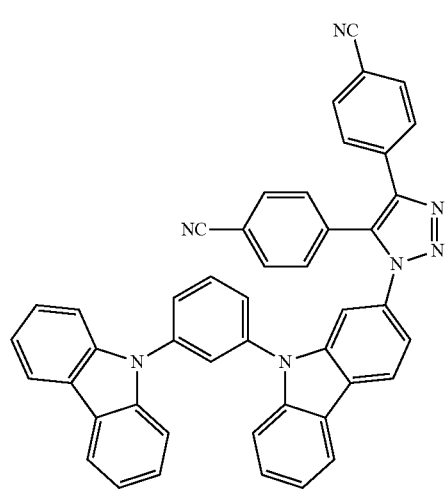
45
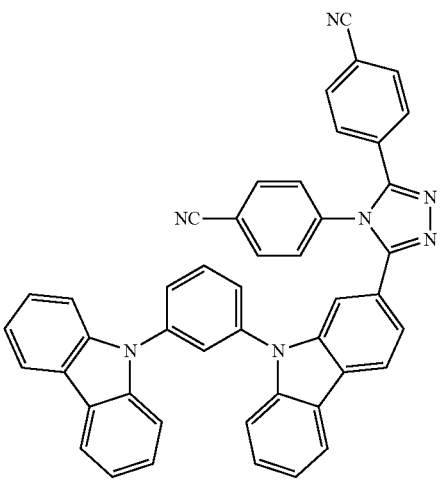
46
47
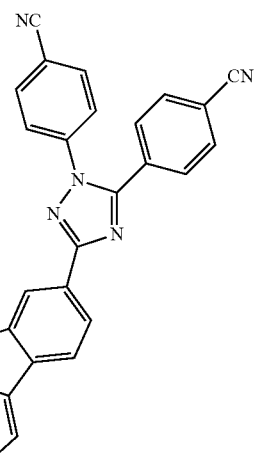

48
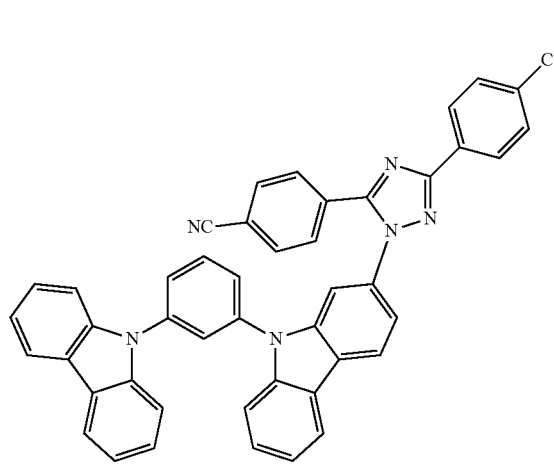
49
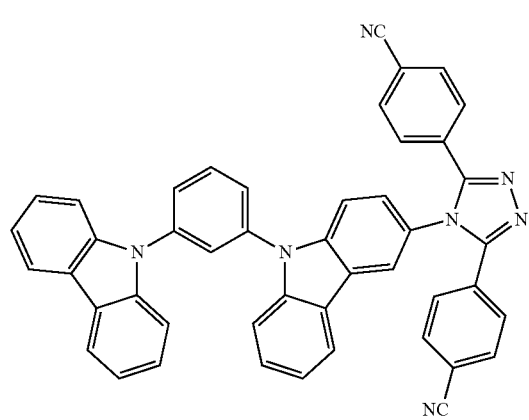
50
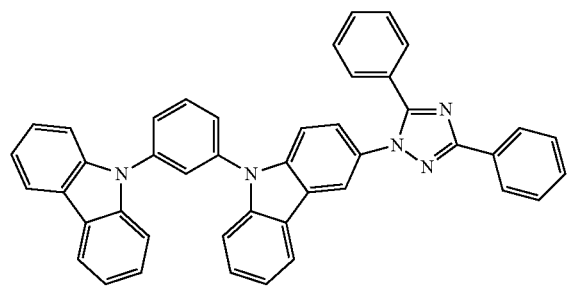
51
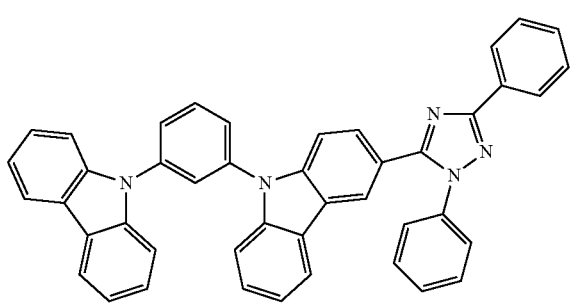
52
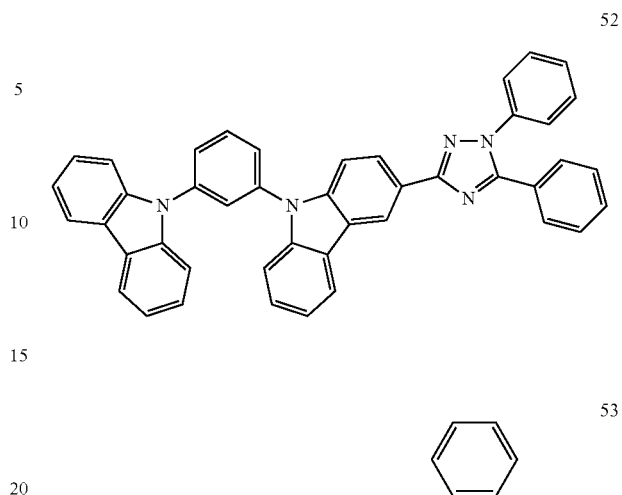
53
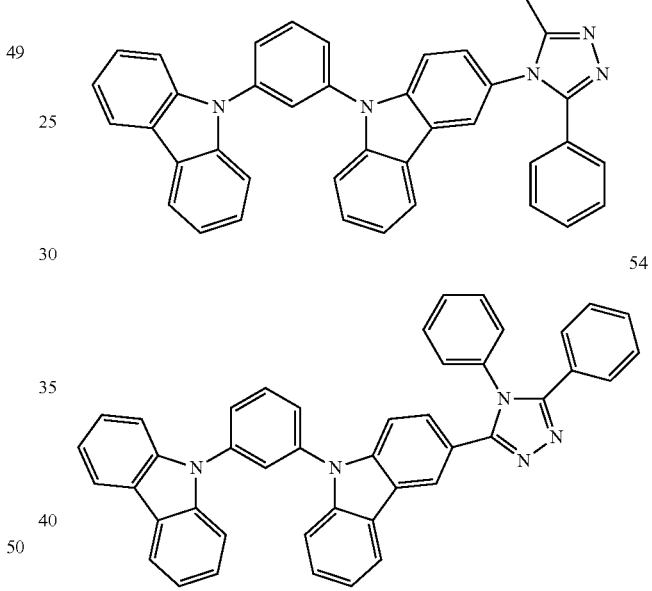
54
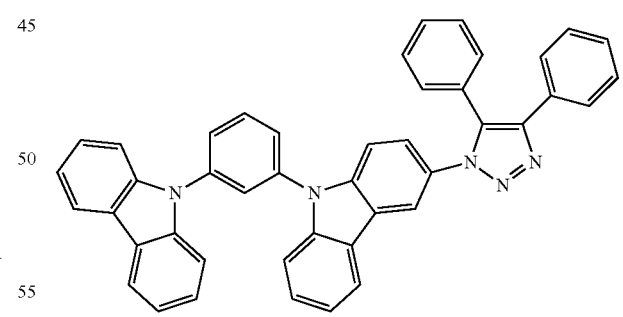
55
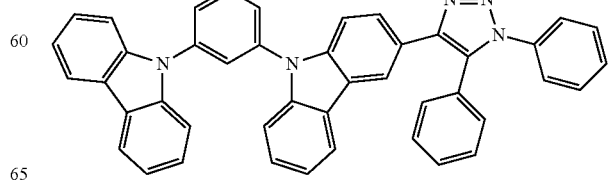
56

57
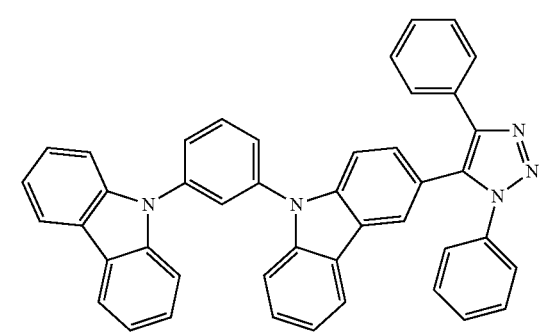
58
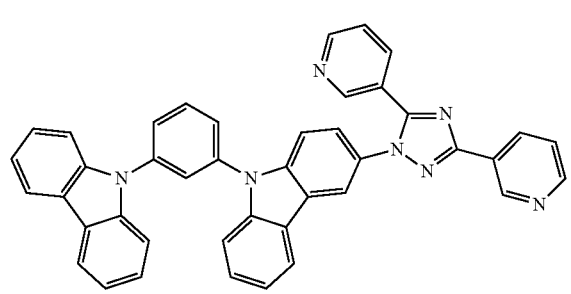
59
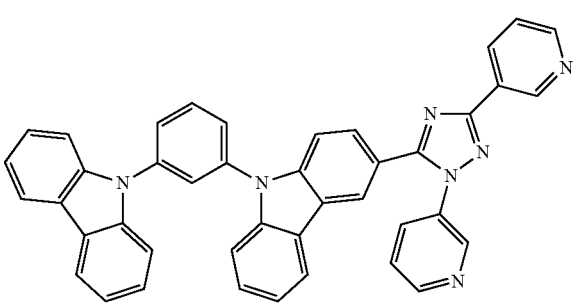
60
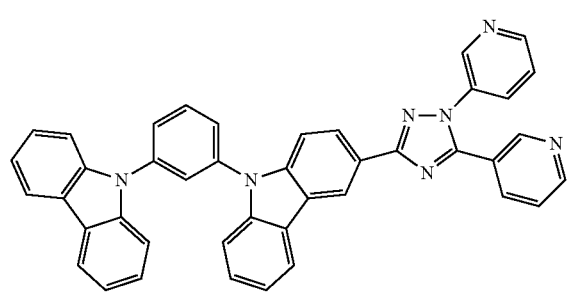
61
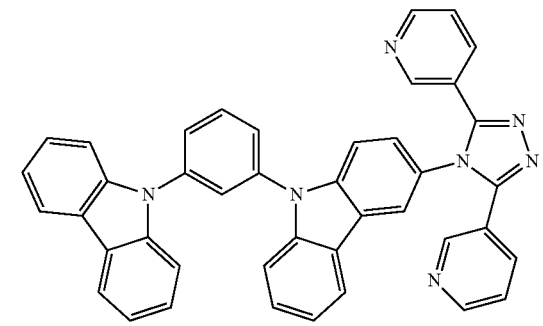
62
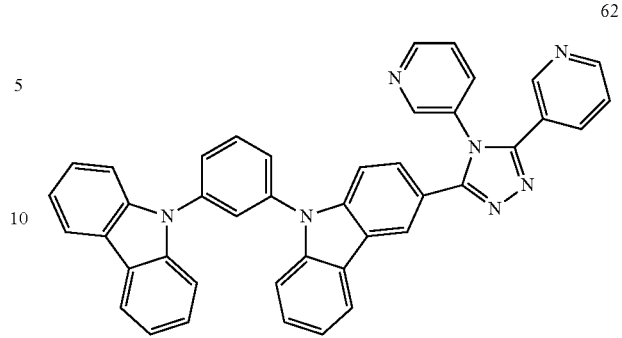
63
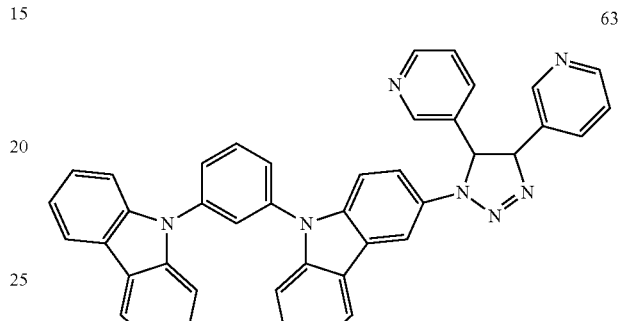
64
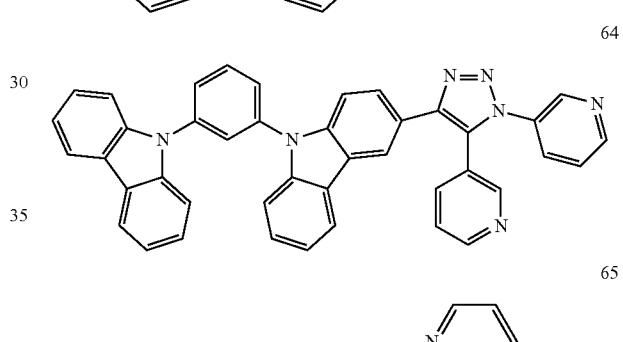
65
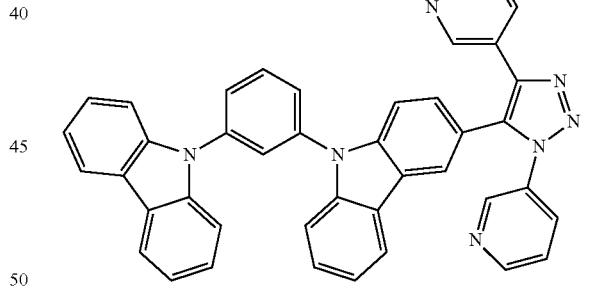
66
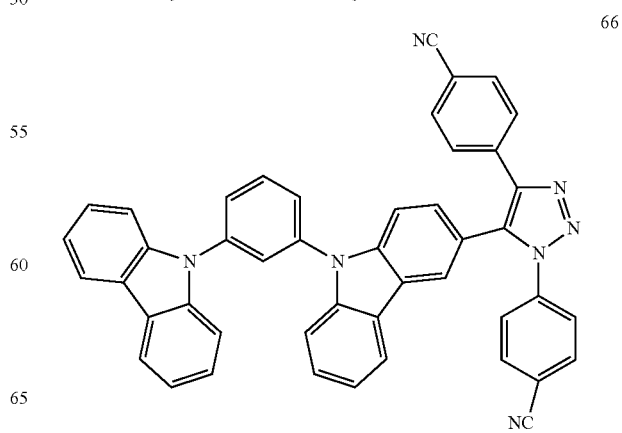

67
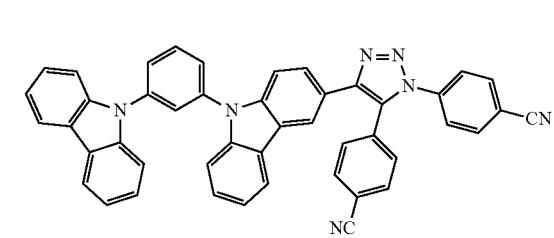
68
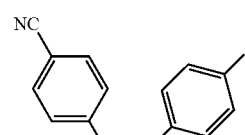
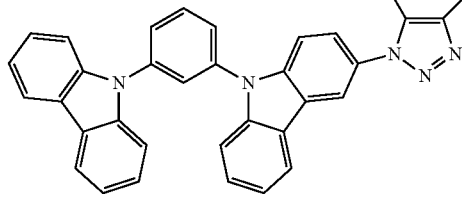
69
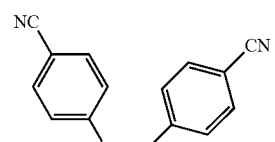
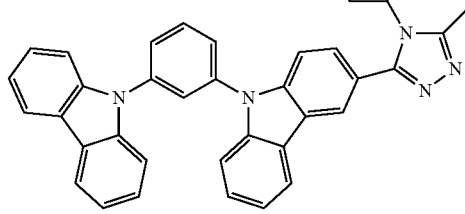
70
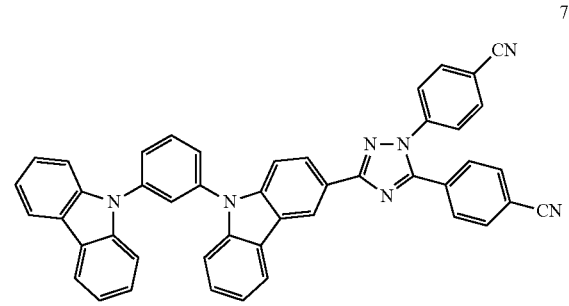
71
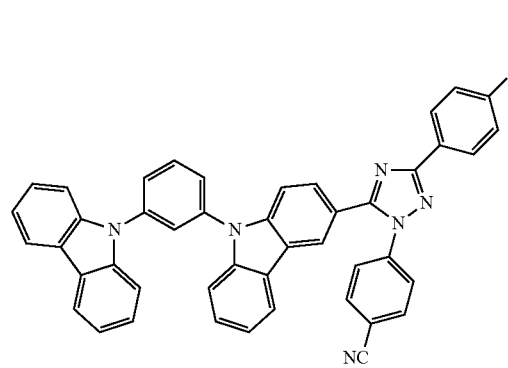
72
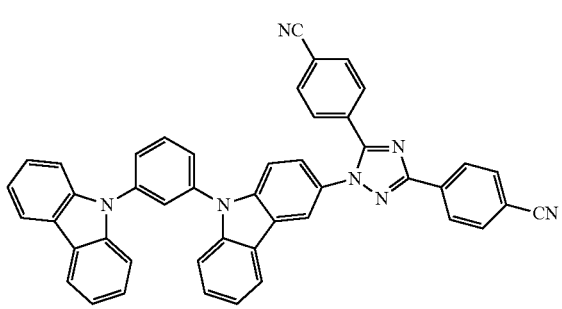
73
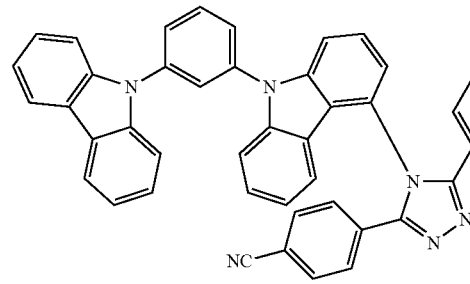
74
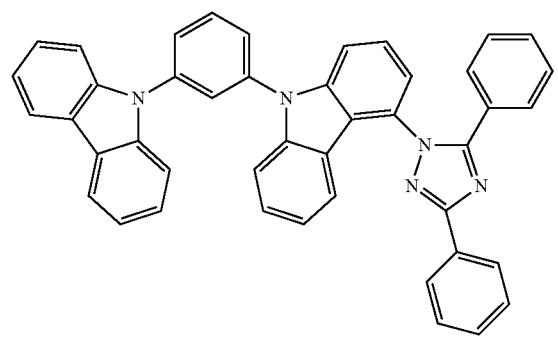
75
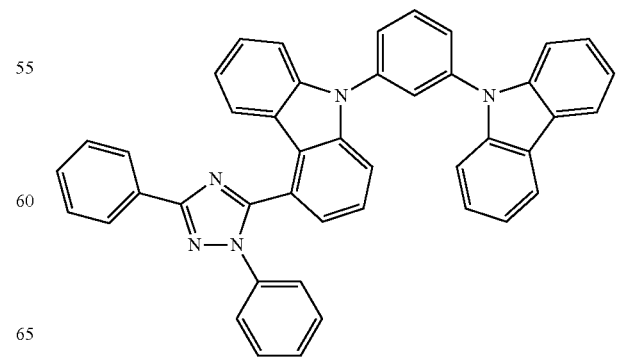

76
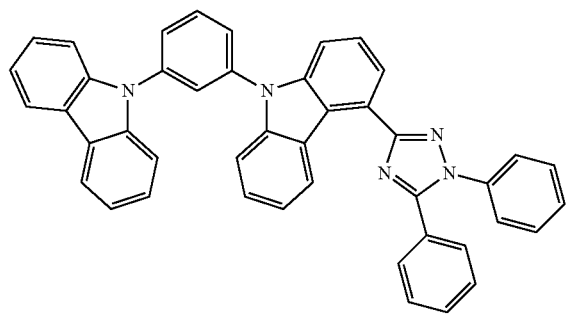
77
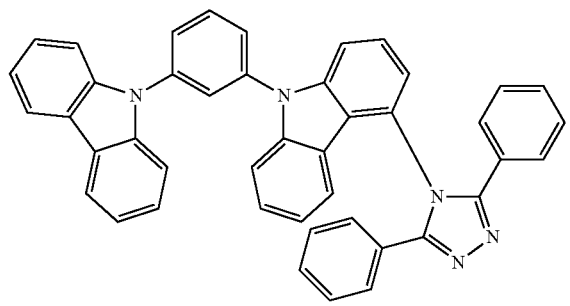
78
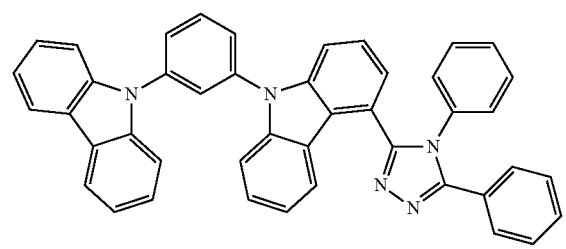
79
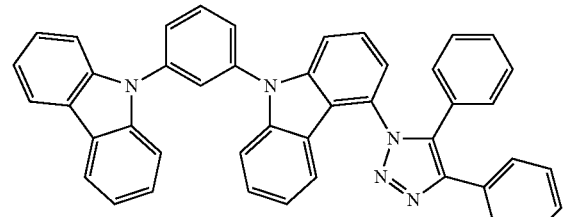
80
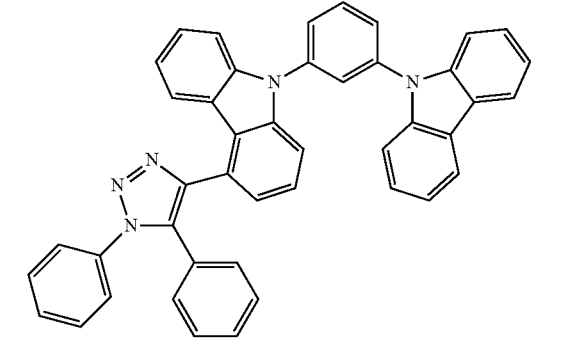
81
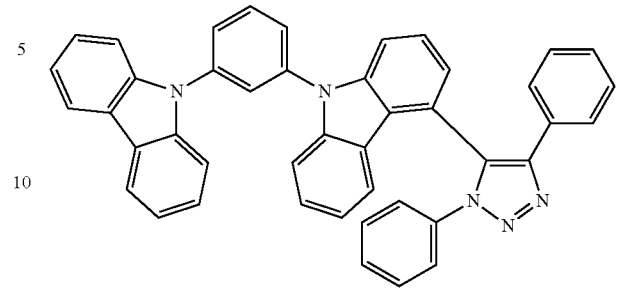
82
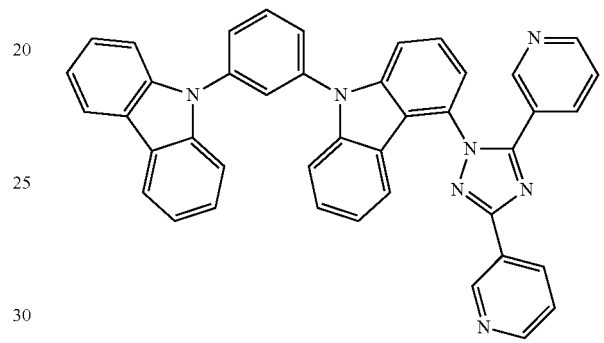
83
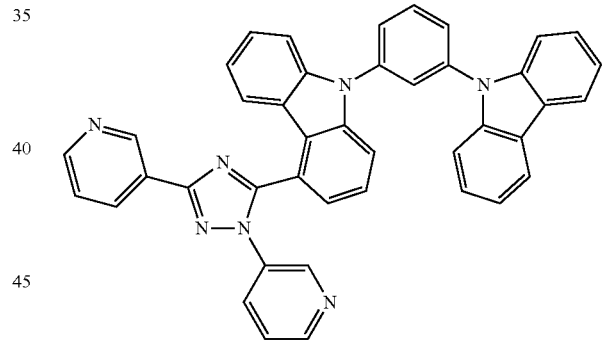
84
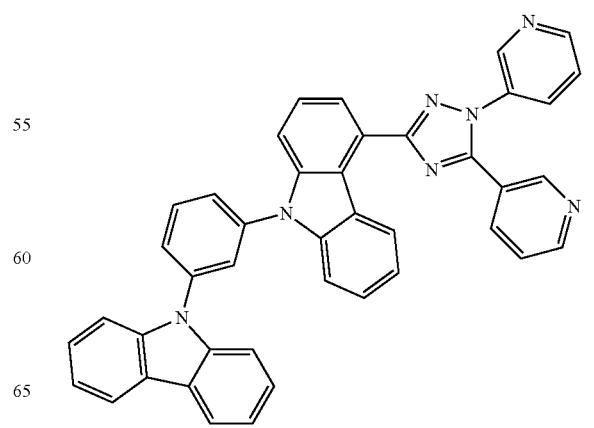

153
-continued
85
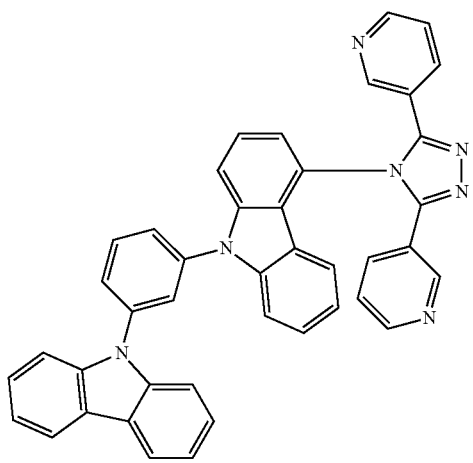
86
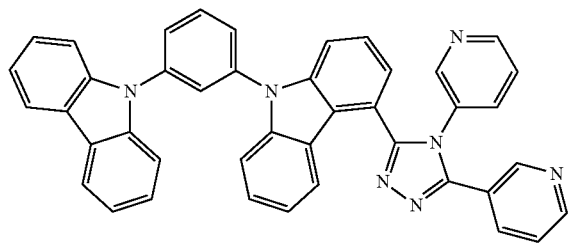
87
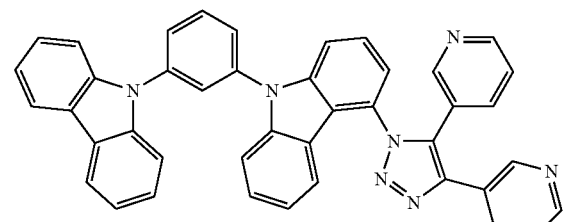
88
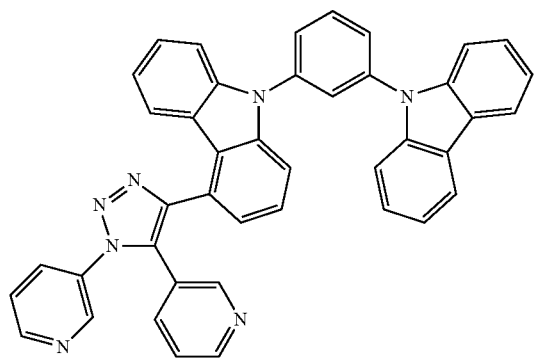
154
-continued
89
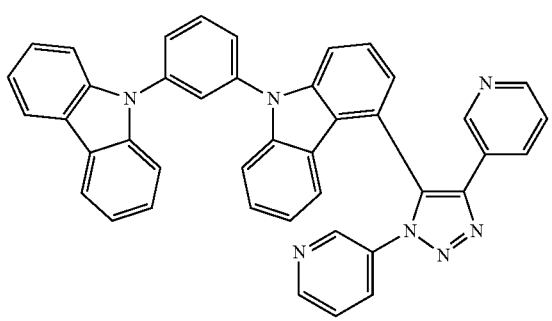
90
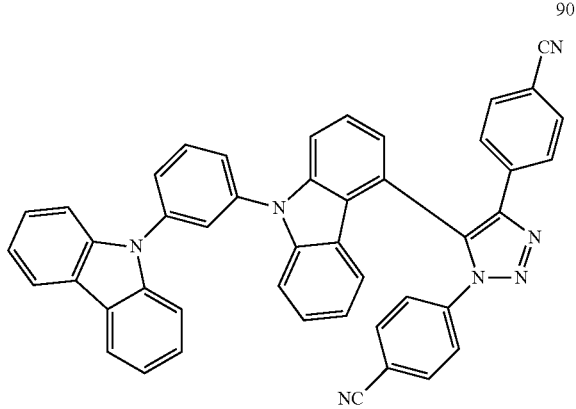
91
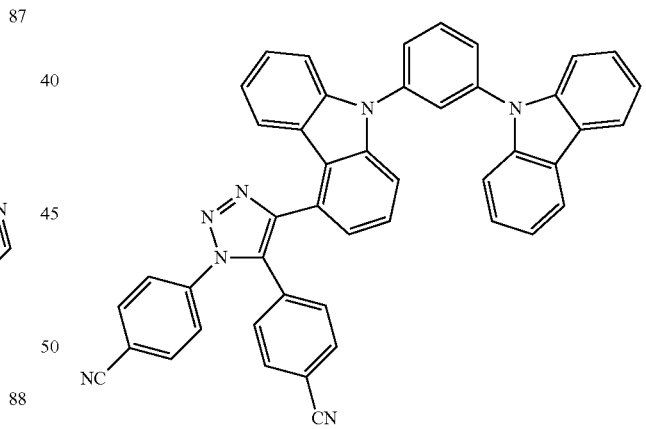
92
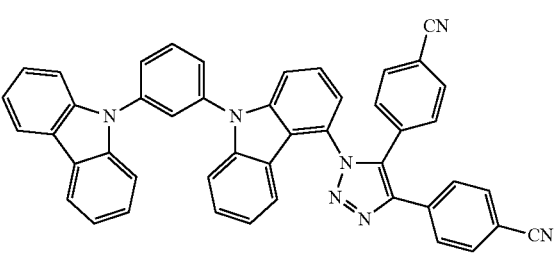

93
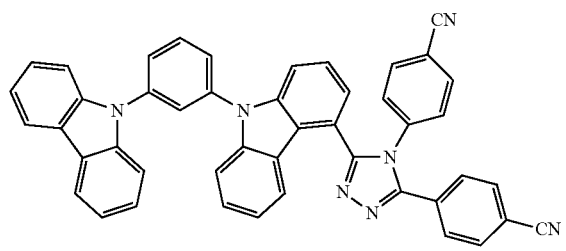
94
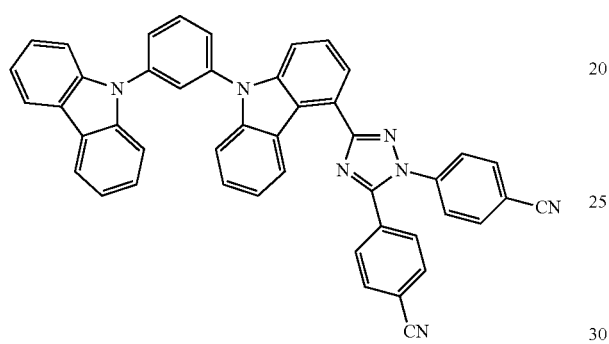
95
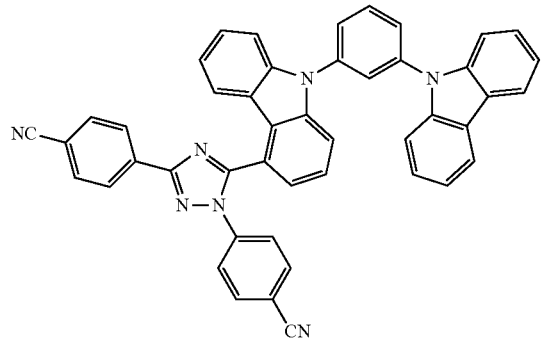
96
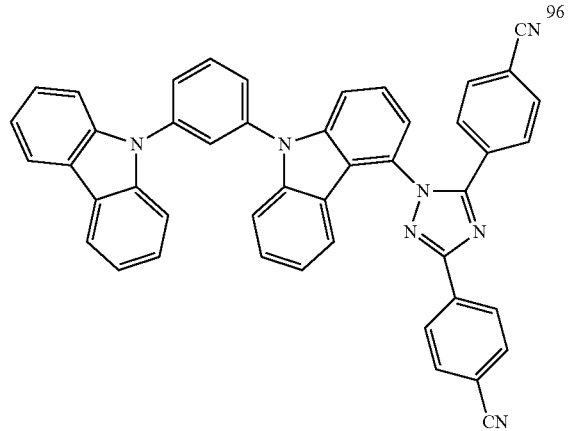
97
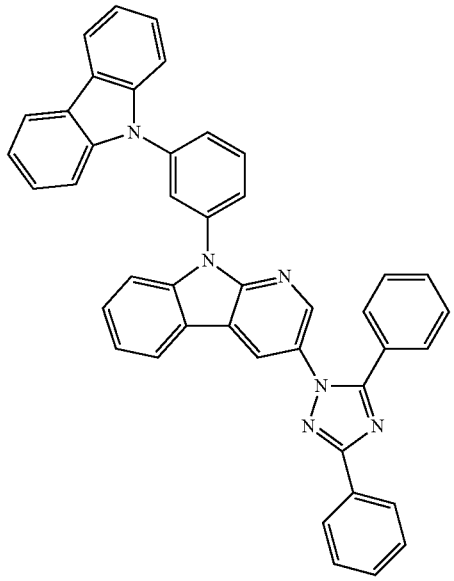
98
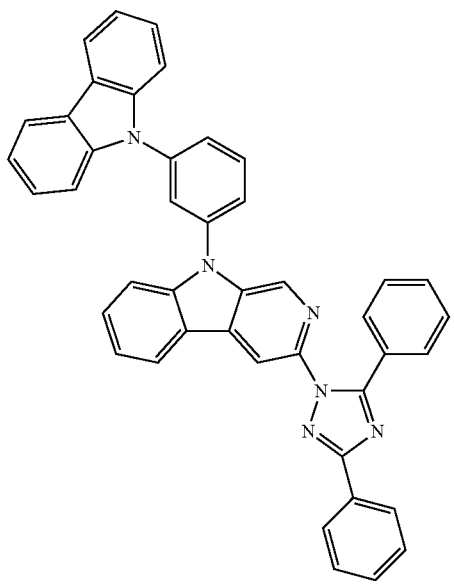
99
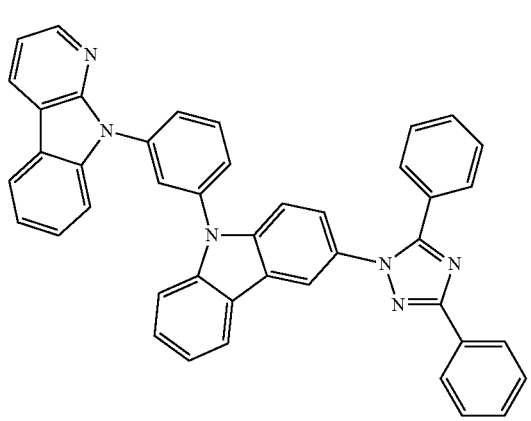

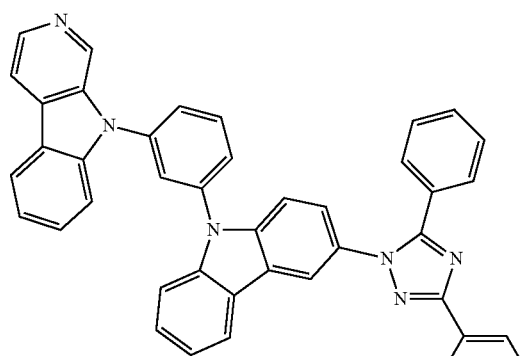
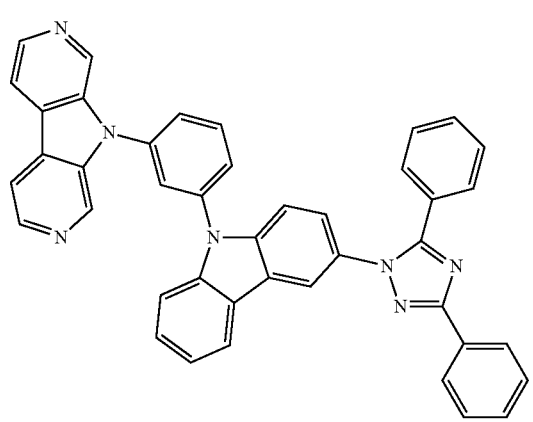
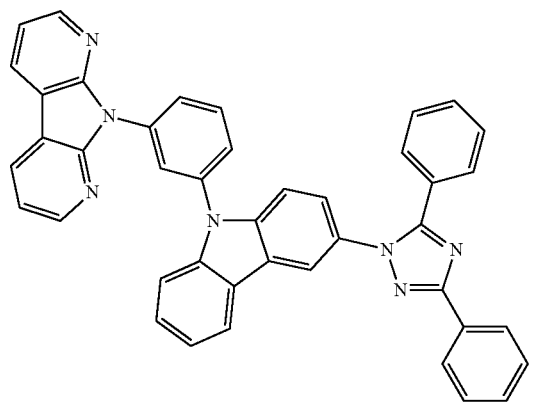
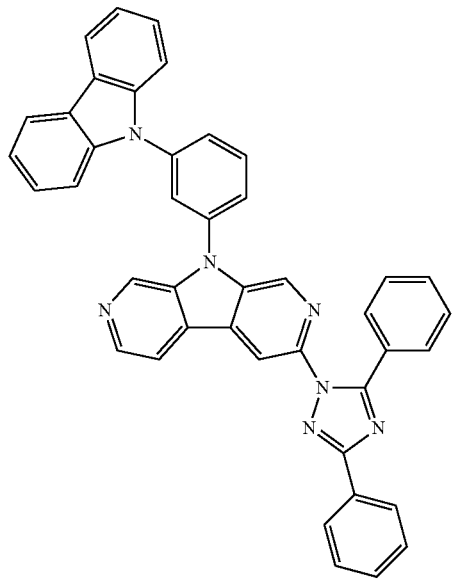
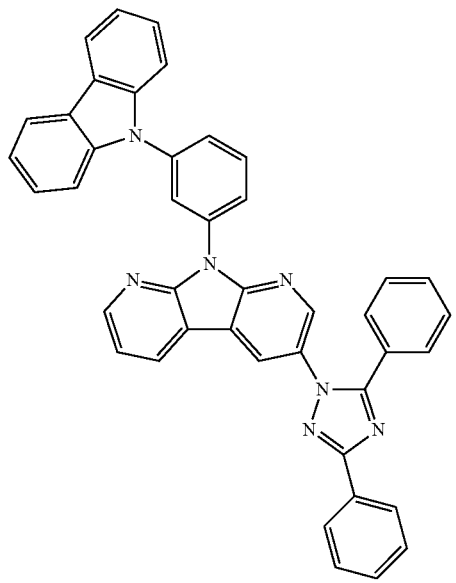

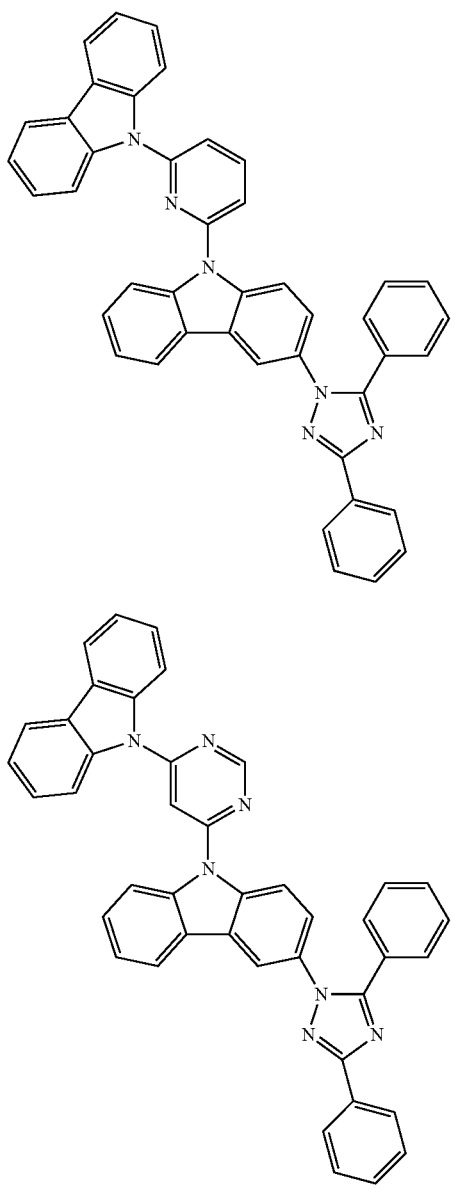

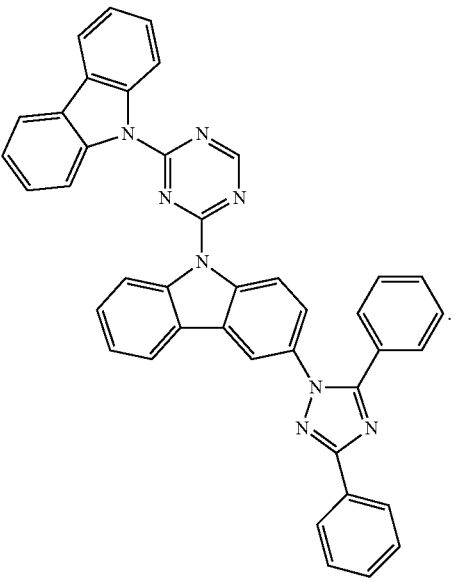

18. An organic light-emitting device, comprising:
a first electrode;
a second electrode; and
an organic layer disposed between the first electrode and the second electrode, wherein the organic layer comprises an emission layer and the condensed cyclic compound of claim 1.

19. The organic light-emitting device of claim 18, wherein the emission layer comprises the condensed cyclic compound of claim 1.

20. The organic light-emitting device of claim 19, wherein the emission layer further comprises a dopant, and wherein the condensed cyclic compound of claim 1 acts as a host.

* * * * *